US008036831B2

(12) United States Patent
Umeyama et al.

(10) Patent No.: US 8,036,831 B2
(45) Date of Patent: Oct. 11, 2011

(54) LIGAND SEARCHING DEVICE, LIGAND SEARCHING METHOD, PROGRAM, AND RECORDING MEDIUM

(75) Inventors: Hideaki Umeyama, Chiba (JP); Yoshiaki Watanabe, Shizuoka (JP); Ryoichi Arai, Saitama (JP)

(73) Assignee: In-Silico Sciences, Inc., Tokyo (JP)

( * ) Notice: Subject to any disclaimer, the term of this patent is extended or adjusted under 35 U.S.C. 154(b) by 1391 days.

(21) Appl. No.: 10/590,116

(22) PCT Filed: Feb. 24, 2005

(86) PCT No.: PCT/JP2005/003558
§ 371 (c)(1),
(2), (4) Date: Aug. 18, 2006

(87) PCT Pub. No.: WO2005/083616
PCT Pub. Date: Sep. 9, 2005

(65) Prior Publication Data
US 2007/0166760 A1    Jul. 19, 2007

(30) Foreign Application Priority Data

Feb. 24, 2004    (JP) .................................. 2004-048767

(51) Int. Cl.
*G06F 19/00*    (2011.01)
*G01N 33/566*    (2006.01)
(52) U.S. Cl. .......................................... 702/19; 436/501
(58) Field of Classification Search .................. None
See application file for complete search history.

(56) References Cited

U.S. PATENT DOCUMENTS

| 5,642,292 | A | 6/1997 | Itai et al. |
| 2001/0018682 | A1 | 8/2001 | Itai et al. |
| 2003/0190670 | A1 | 10/2003 | Bursavich et al. |

FOREIGN PATENT DOCUMENTS

| EP | 1724697 A1 | 11/2006 |
| WO | WO 93/20525 A1 | 10/1993 |
| WO | WO 96/13785 A1 | 5/1996 |
| WO | WO 02/057954 A1 | 7/2002 |
| WO | WO 03/072596 A2 | 9/2003 |

OTHER PUBLICATIONS

Hammer et al., "Glucocorticoid receptor interactions with glucocorticoids: evaluation by molecular modeling and functional analysis of glucocorticoid receptor mutants", Steroids, 2003, vol. 68, pp. 329-339.

Cavasotto et al., "Protein Flexibility in Ligand Docking and Virtual Screening to Protein Kinases", J. Mol. Biol. 2004, vol. 337, pp. 209-225.

Hideaki Umeyama, "Tanpakushitsu no Yudo Tekigo o Koryoshita Ligand Tansaku System", Dai 32 Kai Kozo Kassei Sokan Symposium Koen Yoshishu, Nov. 10, pp. 33-36 (2004).

Noriyuki Yamaoto, "Hyoteki Tanpakushitsu no Induced Fit o Koryoshita Ligand Docking (1) : Brownian Doryoku Gakuho o Mochiita Fukugotai Kozo Saitekika", Dai 31 Kai Kozo Kassei Symposium Koen Yoshishu, pp. 115-118 (2003).

G.M. Morris et al., "Automated Docking Using a Lamarckian Genetic Algorithm and an Empirical Binding Free Energy Function", Journal of Computational Chemistry, Vo. 19, No. 14, pp. 1639-1662 (1998).

David S. Goodsell et al., "Automated Docking of Flexible Ligands: Applications of AutoDock", Journal of Molecular Recognition, vol. 9, pp. 1-5 (1996).

Todd J. Ewing et al., "Dock 4.0: Search strategies for automated molecular docking of flexible molecule databases", Journal of Computer-Aided Molecular Design, 15, pp. 411-428 (2001).

Matthias Rarey et al., "A Fast Flexible Docking Method using an Incremental Construction Algorithm", J. Mol. Biol. 261, pp. 470-489 (1996).

Matthias Rarey et al., "Placement of medium-sized molecular fragments into active sites of proteins", Journal of Computer-Aided Molecular Design, 10, pp. 41-54 (1996).

Gareth Jones et al., "Molecular Recognition of Receptor Sites using a Genetic Algorithm with a Description of Desovation", J. Mol. Biol., 245, pp. 43-53 (1995).

Gareth Jones et al., "Development and Validation of a Genetic Algorithm for Flexible Docking", J. Mol. Biol., 267, pp. 727-748 (1997).

Miho Yamada Mizutani et al., "Efficient Method for High-Throughput Virtual Screening Based on Flexible Docking: Discovery of Novel Acetylcholinesterase Inhibitors", J. Med. Chem., 47, pp. 4818-4828 (2004).

*Primary Examiner* — Lori A Clow

(74) *Attorney, Agent, or Firm* — Foley & Lardner LLP

(57) ABSTRACT

The present invention is directed to serve ligand screening apparatuses, ligand screening methods, programs and a recording medium for studying the binding analysis between a receptor including an induced-fit type receptor and a ligand. First, analysis and calculation of normal mode are conducted, and then fluctuation of a dihedral angle of a main chain in a steady state is calculated. Then by carrying out a molecular dynamic calculation while imposing constraint on each atom based on the fluctuation, a dynamic structure of the receptor is predicted more accurately. By using the dynamic structure obtained in the molecular dynamic calculation and an interaction function, receptor/ligand binding which is also applicable to an induced-fit type receptor is predicted with high accuracy.

28 Claims, 69 Drawing Sheets

FIG.12

| RANKING | MINIMUM VALUE | MAXIMUM VALUE | α [%] | β [Å] | NUMBER OF CLUSTERS | SCORE |
|---|---|---|---|---|---|---|
| 1 | 0 | 800 | 70 | 0.4 | 57 | 0.9054 |
| 2 | 0 | 800 | 70 | 0.1 | 62 | 0.9097 |
| 3 | 0 | 800 | 70 | 0.2 | 62 | 0.9097 |
| 4 | 0 | 800 | 70 | 0.3 | 62 | 0.9097 |
| 5 | 0 | 800 | 80 | 0.1 | 81 | 0.9102 |
| 6 | 0 | 800 | 80 | 0.2 | 81 | 0.9102 |
| 7 | 0 | 800 | 70 | 0.5 | 52 | 0.9103 |
| 8 | 0 | 800 | 80 | 0.4 | 73 | 0.9106 |
| 9 | 0 | 800 | 80 | 0.3 | 80 | 0.9116 |
| 10 | 0 | 800 | 80 | 0.5 | 67 | 0.9151 |
| 11 | 0 | 800 | 70 | 0.6 | 46 | 0.9156 |
| 12 | 0 | 800 | 90 | 0.5 | 240 | 0.9183 |
| 13 | 0 | 800 | 90 | 0.6 | 174 | 0.9194 |
| 14 | 0 | 800 | 60 | 0.6 | 13 | 0.9211 |
| 15 | 0 | 800 | 90 | 0.4 | 297 | 0.9225 |
| 16 | 0 | 800 | 80 | 0.6 | 58 | 0.9261 |
| 17 | 0 | 800 | 90 | 0.1 | 425 | 0.9286 |
| 18 | 0 | 800 | 90 | 0.2 | 425 | 0.9286 |
| 19 | 0 | 800 | 90 | 0.3 | 420 | 0.9296 |
| 20 | 0 | 800 | 60 | 0.1 | 16 | 0.9354 |
| 21 | 0 | 800 | 60 | 0.2 | 16 | 0.9354 |
| 22 | 0 | 800 | 60 | 0.3 | 16 | 0.9354 |
| 23 | 0 | 800 | 60 | 0.4 | 16 | 0.9354 |
| 24 | 0 | 800 | 60 | 0.5 | 15 | 0.9451 |
| 25 | 600 | 900 | 60 | 0.1 | 28 | 0.9469 |
| 26 | 600 | 900 | 60 | 0.2 | 28 | 0.9469 |
| 27 | 600 | 900 | 60 | 0.3 | 28 | 0.9469 |
| 28 | 600 | 900 | 60 | 0.4 | 28 | 0.9469 |
| 29 | 600 | 900 | 60 | 0.5 | 27 | 0.9518 |
| 30 | 600 | 900 | 60 | 0.6 | 27 | 0.9518 |

| MINIMUM VALUE OF CONSTRAINED MD | 0.00 |
|---|---|
| MAXIMUM VALUE OF CONSTRAINED MD | 800.00 |
| CLUSTERING COEFFICIENT $\alpha$ (%) | 80.00 |
| CLUSTERING COEFFICIENT $\beta$ (Å) | 0.40 |

Cα OF ACTIVE SITE

MAIN CHAIN OF ACTIVE SITE

FIG.17
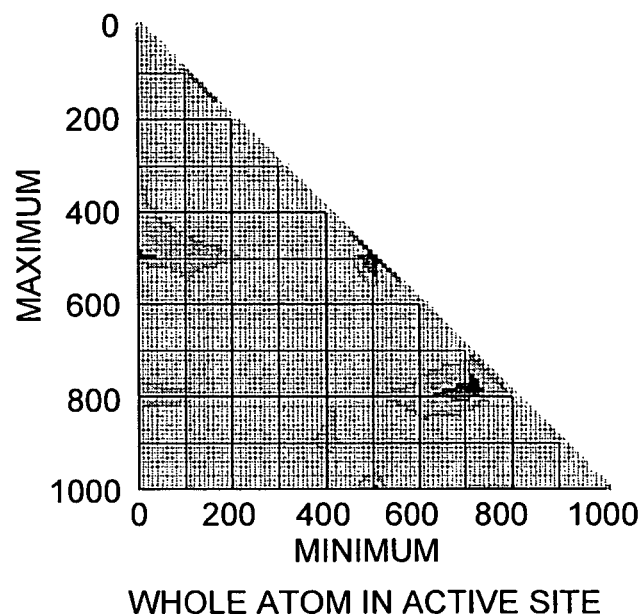
WHOLE ATOM IN ACTIVE SITE
FIG.18
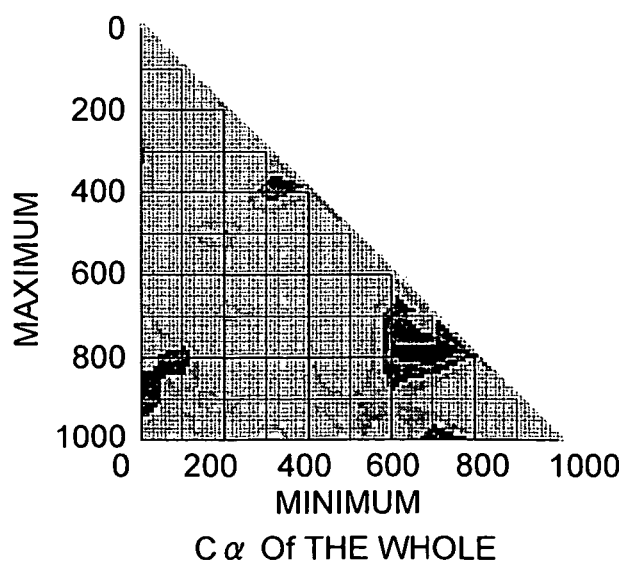
Cα Of THE WHOLE

FIG.22

>1CBQ
PNFSGNVWKIIRSENFEELLKVLGVNVMLRKIAVAAASKPAVEIKQEGDTFYIKTSTTVRTTEINFKVGEEFEEQTVDGRP
CKSLVKWESENKMVCEQKLLKGEGPKTSWTRELTNDGELILTMTADDVVCTRVYVRE
>1ICM
-AFDGTWKVDRNENYEKFMEKMGINVVKRKLG-AHDNLKLTITQEGNKFTVKESSNFRNIDVVFELGVDFAYSLADGTE
L-TGTWTMEGNKLVGKFKRV-DNGKELIAVREIS-GNELIQTYTYEGVEAKRIFKKE

FIG.25

| X-RAY STRUCTURE | 1CBQ |
|---|---:|
| REFERENCE PROTEIN | 1ICM |
| HOMOLOGY [%] | 32.1 |
| NUMBER OF RESIDUES | 136 |
| MAIN CHAIN IN ACTIVE SITE [Å] | 2.2487 |
| SIDE CHAIN IN ACTIVE SITE [Å] | 3.2446 |
| ALL ATOMS IN ACTIVE SITE [Å] | 2.7728 |
| MAIN CHAIN IN THE WHOLE [Å] | 2.2075 |
| SIDE CHAIN IN THE WHOLE [Å] | 3.7881 |
| ALL ATOMS IN THE WHOLE [Å] | 3.0959 |

FIG.29

>1J9G
AKALIVYGSTTGNTEYTAETIARELADAGYEVDSRDAASVEAGGLFEGFDLVLLGCSTWGD-DCIELQDDFIPLFDSLEE
TGAQGRKVACFGCGDS--SYEYFCGAVDAIEEKLKNLGAEIVQDG----------LRIDGDPRAARDDI
VGWAHDVRGAI
>1AHN
AITGIFFGSDTGNTENIAKMIQKQLGKDVADVHDIAKSSKE---DLEAYDILLLGIPTWYG---EAQCDWDDFFPTLEE
IDFNGKLVALFGCGDQEDYAEYFCDALGTIRDIIEPRGATIVGHWPTAGYHFEASKGLADDDHFVGLAIDEDRQPELTAE
RVEKWVKQISE

FIG.32

| X-RAY STRUCTURE | 1J9G |
|---|---|
| REFERENCE PROTEIN | 1AHN |
| HOMOLOGY [%] | 29.2 |
| NUMBER OF RESIDUES | 147 |
| MAIN CHAIN IN ACTIVE SITE [Å] | 2.3909 |
| SIDE CHAIN IN ACTIVE SITE [Å] | 4.5774 |
| ALL ATOMS IN ACTIVE SITE [Å] | 3.5753 |
| MAIN CHAIN IN THE WHOLE [Å] | 3.1212 |
| SIDE CHAIN IN THE WHOLE [Å] | 5.367 |
| ALL ATOMS IN THE WHOLE [Å] | 4.315 |

FIG. 36

>1MMB
NPKWERTNLTYRIRNYTPQLSEAEVERAIKDAFELWSVASPLIFTRISQGEADINIAFYQRDHGDNSPFDGPNGILAHAF
QPGQGIGGDAHFDAEETWTNTSANYNLFLVAAHEFGHSLGLAHSSDPGALMYPNYA-FRETSNYSLPQDDIDGIQAIYG
>1B3D_A
IPKWRKTHLTYRIVNYTPDLPKDAVDSAVEKALKVWEEVTPLTFSRLYEGEADIMISFAVREHGDFYPFDGPGNVLAHAY
APGPGINGDAHFDDDEQWTKDTTGTNLFLVAAHEIGHSLGLFHSANTEALMYPLYHSLTDLTRFRLSQDDINGIQSLYG

FIG.39

| X-RAY STRUCTURE | 1MMB |
|---|---:|
| REFERENCE PROTEIN | 1B3D |
| HOMOLOGY [%] | 55 |
| NUMBER OF RESIDUES | 158 |
| MAIN CHAIN IN ACTIVE SITE [Å] | 0.9442 |
| SIDE CHAIN IN ACTIVE SITE [Å] | 3.0756 |
| ALL ATOMS IN ACTIVE SITE [Å] | 2.2417 |
| MAIN CHAIN IN THE WHOLE [Å] | 1.1339 |
| SIDE CHAIN IN THE WHOLE [Å] | 2.5715 |
| ALL ATOMS IN THE WHOLE [Å] | 1.9808 |

FIG.46

| ATOM OF ACTIVE SITE | ATOM TYPE OF LIGAND | INTENSITY OF INTERACTION | DISTANCE OF INTERACTION [Å] |
|---|---|---|---|
| LUE4   O | N.pl3 | 300 | 2.87 |
| ASP26  OD1 | N.ar | 300 | 3.00 |
| ASP26  OD2 | N.pl3 | 300 | 3.00 |

FIG.47

| SECTION [nsec] | DISTANCE [fsec] | NUMBER OF CLUSTERS | MAIN CHAIN [Å] | ALL ATOMS [Å] | LIGAND [Å] |
|---|---|---|---|---|---|
| INITIAL STRUCTURE | | | 1.5313 | 1.9190 | |
| 0~0.1 | 100 | 11 | 1.3531 | 1.8612 | 1.2734 |
| 0~1.0 | 100 | 204 | 1.2522 | 1.8116 | 0.9614 |
| 0~1.0 | 1000 | 26 | 1.2522 | 1.8116 | 0.8169 |

FIG.54

| ATOM OF ACTIVE SITE | ATOM TYPE OF LIGAND | INTENSITY OF INTERACTION | DISTANCE OF INTERACTION [Å] |
|---|---|---|---|
| LYS58 NZ | O.3 | 300 | 2.8 |
| ASP93 OD2 | N.am | 300 | 2.8 |
| PHE138 N | O.2 | 300 | 2.8 |

FIG.55

| SECTION [nsec] | DISTANCE [fsec] | NUMBER OF CLUSTERS | MAIN CHAIN [Å] | ALL ATOMS [Å] | LIGAND [Å] |
|---|---|---|---|---|---|
| INITIAL STRUCTURE | | | 2.0144 | 2.2600 | |
| 0~0.1 | 100 | 6 | 1.8525 | 2.2601 | 1.2081 |
| 0~1.0 | 100 | 133 | 1.9139 | 2.3883 | 1.5932 |
| 0~1.0 | 1000 | 9 | 1.9764 | 2.8421 | 0.9667 |

FIG.61

| ATOM OF ACTIVE SITE | ATOM TYPE OF LIGAND | INTENSITY OF INTERACTION | DISTANCE OF INTERACTION [Å] |
|---|---|---|---|
| LEU75 CD1 | F | 300 | 3.6 |
| LEU75 CD2 | F | 300 | 3.6 |
| MET109 N | N.ar | 300 | 2.7 |

FIG.62

| SECTION [nsec] | DISTANCE [fsec] | NUMBER OF CLUSTERS | MAIN CHAIN [Å] | ALL ATOMS [Å] | LIGAND [Å] |
|---|---|---|---|---|---|
| INITIAL STRUCTURE | | | 1.7972 | 2.1606 | |
| 0~0.1 | 100 | 5 | 1.6101 | 2.0766 | 1.6112 |
| 0~1.0 | 100 | 319 | 1.7236 | 2.2843 | 1.4550 |
| 0~1.0 | 1000 | 31 | 1.7236 | 2.2843 | 1.4571 |

FIG. 67

| RANKING | INTERACTION ENERGY | PDBcode | RANKING | INTERACTION ENERGY | PDBcode |
|---|---|---|---|---|---|
| [001] | -3847.2147 | 4PGT | [002] | -3671.4754 | 1MP7 |
| [003] | -3056.6135 | 1BMN | [004] | -2923.8680 | 1I32 |
| [005] | -2872.4420 | 5FWG | [006] | -2608.5702 | 1LHF |
| [007] | -2528.6110 | 1BX6 | [008] | -2439.5657 | 1B8Y |
| [009] | -2433.9052 | 1EZF | [010] | -2382.8539 | 5LDH |
| [011] | -2248.0139 | 1FVP | [012] | -2247.3089 | 1JJQ |
| [013] | -2133.5942 | 1IL2 | [014] | -2128.4540 | 1BJI |
| [015] | -2125.1405 | 1DMT | [016] | -2103.1434 | 1K22 |
| [017] | -2092.6654 | 1HY7 | [018] | -2025.5091 | 966C |
| [019] | -2013.9064 | 1AIX | [020] | -1989.1635 | 1A4Q |
| [021] | -1946.4497 | 1VZE | [022] | -1932.9896 | 1KVO |
| [023] | -1928.3650 | 1D6V | [024] | -1901.6172 | 1C0A |
| [025] | -1890.2208 | 1DB5 | [026] | -1867.0754 | 1GUH |
| [027] | -1855.6184 | 1QIN | [028] | -1817.4767 | 1M21 |
| [029] | -1782.5387 | 1KCI | [030] | -1766.9010 | 1KZK |
| [031] | -1728.2876 | 6GSX | [032] | -1709.9359 | 2PRG |
| [033] | -1699.2351 | 1NPW | [034] | -1694.4086 | 2UPJ |
| *[035]* | *-1661.4315* | *1AUJ* | [036] | -1658.1970 | 1HFR |
| [037] | -1654.2430 | 1DMP | *[038]* | *-1599.5870* | *1F0R* |
| [039] | -1595.7907 | 2GSQ | [040] | -1569.9256 | 1QHC |
| [041] | -1530.3871 | 1AIM | [042] | -1481.1846 | 1EL3 |
| [043] | -1473.7372 | 1QH5 | [044] | -1453.3935 | 1LHC |
| [045] | -1411.1465 | 1HFC | [046] | -1389.8129 | 2FMB |
| [047] | -1372.1506 | 1GFW | [048] | -1352.8868 | 1EM6 |
| [049] | -1329.5658 | 1AU0 | [050] | -1306.5704 | 1M9B |
| [051] | -1287.3729 | 1EAS | [052] | -1265.8962 | 1LHE |
| [053] | -1248.8527 | 1C8T | [054] | -1244.2458 | 1MMQ |
| [055] | -1216.6454 | 1QIP | [056] | -1200.9810 | 207D |
| [057] | -1175.5120 | 1HWL | [058] | -1138.1881 | 4UPJ |
| [059] | -1112.7163 | 3GST | [060] | -1068.0641 | 1LEE |
| [061] | -1030.5972 | 1GA9 | [062] | -1030.4960 | 1OD7 |
| [063] | -1029.0345 | 1HOV | [064] | -1018.1686 | 1LF2 |
| [065] | -1011.9100 | 1ODY | [066] | -976.1041 | 1CQQ |
| [067] | -948.0992 | 1G2K | [068] | -936.9058 | 2AIM |
| [069] | -934.4739 | 1NWL | [070] | -924.6255 | 6FIV |
| [071] | -902.7587 | 1YEI | [072] | -900.4131 | 1MXT |
| [073] | -894.5544 | 1YEF | [074] | -874.9274 | 1DZT |
| [075] | -857.5373 | 1QF0 | [076] | -851.1669 | 1EGV |
| [077] | -844.2406 | 1F29 | [078] | -824.5393 | 1KV2 |
| [079] | -820.4913 | 456C | *[080]* | *-775.9659* | *1K1M* |
| [081] | -766.8359 | 1JR4 | [082] | -763.2825 | 2KCE |
| [083] | -739.3676 | 1KN4 | [084] | -733.8593 | 1RT2 |
| [085] | -728.8765 | 1HPV | [086] | -718.5795 | 2BBQ |
| [087] | -705.3978 | 1MS6 | [088] | -695.0241 | 1IF7 |
| [089] | -689.7998 | 1JIL | [090] | -684.7289 | 1A8J |
| [091] | -676.3861 | 1FL3 | [092] | -628.8081 | 1CIZ |
| [093] | -619.2121 | 1DIF | [094] | -604.7057 | 2BPX |
| [095] | -598.4143 | 1IF9 | [096] | -564.5807 | 1K0C |
| [097] | -561.6472 | 1KN2 | [098] | -541.1021 | 1HBV |
| [099] | -507.6808 | 1DB4 | [100] | -496.0550 | 1K1J |

BOLD: LIGAND CONTAINED IN 1AIX
ITALIC: SERINE PROTEASE

RANKING 19

LIGAND CONTAINED IN 1AIX

RANKING 35

LIGAND CONTAINED IN 1AUJ

RANKING 38

LIGAND CONTAINED IN 1FOR

RANKING 80

LIGAND CONTAINED IN 1KIM

| ATOM OF ACTIVE SITE | ATOM TYPE OF LIGAND | INTENSITY OF INTERACTION | DISTANCE OF INTERACTION [Å] |
|---|---|---|---|
| CYS145  N | O.co2 | 100 | 2.70 |
| MET165  CG | C.3 | 100 | 4.00 |
| GLU166  N | O.2 | 100 | 2.70 |
| THR190  N | O.3 | 100 | 2.70 |

FIG.80

| RANKING | ENERGY | PDB code | REMARKS |
|---|---|---|---|
| 1 | -1089.2153 | 1QF4 | ligase |
| 2 | -990.9917 | 1KZL | transferase |
| 3 | -906.5003 | 1C0A | ligase/RNA |
| 4 | -889.1661 | 1KGQ | transferase |
| 5 | -869.3531 | 1I95 | ribosome |
| 6 | -860.2331 | 1JR4 | transferase |
| 7 | -858.0005 | 1A2N | transferase |
| 8 | -832.0515 | 1NKK | hydrolase |
| 9 | -788.3545 | 1JIL | ligase |
| 10 | -757.2852 | 1EJB | transferase |
| 11 | -697.9477 | 1DMT | hydrolase |
| 12 | -645.0269 | 1PAU | complex (protease/inhibitor) |
| 13 | -633.1260 | 1F74 | lyase |
| 14 | -628.9678 | 1KYU | endocytosis/exocytosis |
| 15 | -616.4458 | 1NRS | serine proteinase/receptor |
| 16 | -608.4169 | 9LYZ | hydrolase (o-glycosyl) |
| 17 | -600.2775 | 1EIO | lipid-binding protein |
| 18 | -593.7082 | 1F7B | lyase |
| 19 | -585.7663 | 1LMW | complex (serine protease/inhibitor) |
| 20 | -584.0059 | 1R1R | oxidoreductase |
| 21 | -580.1563 | 1IL2 | ligase/RNA |
| 22 | -573.0481 | 1BLL | hydrolase(alpha-aminoacylpeptide) |
| 23 | -572.6763 | 1E1F | glycoside hydrolase |
| 24 | -540.1965 | 1LKL | complex (tyrosine kinase/peptide) |
| 25 | -524.2817 | 1UK4 | hydrolase |
| 26 | -518.3528 | 1LCB | transferase (methyltransferase) |
| 27 | -506.8123 | 1PGN | oxidoreductase (choh(d)-nadp+(a)) |
| 28 | -493.5477 | 1I5Q | hydrolase |
| 29 | -486.8954 | 1KYD | endocytosis/exocytosis |
| 30 | -481.9659 | 1NRR | serine proteinase/receptor |

| ATOM OF ACTIVE SITE | ATOM TYPE OF LIGAND | INTENSITY OF INTERACTION | DISTANCE OF INTERACTION [Å] |
|---|---|---|---|
| CYS145 N | O.co2 | 100 | 2.70 |
| GLUの166 N | O.2 | 100 | 2.70 |
| THR190 N | O.3 | 100 | 2.70 |

FIG.86

| RANKING | ENERGY | PDB code | REMARKS |
|---|---|---|---|
| 1 | -1263.8870 | 1EAD | dihydrolipoamide acetyltransferase |
| 2 | -1260.8689 | 1F6M | oxidoreductase |
| 3 | -1147.1739 | 1JR4 | transferase |
| 4 | -1141.9917 | 1QF5 | ligase |
| 5 | -1104.9447 | 1JAY | structural genomics |
| 6 | -1019.3584 | 1KZL | transferase |
| 7 | -996.5865 | 1QF4 | ligase |
| 8 | -988.6588 | 1JIJ | ligase |
| 9 | -981.8594 | 8ICO | complex (nucleotidyltransferase/dna) |
| 10 | -953.0986 | 1LO9 | hydrolase |
| 11 | -949.1903 | 1JTU | transferase |
| 12 | -922.4795 | 1JKX | transferase |
| 13 | -918.4892 | 1JIL | ligase |
| 14 | -916.9950 | 1I95 | ribosome |
| 15 | -908.4880 | 1AL6 | lyase |
| 16 | -893.5862 | 1LKL | complex (tyrosine kinase/peptide) |
| 17 | -892.3713 | 1N37 | deoxyribonucleic acid |
| 18 | -887.9721 | 1LCB | transferase (methyltransferase) |
| 19 | -866.9600 | 1O9F | protein binding |
| 20 | -826.4893 | 1LO7 | hydrolase |
| 21 | -792.0254 | 4UAG | ligase |
| 22 | -776.9998 | 1EJB | transferase |
| 23 | -772.2400 | 1BFZ | n-terminal product peptide |
| 24 | -769.6844 | 1F9E | apoptosis |
| 25 | -762.5275 | 1TLP | hydrolase (metalloproteinase) |
| 26 | -759.8312 | 1QIN | lyase |
| 27 | -758.2140 | 1KO6 | transferase |
| 28 | -757.5526 | 1C0A | ligase/RNA |
| 29 | -755.7987 | 1QD1 | transferase |
| 30 | -755.1049 | 1LO8 | hydrolase |
| | | | |
| 49 | -639.1858 | 1UK4 | hydrolase |

FIG.87

| ATOM OF ACTIVE SITE | ATOM TYPE OF LIGAND | INTENSITY OF INTERACTION | DISTANCE OF INTERACTION [Å] |
|---|---|---|---|
| THR25  OG1 | N.am | 100 | 3.80 |
| CYS145  N | O.co2 | 100 | 2.70 |
| MET165  CG | C.3 | 100 | 4.00 |
| GLU166  N | O.2 | 100 | 2.70 |
| THR190  N | O.3 | 100 | 2.70 |

FIG.88

| RANKING | ENERGY | PDB code | REMARKS |
|---|---|---|---|
| 1 | -364.6548 | 1I95 | ribosome |
| 2 | -299.0166 | 1UK4 | hydrolase |
| 3 | -109.6867 | 1BXX | endocytosis/exocytosis |
| 4 | -93.0540 | 1KZL | transferase |
| 5 | -72.9399 | 1NKK | hydrolase |
| 6 | -10.7565 | 1F8H | endocytosis/exocytosis |
| 7 | -4.2756 | 1QTN | apoptosis |
| 8 | 162.1557 | 1KGQ | transferase |
| 9 | 163.2075 | 1O9F | protein binding |
| 10 | 331.8725 | 1CGL | metalloprotease |
| 11 | 370.5027 | 2BBQ | transferase(methyltransferase) |
| 12 | 397.8488 | 4DMR | oxidoreductase |
| 13 | 550.2598 | 1HPG | hydrolase (serine protease) |
| 14 | 716.6561 | 1LOC | lectin |
| 15 | 839.7398 | 1DMT | hydrolase |
| 16 | 848.7090 | 1KAP | zinc metalloprotease |
| 17 | 850.2630 | 1JG3 | transferase |
| 18 | 883.4400 | 1BC5 | complex (methyltransferase/peptide) |
| 19 | 905.9695 | 1FCH | signaling protein |
| 20 | 913.9769 | 1CF8 | catalytic antibody |
| 21 | 1088.2428 | 1NWE | hydrolase |
| 22 | 1089.3496 | 1KO6 | transferase |
| 23 | 1116.9042 | 1F74 | lyase |
| 24 | 1131.4783 | 1ING | hydrolase (o-glycosyl) |
| 25 | 1132.3648 | 1I31 | endocytosis/exocytosis |
| 26 | 1148.9063 | 1IAU | hydrolase |
| 27 | 1156.0335 | 1B48 | transferase |
| 28 | 1160.3512 | 1PTT | complex (hydrolase/peptide) |
| 29 | 1176.7814 | 1MC5 | oxidoreductase |
| 30 | 1197.3565 | 1F9E | apoptosis |

| ATOM OF ACTIVE SITE | ATOM TYPE OF LIGAND | INTENSITY OF INTERACTION | DISTANCE OF INTERACTION [Å] |
|---|---|---|---|
| CYS145  N | ACCEPTOR | 100 | 2.70 |
| MET165  CG | CARBON | 100 | 4.00 |
| GLU166  N | ACCEPTOR | 100 | 2.70 |
| THR190  N | ACCEPTOR | 100 | 2.70 |

FIG.91

| RANKING | ENERGY | PDB code | REMARKS |
|---|---|---|---|
| 1 | -2095.8588 | 1JJQ | hormone/growth factor |
| 2 | -2011.3626 | 2BVW | hydrolase |
| 3 | -1670.8384 | 1DOG | hydrolase |
| 4 | -1336.7960 | 1LWJ | transferase |
| 5 | -1320.0704 | 1KEU | lyase |
| 6 | -1230.0604 | 1GAH | hydrolase |
| 7 | -1214.9459 | 1I7E | signaling protein |
| 8 | -1195.8653 | 1C39 | signaling protein |
| 9 | -1191.3777 | 1BB5 | hydrolase |
| 10 | -1189.0253 | 2FHI | nucleotide-binding protein |
| 11 | -1147.9761 | 1GO6 | glycopeptide antibiotics |
| 12 | -1103.6272 | 1M4D | transferase |
| 13 | -1095.3050 | 1QHC | hydrolase |
| 14 | -1088.7299 | 1M2N | gene regulation |
| 15 | -1078.3684 | 1QGL | lectin (agglutinin) |
| 16 | -1056.4078 | 4ENG | glycosyl hydrolase |
| 17 | -1033.0227 | 1LON | ligase |
| 18 | -1031.2555 | 1MWL | ribonucleic acid |
| 19 | -1027.4239 | 1QPK | hydrolase |
| 20 | -1014.9817 | 1UDB | isomerase |
| 21 | -1005.1689 | 1GQC | transferase |
| 22 | -976.9293 | 1H6H | px domain |
| 23 | -975.2827 | 1LSP | hydrolase (o-glycosyl) |
| 24 | -973.5218 | 1FF1 | signaling protein |
| 25 | -963.4098 | 3UAG | ligase |
| 26 | -937.2165 | 1IBG | immunoglobulin |
| 27 | -933.6818 | 1DRV | oxidoreductase |
| 28 | -918.6947 | 2MBR | oxidoreductase |
| 29 | -917.1703 | 1NAB | deoxyribonucleic acid |
| 30 | -897.3026 | 1SLY | glycosyltransferase |
| | | | |
| 774 | 331.9928 | 1UK4 | hydrolase |

| ATOM OF ACTIVE SITE | ATOM TYPE OF LIGAND | INTENSITY OF INTERACTION | DISTANCE OF INTERACTION [Å] |
|---|---|---|---|
| CYS145  N | O.co2 | 100 | 2.70 |
| MET165  CG | C.3 | 100 | 4.00 |
| GLU166  N | O.2 | 100 | 2.70 |
| THR190  N | O.3 | 100 | 2.70 |

FIG.94

| RANKING | ENERGY | PDB code | REMARKS |
|---|---|---|---|
| 1 | -1047.3743 | 1KZL | transferase |
| 2 | -860.437 | 1J71 | hydrolase |
| 3 | -844.8737 | 3UAG | ligase |
| 4 | -837.6255 | 1LKL | complex (tyrosine kinase/peptide) |
| 5 | -829.8176 | 1QF4 | ligase |
| 6 | -732.2087 | 1A2N | transferase |
| 7 | -721.6213 | 1G1F | hydrolase, signaling protein |
| 8 | -698.5922 | 1F7B | lyase |
| 9 | -689.1472 | 1BFZ | n-terminal product peptide |
| 10 | -646.7943 | 148L | hydrolase(o-glycosyl) |
| 11 | -634.4654 | 1CGL | metalloprotease |
| 12 | -629.1673 | 1JIL | ligase |
| 13 | -616.8733 | 1FF1 | signaling protein |
| 14 | -611.1171 | 1F9E | apoptosis |
| 15 | -567.0738 | 1R1R | oxidoreductase |
| 16 | -554.5321 | 1I95 | ribosome |
| 17 | -547.2494 | 1FQX | hydrolase |
| 18 | -536.7069 | 1HCT | complex (signal transduction/peptide) |
| 19 | -531.1014 | 1SIA | mucin motif |
| 20 | -508.9899 | 1JIJ | ligase |
| 21 | -507.9655 | 1LSP | hydrolase (o-glycosyl) |
| 22 | -497.6341 | 1F8H | endocytosis/exocytosis |
| 23 | -492.3974 | 1F74 | lyase |
| 24 | -443.232 | 1QH5 | hydrolase |
| 25 | -427.5925 | 1JII | ligase |
| 26 | -417.4991 | 1JQY | toxin |
| 27 | -416.9956 | 2KCE | methyltransferase |
| 28 | -396.7898 | 1EJB | transferase |
| 29 | -387.6441 | 1MMJ | hydrolase |
| 30 | -358.2162 | 1SLY | glycosyltransferase |
| | | | |
| 39 | -245.9500 | 1UK4 | hydrolase |

FIG.95
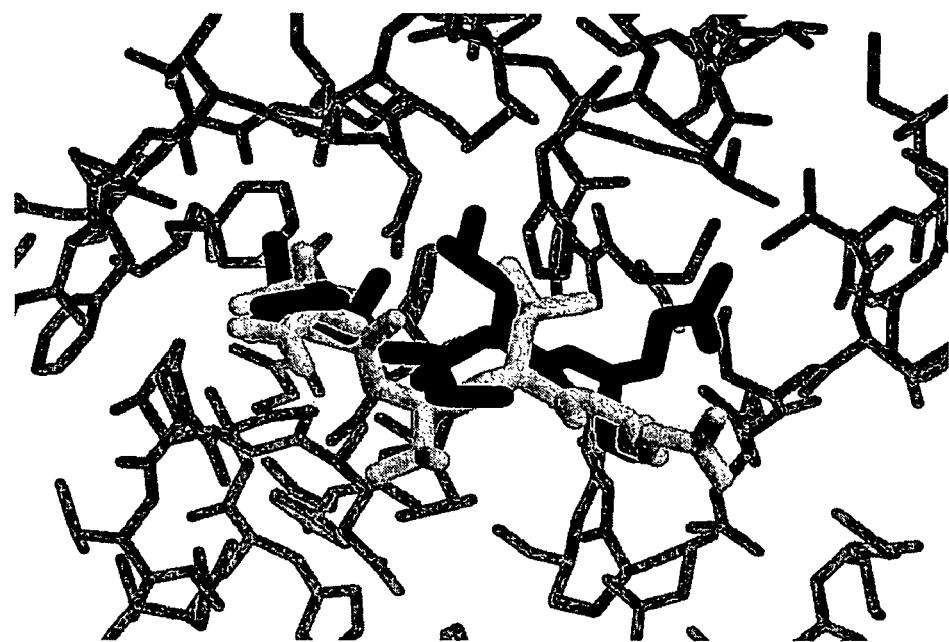
FIG.96
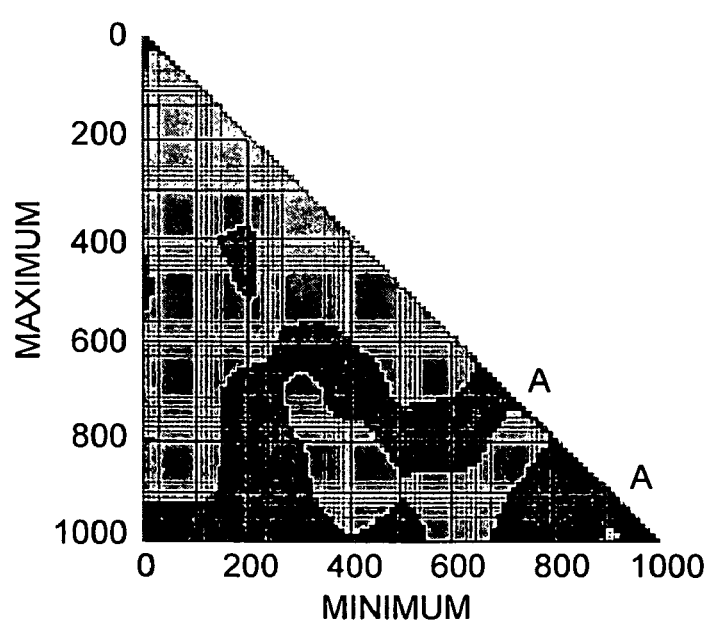

| ATOM OF ACTIVE SITE | ATOM TYPE OF LIGAND | INTENSITY OF INTERACTION | DISTANCE OF INTERACTION [Å] |
|---|---|---|---|
| LUE4    O | N.pl3 | 100 | 2.87 |
| ASP26  OD1 | N.ar | 300 | 3.00 |
| ASP26  OD2 | N.pl3 | 300 | 3.00 |

LIGAND SEARCHING DEVICE, LIGAND SEARCHING METHOD, PROGRAM, AND RECORDING MEDIUM

SEQUENCE LISTING

The instant application contains a Sequence Listing which has been submitted in ASCII format via EFS-Web and is hereby incorporated by reference in its entirety. Said ASCII copy, created on Oct. 13, 2010, is named 79880102.txt and is 9,115 bytes in size.

TECHNICAL FIELD

The present invention relates to ligand screening apparatuses, ligand screening methods, programs and a recording medium using protein 3D structure coordinates, and more specifically to a ligand screening apparatus, a ligand screening method, a program and a recording medium for predicting a ligand that is considered as being involved in an interaction, for a protein having known 3D structure coordinates.

BACKGROUND ART

Proteins required for maintenance of biological functions such as enzymes and receptors have properties called "substrate specificity", and such proteins are classified into "Lock&Key" type wherein an active site constantly remains unchanged to details of structure of substrate molecule, and "Induced-Fit" (induced-bonding) type wherein an active site is in a random inactive state in the absence of a substrate, and the active site changes into an active state in the presence of a substrate for capturing the coming substrate. By the term induced-fit type, such a receptor is contemplated that the 3D structure of a ligand binding site changes in binding with a ligand to allow intake of the ligand.

As a computational chemical technique for screening for ligand molecules using a 3D structure of a protein, 3D compound database screening (Virtual Screening) as reported in AutoDocK ("Morris, G. M. Goodsell, D. S. Halliday, R. S. Huey, R. Hart, W. E. Belew, R. K. Olson, A. J. (1998) Automated docking using a Lamarckian genetic algorithm and an empirical biding free energy function. J. Comput. Chem. 19:1639-1662; Goodsell, D. S. Morris, G. M. Olson, A. J. (1996) Automated docking of flexible ligands: applications of AutoDock. J. Mol. Recognit, 9: 1-5"), DOCK ("Ewing, T. J. I Makino, S. Skillman, A. G. Kuntz I. D. (2001) DOCK 4.0: search strategies for automated molecular docking of flexible molecule databases. J. Comput. Aided Mol. Des. 15: 411-28"), FlexX ("Rarey, M, Kramer, B, Lengauer, T, Klebe G. (1996) A fast flexible docking method using an incremental construction algorithm. J. Mol. Biol. 261: 470-89; Rarey, M. Wefing, S. Lengauer, T. (1996) Placement of medium-sized molecular fragments into active sites of proteins. J. Comput. Aided Mol. Des. 10: 41-54"), GOLD ("Jones, G. Willett, P. Glen, R. C. (1995) Molecular recognition of receptor sites using a genetic algorithm with a description of desolvation. J. Mol. Biol. 245:43-53; Jones, G. Willett, P. Glen, R. C, Leach, A. R. Taylor, R. (1997) Development and validation of a genetic algorithm for flexible docking. J. Mol. Biol. 267: 727-48"), ADAM&EVE ("Mizutani, M. Y. Itai, A. (2004) Efficient method for high-throughput virtual screening based on flexible docking: discovery of novel acetylcholinesterase inhibitors. J. Med. Chem. 47: 4818-4828") are known. These are also called "High-performance docking study" and enable a mass-scale compound library screening. However, the ability of these techniques to predict binding conformation and binding energy is poor because rough approximation is used for evaluation. In addition, since they fail to consider computational expression parameters corresponding to "induced-binding" which is very important for binding between a protein and a ligand, and even if such consideration is made, it is to such an extent that random numbers are generated and side chains of receptor are moved, and accuracy of the computation result is not sufficient.

As a method for simulating "induced-binding" which is important for binding between protein and ligand, MD (molecular dynamic calculation), MM (molecular mechanical calculation), and MC (Monte Carlo method) are known. These methods provide relatively high accuracy, and enable prediction of binding conformation and binding energy. Here, the technique called "molecular dynamic method (MD)" calculates dynamic structure of a molecule by sequentially solving dynamic equation based on the classical dynamics for each atom constituting the molecule, and enables the simulation of dynamic behavior of a protein with high accuracy. However, it is not necessarily a useful means because it requires significant time for calculation and has difficulty in handling many molecules. Further, molecular dynamic calculation executed for a target protein according to such a conventional method results in a protein 3D structure whose coordinates are largely different from those analyzed by X-ray, NMR and the like. Although such a difference includes a physicochemical description of dynamic behavior of a protein, it sometimes behaves contradictorily to an experimental result of dynamic behavior proved by NMR or the like, and hence it often fails to provide an accurate simulation result.

As described above, in respect of the conventional "in silico screening", since computational expression parameters corresponding to "induced-binding" which is very important for binding between protein and ligand are not sufficiently considered, it does not deem that the accuracy of the calculation result is adequate.

On the other hand, in molecular simulation, it is possible to express and analyze the above induced-binding; however, significant time is required for obtaining an accurate result. Many results will be influenced by the initial structure coordinates.

Inventors of the present invention examined the way of screening for a ligand that will bind to a target protein when the 3D structure of a certain protein is given. As described above, some currently available receptor-ligand binding analyzing software takes flexibility of a ligand into account, but most of such software fails to consider flexibility of a receptor. Even though there is software that considers flexibility of a receptor, such consideration just moves a side chain of the receptor by generation of random numbers, and most of the software are dedicated to a Lock&Key type receptor. In such circumstances, we attempted to develop receptor-ligand binding analyzing software dedicated to an Induced-Fit type receptor.

The problem to be solved by the present invention is to provide a ligand screening apparatus, a ligand screening method, a program and a recording medium capable of screening for a ligand that binds to a certain protein which is a particularly important key to development of agricultural chemicals and pharmaceuticals and the like, with significantly higher efficiency and accuracy than conventional methods. It is also an object to provide a ligand screening apparatus, a ligand screening method, a program and a recording medium which carry out various modifications of ligand molecules and modifications of proteins such as receptors rapidly and effectively. It is also an object of the present invention to clarify a mode of interaction between a ligand and a protein and make the recognition mechanism of the interaction clear, thereby identifying a cause of disease, and promoting development of related drugs.

DISCLOSURE OF INVENTION

Inventors of the present invention diligently examined the method of screening for a ligand that binds to a target protein when any 3D structure of such a protein is given, and finally established a ligand screening apparatus, a ligand screening method, a computer program and a recording medium as will be described later.

Here a procedure called "molecular dynamic method (MD)" is used which calculates dynamic structure of a molecule by sequentially solving a dynamic equation based on the classical dynamics for each atom constituting the molecule. In other words, this procedure calculates dynamic behavior based on classic dynamics in each atom constituting a certain molecule. Therefore, if one can employ this procedure successfully, even when an induced-fit type receptor in a state that no ligand is captured is selected as an initial state, binding between the receptor and a ligand could be reconstructed. Since the MD calculation is based on the classic dynamics, it is necessary to impose certain degree of constraint to each atom. For this reason, in our developing procedure, normal mode vibration (hereinafter "normal mode") of a receptor is first analyzed to calculate fluctuation of a dihedral angle of a main chain of the receptor, and then the MD calculation is conducted while imposing a constraint on each atom based on the calculated fluctuation of a dihedral angle of main chain. To be more specific, first, analysis and calculation of a normal mode are conducted, and then fluctuation of a dihedral angle of main chain in a steady state is calculated. Then by carrying out molecular dynamic calculation while imposing a constraint on each atom based on the fluctuation, a dynamic structure of the receptor is predicted more accurately. By using the dynamic structure obtained in the molecular dynamic calculation and an interaction function, a receptor/ligand binding which is also applicable to an induced-fit type receptor is predicted with high accuracy. In brief, the present invention predicts receptor/ligand binding more realistically with high accuracy. Therefore, the present invention is very useful for designing pharmaceuticals and agricultural chemicals.

To solve the objectives described above, a ligand screening apparatus according to a present invention is a ligand screening apparatus which screens for a ligand that binds to a protein when coordinate data of the protein of single chain or plural chains is given, the apparatus including: a post-structural-change protein coordinate data selecting unit that effects structural change in consideration of dynamic behavior using induced-fit parameter reflecting induced fit on the coordinate data of the protein and selects post-structural-change protein coordinate data; a spatial point designating unit that designates a spatial point at which superposition with the ligand is to be conducted, from the post-structural-change protein coordinate data selected by the post-structural-change protein coordinate data selecting unit; an interaction function calculating unit that calculates an interaction function when the protein and the ligand bind to each other using the spatial point designated by the spatial point designating unit and a ligand coordinate data of the ligand; and a ligand evaluating unit that evaluates the ligand that binds to the protein based on the interaction function calculated by the interaction function calculating unit.

The ligand screening apparatus according to another aspect of the present invention is the ligand screening apparatus, wherein the interaction function calculating unit calculates the interaction function using Score (i,j) shown in Formula 1.

$$Sscore(i, j) = \sum_{ij}^{\lambda} \begin{bmatrix} \text{when } i \text{ is not equal to } j \\ \alpha \times [\exp\{-(d_{ij}^s - d_{ij}^c)^2\} - \beta] \Big/ \frac{(d_{ij}^s + d_{ij}^c)^2}{2} \\ \text{when } i \text{ is equal to } j \\ \alpha \times (1 - \beta) \end{bmatrix}$$ [Formula 1]

(wherein $d_{ij}^s$ is a distance between i-th spatial point and j-th spatial point in the target protein. $d_{ij}^C$ is an interatomic distance between i-th atom and j-th atom in the compound. $\alpha$ is a coefficient for making Sscore(i,j) the maximum value when the group of spatial points in the target protein and the compound completely overlap with each other. $\beta$ is a coefficient for giving a threshold value by which it can be defined as "overlapping")

The ligand screening apparatus according to another aspect of the present invention is the ligand screening apparatus, wherein the interaction function calculating unit further includes an interaction function optimizing unit that carries out optimization so as to make the score of interaction function maximum.

The ligand screening apparatus according to another aspect of the present invention is the ligand screening apparatus, wherein the interaction function calculating unit further includes: an interaction energy optimizing unit that calculates interaction energy with the protein for the superposed ligand after optimization of the interaction function by the interaction function optimizing unit, and optimizes the interaction energy while finely adjusting conformation of ligand 3D structure data.

The ligand screening apparatus according to another aspect of the present invention is the ligand screening apparatus, wherein the ligand evaluating unit further includes: a reevaluating unit that executes the interaction function calculating unit after largely changing conformation of ligand 3D structure data following optimization by the interaction energy optimizing unit, and reevaluates the ligand that binds to the protein based on the interaction function calculated by the interaction function calculating unit.

The ligand screening apparatus according to another aspect of the present invention is the ligand screening apparatus, wherein in calculation of any one of the induced-fit parameters and the post-structural-change protein coordinate data or both, the post-structural-change protein coordinate data selecting unit calculates normal mode for the protein coordinate data, determines intensity of fluctuation of each amino acid, and conducts a molecular dynamic calculation using the intensity of fluctuation as a constraint condition.

The ligand screening apparatus according to another aspect of the present invention is the ligand screening apparatus, wherein the post-structural-change protein coordinate data selecting unit calculates a fluctuation value of a dihedral angle of the main chain according to normal mode calculation, and conducts molecular dynamic calculation while setting the fluctuation value as a coefficient of force K in the molecular dynamic calculation shown by Formula 2 or Formula 3.

$$Erot = Krot(\phi - \phi 0)^2$$ [Formula 2]

(wherein Erot represents energy of a dihedral angle of main a chain atom in a 3D structure of a protein. $\phi$ represents a dihedral angle of the main chain atoms. φ0 represents a standard value of a dihedral angle of the main chain atoms. Here, when a value of Krot is large, φ is constrained by φ0.)

$$Epos = Kpos(r-r0)^2 \qquad \text{[Formula 3]}$$

(wherein Epos represents position energy of a main chain atom in a 3D structure of a protein. r represents a coordinate of main chain atom. r0 represents the standard value of coordinate of main chain atom. Here, when a value of Kpos is large, r is constrained by r0.)

The ligand screening apparatus according to another aspect of the present invention is the ligand screening apparatus, wherein the interaction function calculating unit uses the interaction function to which a dynamic property function representing dynamic property of a protein is added as "elastic energy".

The ligand screening apparatus according to another aspect of the present invention is the ligand screening apparatus, wherein the interaction function calculating unit adapts "U collision" as "elastic energy" which is a function shown by Formula 4 in consideration of local flexibility of protein.

$$U_{collision} = \sum_{i=1}^{M} \sum_{j=1}^{N} \varphi(i,j) \qquad \text{[Formula 4]}$$

$$\varphi(i,j) = K\,collision * (R\,collision(i,j) - R)^2$$

(wherein M is the number of atoms in an active site that prohibit collision, N is the number of atoms of a ligand. When interatomic distance R between an i-th atom of a main chain or a side chain with a little dynamic behavior in active site, and the j-th atom in the ligand is not more than collision distance "Rcollision(i,j)", φ(i,j) is calculated)

The ligand screening apparatus according to another aspect of the present invention is the ligand screening apparatus, wherein the interaction function calculating unit uses the interaction function to which a normal mode analysis result or secondary structure determination result of the protein is added as a dynamic property function that represents a dynamic property of a protein.

A ligand screening method according to the present invention is the ligand screening method which screens for a ligand that binds to a protein when coordinate data of the protein of single chain or plural chains is given, the method including: a post-structural-change protein coordinate data selecting step that effects structural change in consideration of dynamic behavior using induced-fit parameter reflecting induced fit on the coordinate data of the protein and selects post-structural-change protein coordinate data; a spatial point designating step that designates a spatial point at which superposition with the ligand is to be conducted, from the post-structural-change protein coordinate data selected by the post-structural-change protein coordinate data selecting step; interaction function calculating step that calculates an interaction function when the protein and the ligand bind to each other using the spatial point designated by the spatial point designating step and a ligand coordinate data of the ligand; and a ligand evaluating step that evaluates the ligand that binds to the protein based on the interaction function calculated by the interaction function calculating step.

The ligand screening method according to another aspect of the present invention is the ligand screening method, wherein the interaction function calculating step calculates the interaction function using Score (i,j) shown in Formula 1.

$$Sscore(i,j) = \sum_{ij}^{\lambda} \begin{bmatrix} \text{when } i \text{ is not equal to } j \\ \alpha \times [\exp\{-(d_{ij}^s - d_{ij}^c)^2\} - \beta] \Big/ \frac{(d_{ij}^s + d_{ij}^c)^2}{2} \\ \text{when } i \text{ is equal to } j \\ \alpha \times (1 - \beta) \end{bmatrix} \qquad \text{[Formula 1]}$$

(wherein $d_{ij}^s$ is a distance between i-th spatial point and j-th spatial point in the target protein. $d_{ij}^C$ is an interatomic distance between i-th atom and j-th atom in the compound. α is a coefficient for making Sscore(i,j) the maximum value when the group of spatial points in the target protein and the compound completely overlap with each other. β is a coefficient for giving a threshold value by which it can be defined as "overlapping")

The ligand screening method according to another aspect of the present invention is the ligand screening method, wherein the interaction function calculating step further includes an interaction function optimizing step that carries out optimization so as to make the score of interaction function maximum.

The ligand screening method according to another aspect of the present invention is the ligand screening method, wherein the interaction function calculating step further includes: interaction energy optimizing step that calculates interaction energy with the protein for the superposed ligand after optimization of the interaction function by the interaction function optimizing step, and optimizes the interaction energy while finely adjusting conformation of ligand 3D structure data.

The ligand screening method according to another aspect of the present invention is the ligand screening method, wherein the ligand evaluating step further includes: a reevaluating step that executes the interaction function calculating step after largely changing conformation of the ligand 3D structure data following optimization by the interaction energy optimizing step, and reevaluates the ligand that binds to the protein based on the interaction function calculated by the interaction function calculating step.

The ligand screening method according to another aspect of the present invention is the ligand screening method, wherein in calculation of any one of the induced-fit parameter and the post-structural-change protein coordinate data or both, the post-structural-change protein coordinate data selecting step calculates normal mode for the protein coordinate data, determines intensity of fluctuation of each amino acid, and conduct molecular dynamic calculation using the intensity of fluctuation as a constraint condition.

The ligand screening method according to another aspect of the present invention is the ligand screening method, wherein the post-structural-change protein coordinate data selecting step calculates a fluctuation value of a dihedral angle of a main chain according to a normal mode calculation, and conducts molecular dynamic calculation while setting the fluctuation value as a coefficient of force K in the molecular dynamic calculation shown by Formula 2 or Formula 3.

$$Erot = Krot(\phi - \phi 0)^2 \qquad \text{[Formula 2]}$$

(wherein Erot represents energy of a dihedral angle of a main chain atom in 3D structure of a protein. φ represents a dihedral angle of a main chain atom. φ0 represents a standard value of a dihedral angle of a main chain atom. Here, when a value of Krot is large, φ is constrained by φ0.)

$$Epos = Kpos(r-r0)^2 \qquad \text{[Formula 3]}$$

(wherein Epos represents position energy of main chain atom in 3D structure of a protein. r represents coordinate of main chain atom. r0 represents standard value of coordinate of main chain atom. Here, when a value of Kpos is large, r is constrained by r0.)

The ligand screening method according to another aspect of the present invention is the ligand screening method, wherein the interaction function calculating step uses the interaction function to which a dynamic property function representing dynamic property of protein is added as "elastic energy".

The ligand screening method according to another aspect of the present invention is the ligand screening method, wherein the interaction function calculating step adapts "U collision" as "elastic energy" which is a function shown by Formula 4 in consideration of local flexibility of protein.

$$U_{collision} = \sum_{i=1}^{M}\sum_{j=1}^{N} \varphi(i,j)$$ [Formula 4]

$$\varphi(i,j) = K \text{ collision} * (R \text{ collision}(i,j) - R)^2$$

(wherein M is the number of atoms in an active site that prohibit collision, N is the number of atoms of a ligand. When interatomic distance R between an i-th atom of a main chain or a side chain with a little dynamic behavior in an active site, and j-th atom in the ligand is not more than collision distance "Rcollision(i,j)", φ(i,j) is calculated)

The ligand screening method according to another aspect of the present invention is the ligand screening method, wherein the interaction function calculating step uses the interaction function to which a normal mode analysis result or secondary structure determination result of the protein is added as a dynamic property function that represents dynamic property of a protein.

A program according to the present invention is a program which makes a computer execute a ligand screening method which screens for a ligand that binds to a protein when coordinate data of the protein of single chain or plural chains is given, the method including: a post-structural-change protein coordinate data selecting step that effects structural change in consideration of dynamic behavior using induced-fit parameter reflecting induced fit on the coordinate data of protein and selects post-structural-change protein coordinate data; a spatial point designating step that designates a spatial point at which superposition with the ligand is to be conducted, from the post-structural-change protein coordinate data selected by the post-structural-change protein coordinate data selecting step; an interaction function calculating step that calculates an interaction function when the protein and the ligand bind to each other using the spatial point designated by the spatial point designating step and a ligand coordinate data of the ligand; and a ligand evaluating step that evaluates the ligand that binds to the protein based on the interaction function calculated by the interaction function calculating step.

The program according to another aspect of the present invention is the program, wherein the interaction function calculating step calculates the interaction function using Score (i,j) shown in Formula 1.

$$Sscore(i,j) = \sum_{ij}^{\lambda} \begin{bmatrix} \text{when } i \text{ is not equal to } j \\ \alpha \times [\exp\{-(d_{ij}^s - d_{ij}^c)^2\} - \beta] / \frac{(d_{ij}^s + d_{ij}^c)^2}{2} \\ \text{when } i \text{ is equal to } j \\ \alpha \times (1-\beta) \end{bmatrix}$$ [Formula 1]

(wherein $d_{ij}^s$ is a distance between i-th spatial point and j-th spatial point in the target protein. $d_{ij}^C$ is an interatomic distance between i-th atom and j-th atom in the compound. α is a coefficient for making Sscore(i,j) the maximum value when the group of spatial points in the target protein and the compound completely overlap with each other. β is a coefficient for giving a threshold value by which it can be defined as "overlapping")

The program according to another aspect of the present invention is the program, wherein the interaction function calculating step further includes an interaction function optimizing step that carries out optimization so as to make the score of interaction function maximum.

The program according to another aspect of the present invention is the program, wherein the interaction function calculating step further includes: an interaction energy optimizing step that calculates interaction energy with the protein for the superposed ligand after optimization of the interaction function by the interaction function optimizing step, and optimizes the interaction energy while finely adjusting conformation of ligand 3D structure data.

The program according to another aspect of the present invention is the program, wherein the ligand evaluating step further includes: a reevaluating step that executes the interaction function calculating step after largely changing conformation of the ligand 3D structure data following optimization by the interaction energy optimizing step, and reevaluates the ligand that binds to the protein based on the interaction function calculated by the interaction function calculating step.

The program according to another aspect of the present invention is the program, wherein in calculation of any one of the induced-fit parameter and the post-structural-change protein coordinate data or both, the post-structural-change protein coordinate data selecting step calculates normal mode for the protein coordinate data, determines intensity of fluctuation of each amino acid, and conducts a molecular dynamic calculation using the intensity of the fluctuation as a constraint condition.

The program according to another aspect of the present invention is the program, wherein the post-structural-change protein coordinate data selecting step calculates a fluctuation value of a dihedral angle of a main chain according to a normal mode calculation, and conducts a molecular dynamic calculation while setting the fluctuation value as a coefficient of force K in the molecular dynamic calculation shown by Formula 2 or Formula 3.

$$Erot = Krot(\phi - \phi 0)^2$$ [Formula 2]

(wherein Erot represents energy of dihedral angle of main chain atom in 3D structure of a protein. φ represents dihedral angle of main chain atom. φ0 represents standard value of dihedral angle of main chain atom. Here, when a value of Krot is large, φ is constrained by φ0.)

$$Epos = Kpos(r - r0)^2$$ [Formula 3]

(wherein Epos represents position energy of main chain atom in 3D structure of a protein. r represents coordinate of main chain atom. r0 represents standard value of coordinate of main chain atom. Here, when a value of Kpos is large, r is constrained by r0.)

The program according to another aspect of the present invention is the program, wherein the interaction function calculating step uses the interaction function to which a dynamic property function representing dynamic property of protein is added as "elastic energy".

The program according to another aspect of the present invention is the program, wherein the interaction function calculating step adapts "U collision" as "elastic energy" which is a function shown by Formula 4 in consideration of local flexibility of the protein.

$$U_{collision} = \sum_{i=1}^{M} \sum_{j=1}^{N} \varphi(i, j)$$ [Formula 4]

$$\varphi(i, j) = K \text{ collision} * (R \text{ collision}(i, j) - R)^2$$

(wherein M is a number of atoms in an active site that prohibit collision, N is a number of atoms of a ligand. When interatomic distance R between an i-th atom of a main chain or a side chain with a little dynamic behavior in an active site, and a j-th atom in the ligand is not more than collision distance "Rcollision(i,j)", φ(i,j) is calculated)

The program according to another aspect of the present invention is the program, wherein the interaction function calculating step uses the interaction function to which a normal mode analysis result or secondary structure determination result of the protein is added as a dynamic property function that represents dynamic property of protein.

A computer readable recording medium according to the present invention is the computer readable recording medium in which the program according to the present invention is recorded.

BRIEF DESCRIPTION OF DRAWINGS

FIG. 12 is a view showing a result of comparison between parameters of MD and clustering and scores;
FIG. 17 is a view showing distribution of dihedral angle constraint parameters at a fixed clustering parameter;
FIG. 18 shows distribution of dihedral angle constraint parameters at a fixed clustering parameter;
FIG. 22 is a view showing alignment of 1CBQ ("1CBQ" sequence disclosed as SEQ ID NO: 1 and "1ICM" sequence disclosed as SEQ ID NO: 2);
FIG. 25 is a view showing difference between an X-ray structure and a model structure of 1CBQ by rms;
FIG. 29 is a view showing alignment of 1J9G ("1J9G" sequence disclosed as SEQ ID NO: 3 and "1AHN" sequence disclosed as SEQ ID NO: 4);
FIG. 32 is a view showing difference between an X-ray structure and a model structure of 1J9G by rms;
FIG. 36 is a view showing alignment of 1MMB ("1MMB" sequence disclosed as SEQ ID NO: 5 and "1B3D_A" sequence disclosed as SEQ ID NO: 6);
FIG. 39 is a view showing difference between an X-ray structure and a model structure of 1MMB by rms.

FIG. 46 is a view showing structure-activity relationship information obtained from 1LUD (MODEL 4);

FIG. 47 is a view showing a result of active site-ligand binding analysis in 1BZF (MODEL 18);

FIG. 54 is a view showing structure-activity relationship information obtained from 1YER;

FIG. 55 is a view showing a result of active site-ligand binding analysis in 1YER;

FIG. 61 is a view showing structure-activity relationship information obtained from 1OUK;

FIG. 62 is a view showing a result of active site-ligand binding analysis in 1A9U;

FIG. 67 is a view showing a result of in silico screening;

FIG. 80 is a view showing a result of in silico screening in 1UK3 (B chain);

FIG. 86 is a view showing a result of in silico screening executed while designating three positions in SAR;

FIG. 87 is a view showing structure-activity relationship information obtained from 1UK3 (B chain);

FIG. 88 is a view showing a result of high throughput screening executed while designating five positions in SAR;

FIG. 91 is a view showing a result of high throughput screening executed while changing the designated ligand atom type;

FIG. 94 is a view showing a result of high throughput screening executed with fixed receptor;

FIG. 95 is a view showing a result of comparison between a ligand in which 1UK3 and 1UK4 are superposed, and a ligand of screening result;

FIG. 96 is a view showing distribution of dihedral angle constraint MD parameters in 1AXJ;

BEST MODE(S) FOR CARRYING OUT THE INVENTION

Exemplary embodiments of a ligand screening apparatus, a ligand screening method, a program and a recording medium of the present invention will be explained in detail with reference to the attached drawings. It is to be noted that the present invention is not limited to these exemplary embodiments.

Several terms used herein have the following meanings unless otherwise specified.

The term "target protein" means a protein whose precise 3D structure is already determined by X-ray crystallographic analysis, NMR analysis or a homology modeling method and which is an object of ligand screening.

The term "atomic coordinate" describes a 3D structure in 3D space. It includes relative distances from the origin of a certain spatial point in three directions which are perpendicular to each other, and hence an atomic coordinate is described by a vector comprising three numbers per each atom existing in a protein except for hydrogen atoms.

[Basic Principal of the Present Invention]

Figure 1:
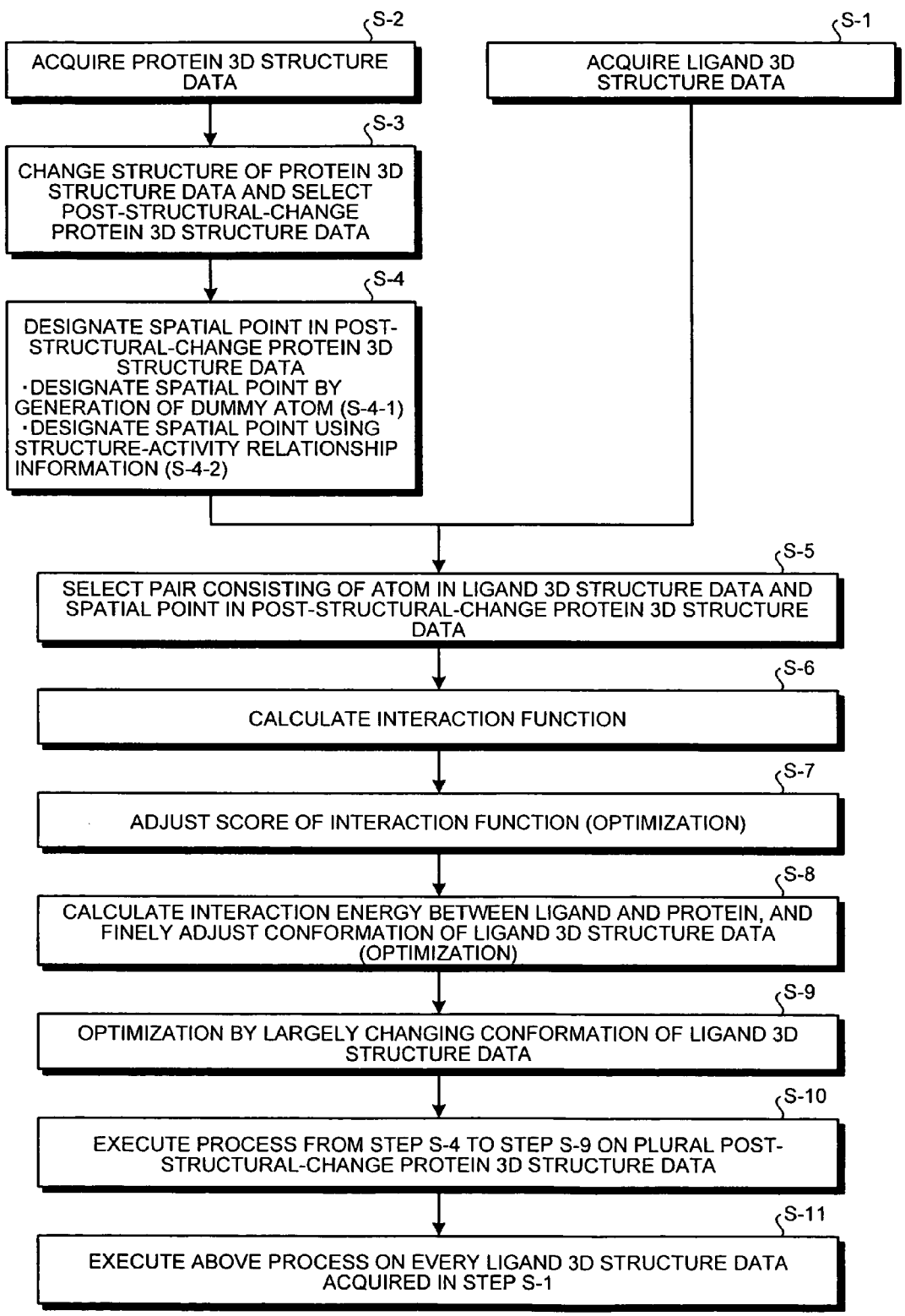
FIG. 1 is a conceptual view showing a basic principle of the present invention.

The basic principal of the present invention will now be explained with reference to FIG. 1. FIG. 1 is a conceptual diagram showing the basic principal of the present invention. The present invention relates to a ligand screening apparatus, a ligand screening method, a computer program and a recording medium, wherein when a protein 3D structure consisting of a single chain or plural chains is given, a parameter reflecting induced-fit from the given 3D structure of the target protein and a 3D structure coordinate after structural change are calculated in advance by e.g., a normal mode calculating method or molecular dynamic calculating method; an interaction function in the binding of the target protein and other substance (ligand) is defined using the parameter and the 3D structure coordinate after structural change; and a substance (ligand) which binds to the target protein is evaluated and chosen by the interaction function.

In the present invention, first, one ligand is selected from a compound database, and 3D structure data of the ligand is acquired (Step S-1). Also 3D structure data of a target protein is acquired (Step S-2).

Then in the present invention, based on the 3D structure data of the protein, structural change considering dynamic behavior is conducted using an induced-fit parameter reflecting induced-fit, to prepare plural sets of protein coordinate data after structural change (hereinafter referred to as "post-structural-change protein coordinate data"), and one set of post-structural-change protein coordinate data is randomly chosen (Step S-3).

Next, in the present invention, a spatial point in the post-structural-change protein coordinate data to which the ligand is to be superposed is designated (Step S-4). The spatial point may be designated, for example, by the methods (1) and (2) as will be described below.

(1) Designation of Spatial Point by Generation of Dummy Atom (Step S-4-1)

Focusing on a hydrogen bond in interaction between ligand and protein, a hydrogen bond site in the protein is designated as a spatial point. The important issues in a hydrogen bond are distance and angle. That is, a hydrogen bond donor (hereinafter referred to as "donor") is required for calculating an angle.

In the present invention, when there is no hydrogen atom in an active site and the ligand, a dummy hydrogen atom is generated in accordance with the following rule.

Figure 2:
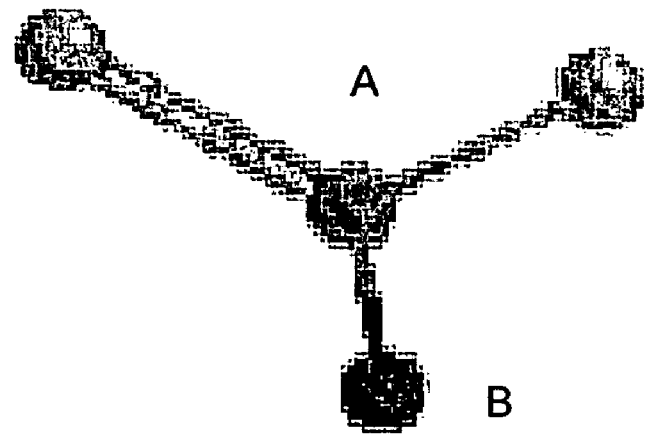
FIG. 2 is a view showing a dummy hydrogen atom in the sp² orbital.

1) A dummy atom is generated in an equilateral triangle centered at a $sp^2$ orbital atom (FIG. 2). More specifically, as shown in FIG. 2, a dummy hydrogen atom (B) is generated at a free position in the equilateral triangle centered at the nitrogen atom (A) of a $sp^2$ orbital atom.

2) As to a $sp^3$ orbital atom, when it is at a distance to form a hydrogen bond, it is deemed to turn so as to share the hydrogen atom, so that only the distance is considered in calculation of hydrogen bond interaction. Therefore, no dummy atom is generated for the $sp^3$ orbital atom.

As to metal and water, since they can mediate binding between active site and ligand binding, a dummy atom is generated at an interacting position in the manner as described below.

Figure 3:
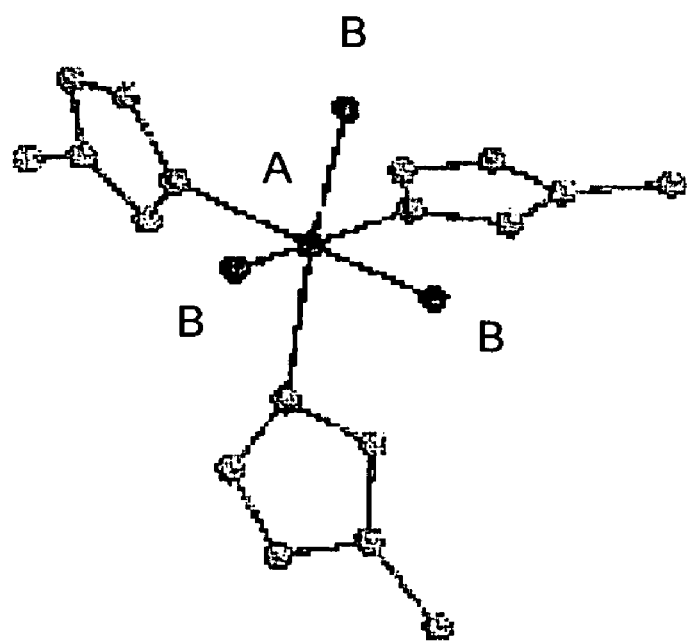
FIG. 3 is a view showing a dummy atom in a metal atom.

1) To metal such as iron, dummy atoms are generated in a regular octahedron (FIG. 3). That is, as shown in FIG. 3, dummy atoms (B) are generated at free positions in the regular octahedron centered at zinc (A).

2) To water, dummy atoms are generated in a regular tetrahedral. It is not necessary to generate a dummy atom in the direction in which it interacts with an active site.

(2) Designation of Spatial Point Using Structure-Activity Relationship Information (Step S-4-2)

Also in the present invention, a spatial point is designated by inputting information of the following items (A) to (D) in focus of structure-activity relationship (SAR) information of ligand.

(A) Atom of active site obtained form SAR information (hereinafter referred to as "A atom"). It follows PDB format.

(B) Atom type of ligand which is expected to interact with "A atom" (hereinafter referred as "B type"). It follows MOL2 format of SYBYL.

(C) Intensity of interaction between "A atom" and "B type" (hereinafter referred to as "C intensity").

(D) Distance of interaction between "A atom" and "B type" (hereinafter referred to as "D distance") (unit: angstrom).

In the present invention, a spatial point may be created according to the rules shown 1) to 4) below based on the input information (A) to (D) and using an initial coordinate of ligand in an active site of protein.

Figure 4:
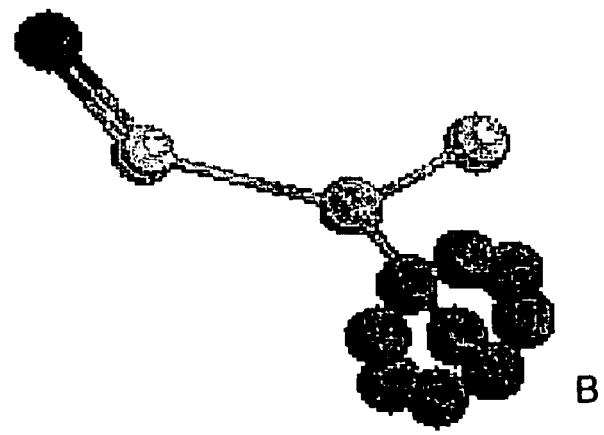
FIG. 4 is a view showing an initial coordinate (B) for docking a ligand into an active site based on structure-activity relationship (SAR) information.
Figure 5:
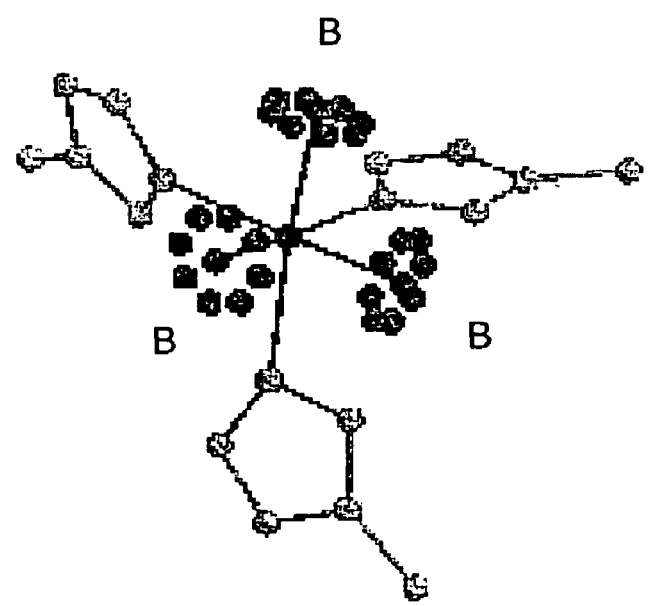
FIG. 5 is a view showing an initial coordinate (B) for docking a ligand into an active site based on structure-activity relationship (SAR) information.

1) When "A atom" is donor or metal and water (when designation of SAR information on the active side end is hydrogen bond donor or metal atom), a point and a circumference at "D distance" from "A atom" with respect to the direction of dummy atoms generated in Step S-4-1 are selected as initial coordinates (FIG. 4 and FIG. 5).

Figure 6:
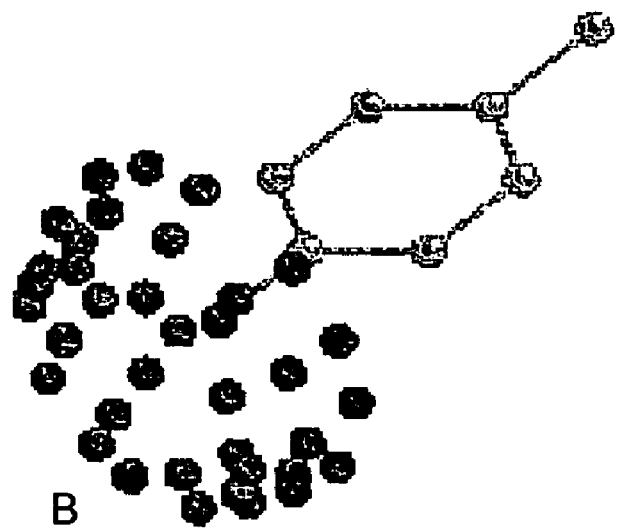
FIG. 6 is a view showing an initial coordinate (B) for docking a ligand into an active site based on structure-activity relationship (SAR) information.

2) When "A atom" is a $sp^3$ orbital atom (when designation of SAR information on the active site end is a $sp^3$ orbital atom), a circumference at "D distance" from "A atom" is selected as an initial coordinate (FIG. 6).

Figure 7:
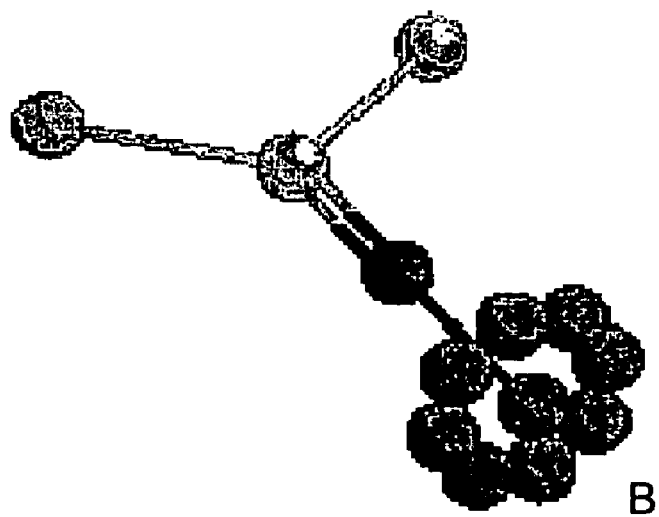
FIG. 7 is a view showing an initial coordinate (B) for docking a ligand into an active site based on structure-activity relationship (SAR) information.

3) When "A atom" is a hydrogen bond acceptor (hereinafter referred to as "acceptor") (when designation of SAR information on the active site end is a hydrogen bond acceptor), a position and a circumference at "D distance" on a bonding extension of "A atom" are selected as initial coordinates (FIG. 7).

Figure 8:
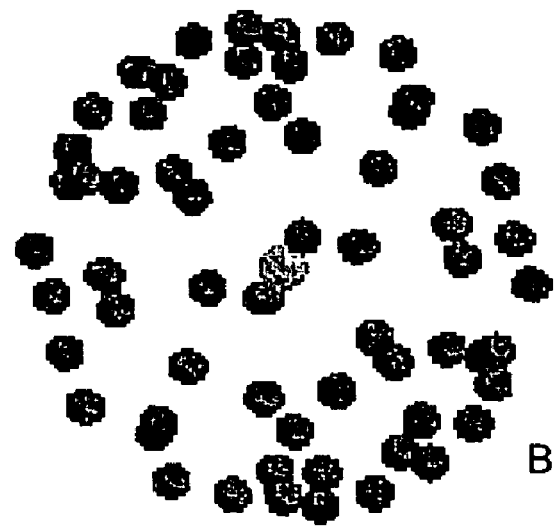
FIG. 8 is a view showing an initial coordinate (B) for docking a ligand into an active site based on structure-activity relationship (SAR) information.

4) In other cases (when designation of SAR information on the active site end is an atom other than the above), a point on the surface of a sphere centered at "A atom" and having a radius of "D distance" is selected as an initial coordinate (FIG. 8).

Here in contrast with the above 1) to 4), an initial coordinate of a ligand may be designated directly.

Returning again to FIG. 1, in the present invention, pairs of an atom in the ligand coordinate data selected in Step S-1 and a spatial point in the protein coordinate data designated in Step S-4 are randomly selected so that they are not overlapped with each other (Step S-5).

Then in the present invention, a score Sscore(i,j) which is an interaction function represented by the following formula 1 is calculated (Step S-6).

$$Sscore(i, j) = \sum_{ij}^{\lambda} \begin{bmatrix} \text{when } i \text{ is not equal to } j \\ \alpha \times [\exp\{-(d_{ij}^s - d_{ij}^c)^2\} - \beta] \Big/ \frac{(d_{ij}^s + d_{ij}^c)^2}{2} \\ \text{when } i \text{ is equal to } j \\ \alpha \times (1 - \beta) \end{bmatrix}$$

Here, $d_{ij}^s$ is a distance between i-th spatial point and j-th spatial point in the target protein. $d_{ij}^C$ is an interatomic distance between i-th atom and j-th atom in the compound. $\alpha$ is a coefficient for making Sscore(i,j) the maximum value when the group of spatial points in the target protein and the compound completely overlap with each other. $\beta$ is a coefficient for giving a threshold value by which it can be defined as "overlapping".

Preferably, $\alpha$ is 1.5 and $\beta$ is 0.8.

Next, in the present invention, adjustment (optimization) is conducted so that the score of the interaction function determined in Step S-6 is maximum (Step S-7). Here, as the procedure for maximizing the score, a simulated annealing method is exemplified. For reducing the time, it is preferred to employ a process in which Step S-5 and Step S-6 are repeated plural times (for example, 1000 times) to find a pair in which Sscore(i,j) is maximum, and a ligand is superposed to an initial coordinate based on information of the found pair.

Next, in the present invention, interaction energy with respect to the protein is calculated for the ligand which is superposed in optimization of the interaction function in Step S-7, and the resultant interaction energy is optimized while finely adjusting the conformation of the ligand coordinate data (Step S-8). The fine adjustment of ligand conformation may be conducted by translating, rotating or changing coordinates in such an extent that the angle around a single bond will not exceed 0.3 by RSMD, about the ligand coordinate calculated in Step S-7.

Here, the fine adjustment of conformation of ligand coordinate data is preferably optimized by random search, for example. In random search, minimal changes between active site of the protein and ligand are repeated, for example, 8000 times in accordance with the items 1) to 3) below, to make an optimum energy "U optimum" is minimum.

1) Up to five bonds are selected at random from rotatable bonds, and each bond is randomly rotated within the range of ±10.0 degrees for changing the conformation of the ligand. This process is effected, for example every three times.
2) In each of x, y and z axial directions, the ligand is randomly translated within the range of ±1.0 angstrom. This process is effected, for example, every two times.
3) In each rotation center coordinate, a coordinate of the rotation center is randomly moved within the range of ±1.0 angstrom, and the ligand is randomly rotated within the range of ±5.0 degrees with respect to each of direction of three orthogonal axes. This process is effected, for example every five times.

Next, in the present invention, conformation of ligand coordinate data is largely changed, and then the process from Step S-5 is started again and the process up to Step S-8 for optimization is repeated (Step S-9). Modification of conformation may be conducted by translating, rotating or changing coordinates in such an extent that the angle around a single bond will be equal to or more than 0.3 by RSMD, about the ligand coordinate calculated in STEP S-7.

Here, optimization by largely moving conformation of the ligand is achieved by selecting five rotatable bonds at random, for example, with respect to the conformation in the "U optimized" which is energy optimized in Step S-8, and rotating them randomly in accordance with a rotation angle interval determined for each atom type. Then the process after Step S-5 is repeated, for example, 5000 times.

After changing conformation of the ligand, internal energy of the ligand "U internal" is calculated, and if the value is 500.0 or more, a subsequent calculation may be skipped, and the next ligand conformation may be caused to generate. Next, in the present invention, the process from. Step S-4 to Step S-9 is conducted for the plural sets of post-structural-change protein coordinate data prepared in Step S-3, and an optimum coordinate of protein-ligand complex, and optimum energy "U optimum" are calculated (Step S-10).

Next, in the present invention, the above process is conducted for every ligand in the compound database prepared in Step S-1, and a ligand which possibly binds to the target protein is selected from the compound database (Step S-11).

In the above, a basic principal of the present invention was described. In the present invention, however, when any one of a parameter reflecting induced-fit of protein and post-structural-change 3D structure coordinate or both are calculated using molecular dynamic calculation method, normal mode with respect to 3D structure of the target protein may be calculated; fluctuations of respective amino acids may be determined; molecular dynamic calculation may be conducted while using the intensity of the fluctuation as a constraint condition; and thereby molecular dynamic calculation may be conducted so that a 3D structure of the protein will not largely differ from the energy optimized structure.

In the present invention, the molecular dynamic calculation according to the present molecular dynamic calculation method may be so conducted that, for example, a fluctuation value of a dihedral angle of a main chain atom is calculated from the normal mode calculation, and the fluctuation value is substituted into a coefficient of force K in the molecular dynamic calculation as shown in Formula 2 or Formula 3.

$$Erot = Krot(\phi - \phi 0)^2 \quad \text{[Formula 2]}$$

Erot represents energy of a dihedral angle of a main chain atom in a 3D structure of a protein. $\phi$ represents a dihedral angle of a main chain atom. $\phi 0$ represents a standard value of a dihedral angle of a main chain atom. Here, when a value of Krot is large, $\phi$ is constrained by $\phi 0$.

$$Epos = Kpos(r - r0)^2 \quad \text{[Formula 3]}$$

Epos represents position energy of a main chain atom in a 3D structure of a protein. r represents a coordinate of main chain atom. r0 represents standard value of the coordinate of the main chain atom. Here, when a value of Kpos is large, r is constrained by r0.

In the present invention, as a target function (interaction function) in evaluation of interaction between ligand and protein, a dynamic property function that expresses dynamic properties of a protein may be added to the conventional interaction energy function as "Elastic energy". As a result, it is possible to rapidly calculate interaction energy from a 3D structure coordinate of a protein, and to clearly describe a physicochemical property regarding dynamic behavior of the protein.

Here, as the "elastic energy", the function "U collision" shown by Formula 4 below may be adapted in consideration of local flexibility of protein. In the following example, when interatomic distance R between an i-th atom of a main chain or a side chain with a little dynamic behavior in active site, and a j-th atom in a ligand is not more than collision distance "Rcollision(i,j)", calculation of $\phi(i,j)$ is defined as follows.

$$U_{collision} = \sum_{i=1}^{M} \sum_{j=1}^{N} \varphi(i, j)$$

$$\varphi(i, j) = K \text{ collision} * (R \text{ collision}(i, j) - R)^2$$

M is the number of atoms in the active site that prohibit collision, N is the number of atoms of a ligand. "K collision" is preferably 1000.0. "Rcollision(i,j)" is a sum of van der Waals radii of i-th atom in the active site and j-th atom in the ligand.

Here, with respect to each atom in the active site, when weighing w(i) that allows collision is defined, the function "U collision" shown by the following Formula 5 is used. w(i) is real number ranging from 0 to 1.

$$U_{collision} = \sum_{i=1}^{M} \sum_{j=1}^{N} \varphi(i, j) \quad \text{[Formula 5]}$$

$$\varphi(i, j) = w(i) * K \text{ collision} * (R \text{ collision}(i, j) - R)^2$$

M is number of atoms in the active site, N is number of atoms in the ligand. "K collision" is preferably 1000.0. "Rcollision(i,j)" is a sum of van der Waals radii of i-th atom in the active site and j-th atom in the ligand.

The "elastic energy" may be defined by using functions shown by Formula 6 below.

$Ev=w$ (hard shape region)

$E=0$ (soft shape region) [Formula 6]

Here, "hard shape region" means a part exhibiting small dynamic behavior in 3D structure of protein, and "soft shape region" means a part exhibiting large dynamic behavior. Preferably, W is a constant and 100.

In the present invention, as a function of dynamic property of the protein, a result of normal mode analysis of the protein or a result of secondary structure determination may be used. In determination of secondary structure, small fluctuation for helix or sheet regions of protein, and large fluctuation for other regions are applied to the constraint condition in interaction evaluation function and molecular dynamic calculation.

Also, according to the present invention, every plural coordinates can be evaluated equally, in short time full-automatically in screening of a ligand that binds to a target protein, even when the calculated target protein (protein coordinate data) includes typical plural 3D structural coordinates, or 3D structure of the target protein consists of plural 3D structure coordinates such as analytical result of NMR spectrum.

Also, according to the present invention, (1) coordinate data of the protein is subjected to structural change while dynamic behavior is considered by using an induced-fit parameter reflecting induced-fit, and post-structural-change protein coordinate data is selected; (2) from the selected post-structural-change coordinate data of protein, a spatial point at which superposition with ligand is to be executed is designated; (3) an interaction function when the protein and the ligand bind is calculated using the designated spatial point and ligand coordinate data of a ligand; and (4) a ligand which binds to the protein is evaluated based on the calculated interaction function. This is advantageous to screen for a ligand that binds to an induced-fit type receptor protein with high efficiency and accuracy while considering flexibility of the receptor and flexibility of the ligand.

In addition, according to the present invention, it is possible to predict a new ligand that binds to the 3D structure of a target protein by acquiring a parameter reflecting dynamic behavior of the protein which is very important for binding between protein and ligand, and using a novel interaction evaluation function in relation to a ligand, which reflects dynamic behavior of the target protein. As a result, in contrast to conventional methods, it is possible to construct 3D structures of proteins that are more reliable and suitable for design of pharmaceuticals and the like at a speed enough to keep up with enormous genomic sequences that are globally analyzed. Conventionally, in in silico screening, an algorithm capable of satisfactorily handling the induced binding that is important for interaction between proteins and ligands has not been established, however, in the present invention, by employing a calculation formula which allows simple inclusion of a parameter representing "fluctuation" of a protein obtainable from a normal mode calculation result or secondary structure prediction, into an interaction energy function between a protein and ligand, it is possible to satisfactorily handle induced binding.

Further, in molecular dynamic simulation, the present invention is featured by conducting normal mode calculation of a target protein with regard to a parameter reflecting dynamic behavior of the target protein and to an interaction evaluation function in relation to a ligand, and reflecting the calculation result into a molecular dynamic calculation. Conventionally, molecular dynamic calculation is used to simulate dynamic behavior or a protein, however, when molecular dynamic calculation is conducted on a target protein by a conventional method, the protein 3D structure will greatly differ from the coordinate that is analyzed by X-ray analysis, NMR and the like. Such difference includes a physicochemical description for dynamic behavior of the protein, however, the behavior is sometimes contradictory to the experimental result of dynamic behavior proved by NMR or the like, so that the simulation is not necessarily accurate. For this reason, in conducting molecular dynamic calculation, it is necessary to conduct a simulation while fixing the 3D structure of the protein to some extent, and in the present invention, we developed a measure for constraining a dihedral angle of a main chain atom in energy function in molecular dynamic calculation. Further, as a constraint condition of a dihedral angle, normal mode calculation of a target protein is conducted in advance for its parameter, and fluctuation of a dihedral angle of the main chain atom is calculated. The fluctuation is used as a parameter in such a manner that according to the intensity of the fluctuation, the constraint condition is relaxed for a region exhibiting large fluctuation, and the constraint condition is intensified for a region exhibiting small fluctuation. Therefore, according to the present invention, it is possible to describe dynamic behavior with high accuracy by conducting molecular dynamic simulation of a protein under such a condition. Additionally, it is possible to acquire a coordinate describing dynamic behavior of a protein from the molecular simulation thus calculated, and by using this, it is possible to conduct ligand screening using various shapes of ligand binding sites.

As a result of the above, the present invention enables new ligands to be found that would not be found by conventional in silico screening, and enables execution of analysis of protein-ligand interaction including "induced binding" that is enabled only by time-consuming molecular simulation heretofore, in a short time.

The present invention is applicable to "in silico screening" taking induced binding phenomenon into account more intensively than existent software, and achieves simplification based on correct understandings of induced binding phenomenon and hydrophobic interaction. Since the present invention is simplified, it allows handling of more target proteins by automation. As a result, it is possible to screen new possible compounds, for example, from more than a million of compound databases, and it is possible to screen possible compounds within a realistic time from a scale of databases that cannot be experimentally handled.

Further, since the present invention enables interaction analysis between protein and ligand to be conducted in a short time, interaction between many proteins causes for example, metabolism and toxity, and drugs can be analyzed, and thus prediction of in silico metabolism and toxity of drug is enabled.

Molecules that can be handled as ligands in the present invention are understood as any substances including proteins, peptides, DNAs, drug ingredients, metals, ions, sugars, nucleic acid components and hormones because used number and kinds of ligands are not limited. The present invention enables specific molecular designing of agricultural chemicals, pharmaceuticals and the like.

In a function for evaluating interaction energy between ligands and proteins, conventionally, electrostatic energy term and van der Waals term in a docking method, and an adjustment term for expressing dynamic behavior used in a soft docking method are mainly used, however, in the present invention, instead of using an adjustment term for expressing dynamic behavior used in a soft docking method or the like, a principal of elastic collision which is used in classical mechanics is applied to the interaction between the protein and the ligand, and thus the physicochemical property of interaction between the protein and the ligand is more clarified. This provides a relationship between structural change of protein and interaction, and helps rapid and correct understanding of function of a ligand.

A 3D structure of a protein used in the present invention may be adapted to a 3D structure coordinate created by using an empirical modeling method (in particular, homology modeling method and a threading method) of the protein besides 3D structure of the protein whose 3D coordinate is determined by X-ray crystalline structure analysis or the like.

[System Configuration]

Figure 116:
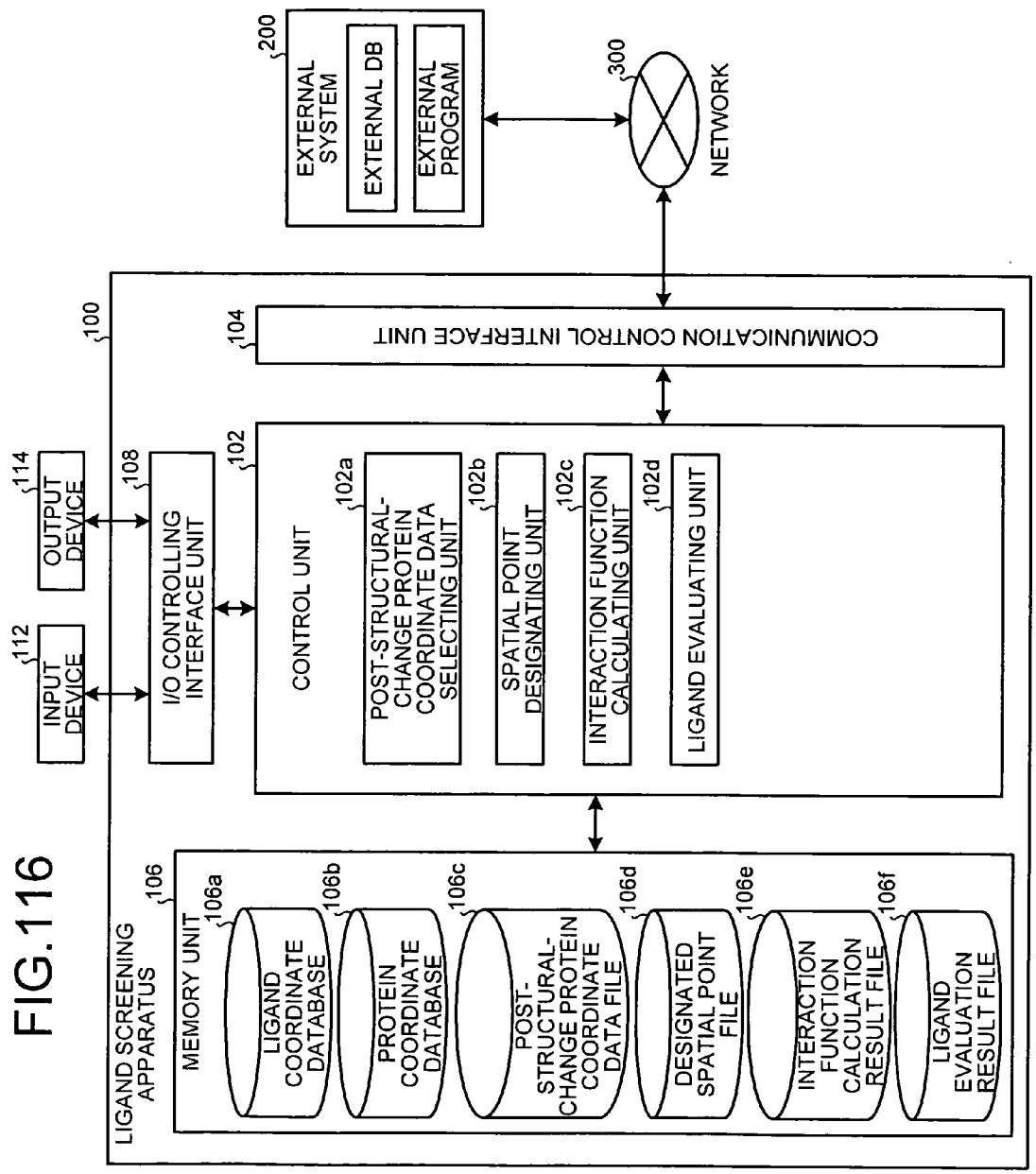
FIG. 116 is a block diagram showing one example of configuration of the present system to which the present invention is applied.

Now, configuration of the present system to which the present invention is applied will be explained in detail with reference to FIG. 116. FIG. 116 is a block diagram showing one example of a configuration of the present system to which the present invention is applied, and only the parts in the configuration that are relevant to the present invention are schematically shown.

As shown in FIG. 116, the present system is generally made up of a ligand screening apparatus 100 for evaluating and selecting a substance (ligand) that binds to a protein, and an external system 200 for providing external databases concerning a ligand 3D structure data and a protein 3D structure data, as well as a variety of external programs that are communicatively connected via a network 300.

The network 300 has a function of mutually connecting the ligand screening apparatus 100 and the external system 200, and is implemented by the Internet or LAN, for example.

The external system 200 is mutually connected with the ligand screening apparatus 100 via the network 300 and has a function of providing a user with external databases concerning a ligand 3D structure data and protein 3D structure data as well as websites for executing various external programs. Here, the external system 200 may be implemented by a WEB server, ASP server or the like, and its hardware configuration may be implemented by commercially available workstation, personal computer and the like information processing devices and attached devices thereof. Further, each function of the external system 200 is realized by a CPU, disc device, memory device, input device, output device, communication controlling device and the like in hardware configuration of the external system 200, and programs controlling them.

The ligand screening apparatus 100 generally includes, a control unit 102 such as CPU for centrically controlling the overall ligand screening apparatus 100; a communication controlling interface unit 104 connected with a communication device (not shown) such as router connected with communication line or the like; a memory unit 106 for storing various databases and files; and an input/output controlling interface unit 108 connected with an input device 112 and an output device 114, and these units are communicably connected via certain communication paths. Further, the ligand screening apparatus 100 is communicably connected to the network 300 via a communication device such as router and a wired or wireless communication line such as an exclusive line.

Various databases, tables and files (ligand coordinate database 106a to ligand evaluation result file 106f) stored in the memory unit 106 is a storage unit such as stationary disc device, and stores various programs, tables, files and databases, files for web pages used for various processings.

Among these constituents of the memory unit 106, the ligand coordinate database 106a is a ligand coordinate data storing unit that stores ligand coordinate data. A protein coordinate database 106b is a protein coordinate data storing unit that stores protein coordinate data. A post-structural-change protein coordinate data file 106c is a post-structural-change protein coordinate data storing unit that stores post-structural-change protein coordinate data selected by a post-structural-change protein coordinate data selecting unit 102a as will be described later. A designated spatial point file 106d is a designated spatial point storing unit that stores information concerning a spatial point designated by a spatial point designating unit 102b as will be described later. An interaction function calculation result file 106e is an interaction function calculation result storing unit that stores information concerning calculation result of interaction function calculated by an interaction function calculating unit 102c as will be described later. A ligand evaluation result file 106f is a ligand evaluation result storing unit that stores information concerning evaluation result of the ligand evaluated by a ligand evaluating unit 102d as will be described below.

The communication controlling interface unit 104 controls communication between the ligand screening apparatus 100 and the network 300 (or communication device such as router). In other words, the communication controlling interface unit 104 has a function of communicating data with other terminals via a communication line.

The input/output controlling interface unit 108 controls the input device 112 and the output device 114. Here, as the output device 114, a speaker or the like as well as a monitor (including home TV set) may be used (hereinafter, the output device 114 is sometimes referred as "monitor"). As the input device 112, a keyboard, a mouse, a microphone or the like may be used. A monitor also realizes a pointing device function together with a mouse.

The control unit 102 has an internal memory for storing control programs such as OS (Operating System), data in need and the like, and conducts information processing for executing various processings by these programs and the like. Functionally, the control unit 102 generally includes the post-structural-change protein coordinate data selecting unit 102a, the spatial point designating unit 102b, the interaction function calculating unit 102c and the ligand evaluating unit 102d.

Among these constituents of the control unit 102, the post-structural-change protein coordinate data selecting unit 102a is a post-structural-change protein coordinate data selecting unit that calculates structural change on coordinate data of protein using an induced-fit parameter reflecting induced-fit while taking dynamic behavior into account, and selects post-structural-change protein coordinate data. The spatial point designating unit 102b is a spatial point designating unit that selects a spatial point at which superposition with the ligand is to be conducted, from post-structural-change protein coordinate data selected by the post-structural-change protein coordinate data selecting unit 102a.

Figure 117:
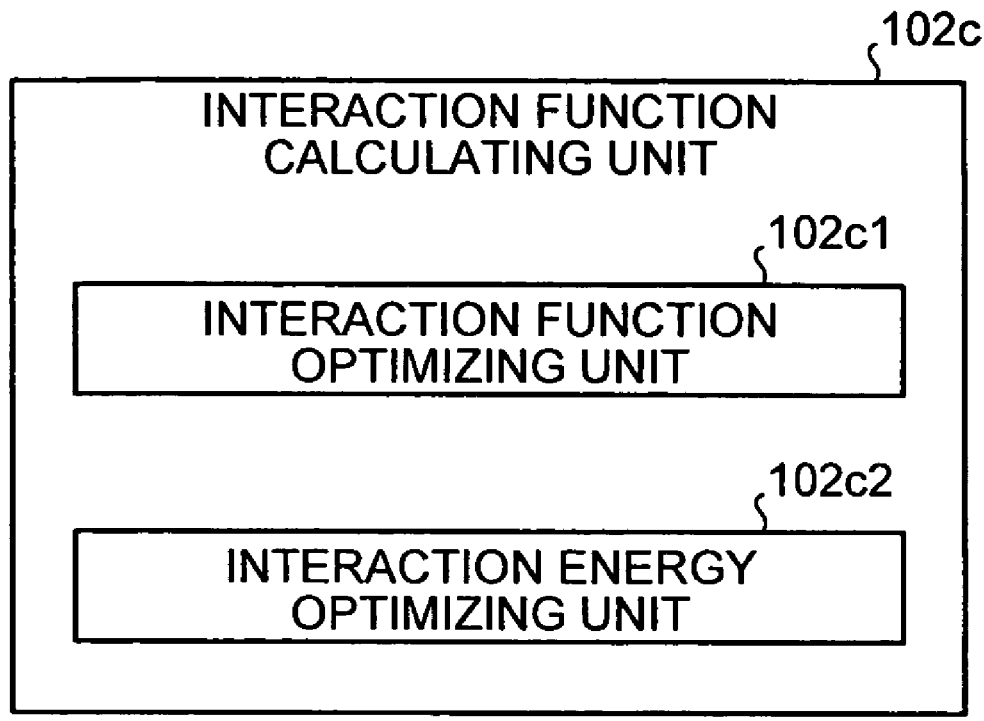
FIG. 117 is a block diagram showing one example of a configuration of an interaction function calculating unit 102c of the present system to which the present invention is applied.

The interaction function calculating unit 102c is an interaction function calculating unit that calculates an interaction function when the protein and the ligand bind using the spatial point designated by the spatial point designating unit 102b and ligand coordinate data of ligand. Here, the interaction function calculating unit 102c further includes an interaction function optimizing unit 102c1 and an interaction energy optimizing unit 102c2 as shown in FIG. 117. The interaction function optimizing unit 102c1 is an interaction function optimizing unit that optimizes so that the score of the interaction function is maximum. The interaction energy optimizing unit 102c2 is an interaction energy optimizing unit that calculates interaction energy with the protein for the superposed ligand after optimization of the interaction function by the interaction function optimizing unit 102c1, and optimizing the interaction energy while finely adjusting conformation of ligand 3D structure data.

Figure 118:
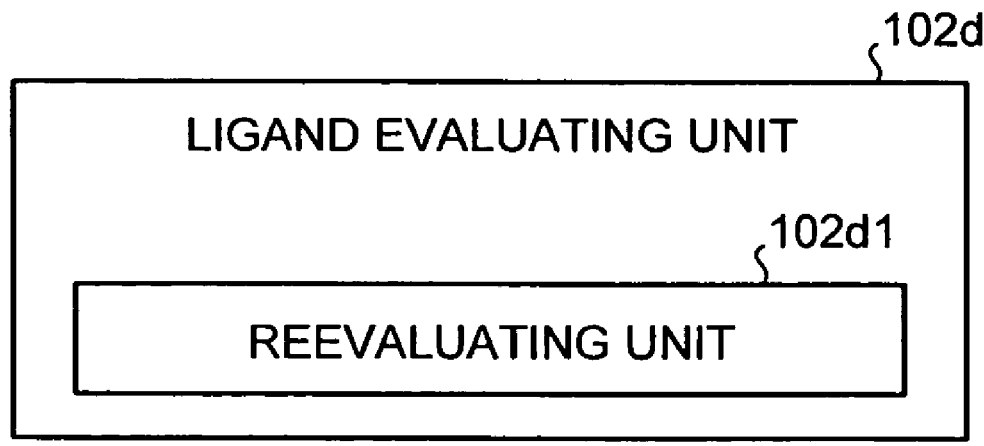
FIG. 118 is a block diagram showing one example of a configuration of a ligand evaluating unit 102d of the present system to which the present invention is applied.

Returning to FIG. 116, the ligand evaluating unit 102d is a ligand evaluating unit that evaluates a ligand that binds to the protein based on the interaction function calculated by the interaction function calculating unit 102c. Here, the ligand evaluating unit 102d also includes a reevaluating unit 102d1 as shown in FIG. 118. The reevaluating unit 102d1 is a reevaluating unit that reevaluates a ligand that binds the target protein based on an interaction function calculated by the interaction function calculating unit 102c that is executed after largely changing conformation of ligand 3D structure data following optimization by the interaction energy optimizing unit 102c2.

The details of the processes executed by these units will be described later.

[System Process]

Figure 115:
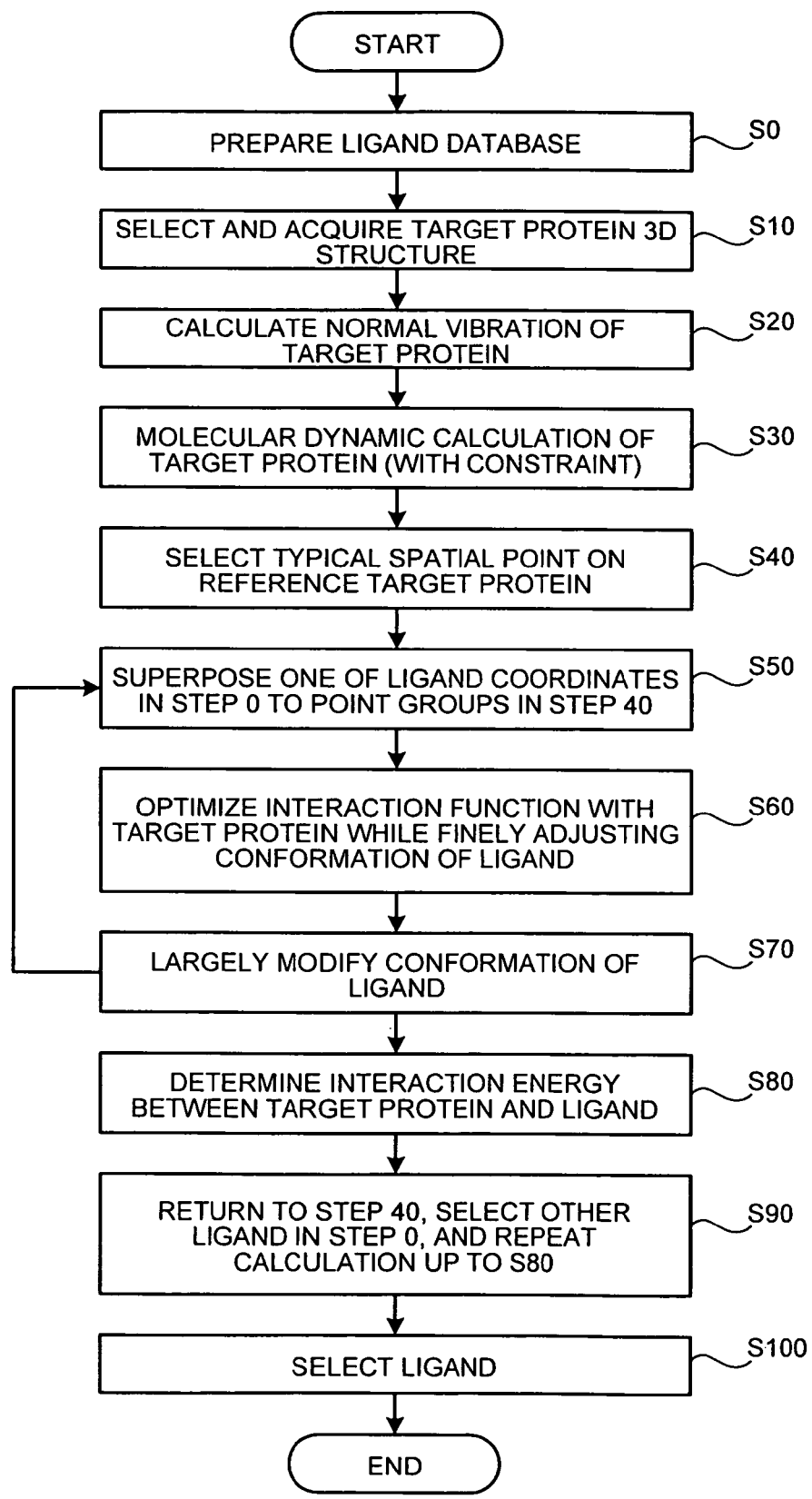
FIG. 115 is a flowchart showing one example of main process in the present system in the present embodiment.

Here, one example of a main process of the present system in the embodiment configured as described above will be explained in detail with reference to FIG. 115, for example. FIG. 115 is a flowchart showing one example of a main process of the present system in the present embodiment. Referring now to FIG. 115, ligand screening using 3D structure of protein and induced fitting will be explained.

First, the ligand screening apparatus 100 prepares a database of the ligand including 3-dimensional coordinates by a process of control unit 102 and stores the prepared database in the ligand coordinate database 106a of the memory unit 106 (Step S0). Here, as a database of the ligand, for example, available compound databases such as ACD, imaginary compound data collected by drawing a compound and the like may be used. Preferably, the database of ligand is converted into three dimensional by molecular dynamic technique.

Next, the ligand screening apparatus 100 selects a 3D structure of a target protein for screening the ligand database prepared in Step S0 for a specified ligand by a process of the control unit 102, acquires 3D structure data (3D coordinate) of the selected protein, and stores it in the protein coordinate database 106b of the memory unit 106 (Step S10). As the 3D coordinate, the 3D structure coordinate created by PDB which is a public database or by homology modeling method is preferably used.

Next, the ligand screening apparatus 100 conducts normal mode calculation for the target protein selected in Step S10 by a process of the post-structural-change protein coordinate data selecting unit 102a, and determines fluctuation in position of a main chain atom and fluctuation in a dihedral angle (Step S20). More specifically, first, a parameter representing dynamic behavior of the target protein specified in Step S10 is acquired from the database of a calculation result by a normal mode analysis method or a parameter is acquired by conducting secondary structure determining calculation.

First, a method of acquiring the parameter representing dynamic behavior of the protein in Step S20, by a normal mode analysis method will be explained. The normal mode analysis method is a method of approximating potential energy as a secondary function of displacement, and solving a dynamic equation precisely, thereby analyzing microscopic vibrations around the optimized structure. The dynamic equation to be solved is the following Formula (1) or Formula (2). For details of the normal mode analysis method, see "Wilson, E. B., Decius, J. C., and Cross P. C. 1995 Molecular vibration. McGraw-Hill.".

$$\left(\sum_j T_{ij} U_{jk}\right)\omega_k^2 = \sum_j V_{ij} U_{ik} \quad (1)$$

$$TU\Lambda = VU \quad (2)$$
$$\Lambda_{ij} = \omega_i \delta_{ij}, \ U^T TU = (\delta_{ij})$$

Here, $\omega_k$ is an eigen value, $U_{ik}$ is an eigen vector, and $\delta_{ij}$ is the delta of Kronecker. $T_{ij}$ and $V_{ij}$ are respectively concern motion energy $E_k$ and potential energy V, and the following Formula (3) and Formula (4) are provided.

$$E_k = \frac{1}{2}\sum_{i,j} T_{ij}\dot{q}_i\dot{q}_j \quad (3)$$

$$U_{vdw} = K_{vdw} \sum_{i,j(>i+2)} \left\{\left(\frac{3.8}{D_{i,j}}\right)^{12} - \left(\frac{3.8}{D_{i,j}}\right)^6\right\} \quad (4)$$

Here, $q_i$ is a coordinate corresponding to a degree of freedom of vibration. $q_i$' (it means "$q_i$ dot" in Formula (3)) is differentiation of $q_i$ by time. $q_j$ is expressed by the following Formula (5).

$$q_j = q_j^0 + \sum_k A_{jk} Q_k \quad (5)$$

Here, $A_{jk}$ is a coefficient which connects motion $Q_k$ and individual atomic motion $q_j$. $q_j^o$ is an optimized coordinate. $Q_k$ is normal mode shown by the following formula.

$$Q_k = \alpha_k \cos(\omega_k t + \delta_k)$$

Here, $\alpha_k$ and $\delta_k$ are determined as an initial condition.

Next, in Step S20, with respect to a reference protein, using the eigen value and the eigen vector obtained above, positional fluctuation of each Cα atom at a certain temperature and a certain eigen value is calculated, and this value of fluctuation is defined as a value of fluctuation of the amino acid in which the Cα is contained. As to a value of fluctuation of each amino acid in a target protein, using the alignment in Step S50, a value identical to that for the reference protein is applied as a value of fluctuation of the target protein in a corresponding amino acid residue pair based on comparison of the target sequence and the reference sequence. For those whose values of fluctuation are not obtained, a predetermined value is applied. The value of each amino acid in the target protein thus obtained is used as a parameter representing dynamic behavior of the target protein.

Now, a method of acquiring a parameter representing dynamic behavior of protein by secondary structure determining calculation in Step S20 will be explained. Secondary structure determination is calculated from the 3D structure coordinate of the protein. As software, DSSP, STRIDE and the like are preferred, but basically, a method which makes a determination based on angle of twist of a main chain of the protein and hydrogen bond pattern may be used. Here, "DSSP (Dictionary of protein secondary structure of protein)" is software that determines α-helix and β-sheet by using a PDB format file as an input file and analyzing a hydrogen pattern of a main chain, an internal-rotation angle and the like. For details of the DSSP, see "Kabsch, W. & Sander, C. (1983) Dictionary of protein secondary structure: pattern recognition of hydrogen-bonded and geometrical features. Biopolymers, 22:2577-2637". "STRIDE (Protein secondary structure assignment from atomic coordinate)" is software that determines α-helix and β-sheet by using a PDB format file as an input file and analyzing a hydrogen pattern of main chain, an internal-rotation angle and the like. For details of STRIDE, see "Frishman, D & Argos, P. (1995) Knowledge-based secondary structure assignment. Proteins: structure, function and genetics, 23, 566-579".

A secondary structure calculation using the above software or the like is conducted on the reference protein, and α-helix structure, β-sheet structure or loop structure formed by each amino acid is determined. As to secondary structure determination of each amino acid in a target protein, using the alignment in Step S50, the same value for the reference protein is applied as secondary structure of the target protein in a corresponding amino acid residue pair based on comparison of the target sequence and the reference sequence. For those whose secondary structures are not determined, a predetermined result is applied. The secondary structure of each amino acid in the target protein thus obtained is used as a parameter representing dynamic behavior of the target protein.

Here, in Step s20, as a parameter representing dynamic behavior of the target protein, a calculation result acquired by the normal mode analysis method of the reference protein is preferably used. As such a calculation result, those separately stored in a database are used. Also, the secondary structure determining calculation result is used in place of normal mode analysis calculation when a reference protein for which normal mode analysis is not conducted is used.

Returning again to a main process of FIG. 115, the ligand screening apparatus 100 conducts molecular dynamic calculation using intensity of fluctuation of target protein determined in Step S20 by a process of post-structural-change protein coordinate data selecting unit 102a as a constraint condition (Step S30).

Concretely, first, positional constraint energy of main chain "U position" is introduced into Formula 6 as shown below, and minimization (condition: temperature 300K, rectangular water bath capable of placing two at least spheres of water molecule in all directions outside the surface of the receptor, force field: AMBER [S. J. Weiner, P. A. Kollman, D. A. Case, U. C. Singh, C. Ghio, G. Alagona, S. Profeta, &, P. Weiner (1984) A new force field for molecular mechanical simulation of nucleic acids and proteins J. Am. Chem. Soc. 106, 765-784]) is effected using APRICOT [Yoneda S. & Umeyama H. (1992) Free energy perturbation calculations on multiple mutation base J. Chem. Phys. 97, 6730-6736] with the variation of the initial receptor backbone constrained.

$$U \text{ position} = K \text{ position} * R^2 \quad (6)$$

Here, the "K position" is, for example, 300.0 and R is difference from an initial coordinate. Next, dihedral angle constraint energy "U dihedral angle" shown by Formula 7 below is introduced to APRICOT, and MD of the minimized receptor is calculated (condition: temperature 300K, rectangular water bath capable of placing two at least spheres of water molecule in all directions outside the surface of the receptor, force field: AMBER).

$$U \text{ dihedral angle} = K \text{ dihedral angle} * (\theta - \theta \text{ equivalent})^2 \quad (7)$$

θ is dihedral angle (unit: rad). For "K dihedral angle", a maximum value and a minimum value are designated so that uneven constraint that corresponds to the fluctuation of the main chain is applied to each dihedral angle within the range between the above values. Hereinafter, MD that is conducted under constraint of dihedral angle is called MD with dihedral angle constrained.

Next, dynamic structure of a receptor is clustered for obtaining a protein structure coordinate by MD calculation with a dihedral angle constrained. For a previously designated active site, a population made up of active sites in structures obtained by superposing receptors of every 100 femtoseconds in the course of MD and an active site in an initial structure is established. Since dynamic information of a side chain is easily lost by clustering, at first, side chain dihedral angles wherein dihedral angle χ of side chain is conserved within an average angle ±20.0 degrees in a % of the population are collected. However, when it is determined that χ closer to the main chain is not conserved, the subsequent χ is considered as not being conserved.

Next, structures that conserve every dihedral angle of side chain in collected those are extracted from the population. Then, to compare similarity of the extracted structures, when rms (root mean square) of all atoms is β angstroms or less, it is determined as the same structure, and one is deleted, and based on the finally selected structures, a receptor dynamic structure cluster is created. As to an atom constituting unconserved dihedral angle χ, it is allowed to collide with a ligand in that calculation binding to active site because it is likely to vary. α and β are constants.

Returning again to the main process of FIG. 115, the ligand screening apparatus 100 designates a group of spatial points for locating a ligand to a ligand binding site of the target protein by a process of the spatial point designating unit 102b (Step S40). Concretely, among the plural protein 3D structure coordinates created in Step S30, one is randomly selected. A spatial point in a protein coordinate is designated, for example, by the methods (1) to (4) below.

(1) Designation of Spatial Point by Generation of a Dummy Atom

Focusing on the hydrogen bond in the interaction between a ligand and a protein, a hydrogen bond site in the protein is designated as a spatial point. The important issues in a hydrogen bond are distance and angle. That is, a hydrogen in hydrogen bond donor (hereinafter referred to as "donor") is required for calculating an angle.

In the present embodiment, when there is no hydrogen atom in an active site and the ligand, a dummy hydrogen atom is generated in accordance with the following rule.

1) A dummy atom is generated in an equilateral triangle centered at a $sp^2$ orbital atom (FIG. 2). More specifically, as shown in FIG. 2, a dummy hydrogen atom (B) is generated at a free position in the equilateral triangle centered at the nitrogen atom (A) of a $sp^2$ orbital type.

2) As to a $sp^3$ orbital atom, when it is at a distance to form a hydrogen bond, it is deemed to rotate so as to share the hydrogen atom, so that only the distance is considered in calculation of hydrogen bond interaction. Therefore, no dummy atom is generated for the $sp^3$ orbital atom.

As to metal and water, since they can mediate the binding between active site and ligand binding, a dummy atom is generated at an interacting position in the manner as described below.

1) To metal such as iron, dummy atoms are generated in a regular octahedron (FIG. 3). That is, as shown in FIG. 3, dummy atoms (B) are generated at free positions in the regular octahedron centered at zinc (A).

2) To water, dummy atoms are generated in a regular tetrahedral. It is not necessary to generate a dummy atom in the direction in which it interacts with an active site.

(2) Designation of Spatial Point Using Structure-Activity Relationship Information.

Also in the present invention, a spatial point is designated by inputting information of the following items (A) to (D) in focus of structure-activity relationship (SAR) information of ligand.

(A) Atom of active site obtained from SAR information (hereinafter referred to as "A atom"). It follows PDB format.
(B) Atom type of ligand which is expected to interact with "A atom" (hereinafter referred as "B type"). It follows MOL2 format of SYBYL.
(C) Intensity of interaction between "A atom" and "B type" (hereinafter referred to as "C intensity").
(D) Distance of interaction between "A atom" and "B type" (hereinafter referred to as "D distance") (unit: angstrom).

In the present embodiment, a spatial point may be created according to the rules shown 1) to 4) below based on the input information (A) to (D) and using an initial coordinate of ligand in an active site of protein.

1) When the "A atom" is donor or metal and water (when SAR information on the active site side is designated as hydrogen bond donor or metal atom), a position and a surrounding at "D distance" from "A atom" with respect to the direction of dummy atoms generated in "(1) Designation of spatial point by generation of dummy atom" are selected as initial coordinates (FIG. 4 and FIG. 5).

2) When the "A atom" is a $sp^3$ orbital atom (when designation of SAR information on the active site side is a $sp^3$ orbital atom), a surrounding at "D distance" from "A atom" is selected as initial coordinate (FIG. 6).

3) When "A atom" is a hydrogen bond acceptor (hereinafter referred to as "acceptor") (when designation of SAR information on the active site side is a hydrogen bond acceptor), a position and a surrounding at "D distance" on a bonding extension line of "A atom" are selected as initial coordinates (FIG. 7).

4) In other cases (when designation of SAR information on the active site side is an atom other than the above), a position on the surface of a sphere with radius of "D distance" centered at "A atom" is selected as an initial coordinate (FIG. 8).

Here in contrast with the above 1) to 4), an initial coordinate of ligand may be designated directly.

Returning again to the main process of FIG. 115, the ligand screening apparatus 100 superposes each atom in the ligand for one ligand specified in Step S0 to the group of spatial points determined in Step S30 by a process of the interaction function calculating unit 102c (Step S50). Concretely, an initial coordinate and a ligand are superposed by the following procedures (1) to (4) which are alignment creating algorithm using distance matrix (DALI) [Holm, L., & Sander, C. (1993) Protein Structure Comparison by Alignment of Distance Matrices J. Mol. Biol. 233, 123-138] modified for low molecules.

(1) It is often the case that the atom types of the ligand correspond to those of "B type" multiply. In view of this, a pair wherein an atom type of "B type" and that of the ligand can be regarded as being identical is created by using random numbers. In such a pair, atom types of ligand should not overlap.

(2) Since "B type" includes a plurality of initial coordinates by Step S40, selection of initial coordinate is also selected by using random numbers.

(3) Create a distance matrix of the selected initial coordinate and ligand, and calculate Sscore(i, j) which is an interaction function as follows.

$$Sscore(i, j) = \sum_{ij}^{\lambda} \begin{cases} \alpha \times [\exp\{-(d_{ij}^s - d_{ij}^c)^2\} - \beta] / \frac{(d_{ij}^s + d_{ij}^c)^2}{2} & \text{when } i \text{ is not equal to } j \\ \alpha \times (1 - \beta) & \text{when } i \text{ is equal to } j \end{cases}$$

Here, $d_{ij}^s$ is a distance between i-th spatial point and j-th spatial point in the target protein. $d_{ij}^s$ is an interatomic distance between i-th atom and j-th atom in a compound. α is a coefficient for making Sscore(i,j) the maximum value when the group of spatial points in the target protein and the compound completely overlap with each other. β is a coefficient for giving a threshold value by which it can be defined as "overlapping".

Preferably, α is 1.5 and β is 0.8.

(4) Repeat (1) to (3) plural times (for example, 10000 times) to find a pair whose Sscore(i, j) is maximum, and superpose a ligand to an initial coordinate based on that pair information.

Next, the ligand screening apparatus 100 acquires a parameter representing dynamic behavior of a protein according to the calculation result determined in Step S20 and Step 30 for superposition in Step S50 by a process of the interaction function calculating unit 102c, and calculates interaction energy between ligand and protein using the parameter while finely adjusting conformation of the ligand (Step S60). In other words, with respect to the ligand that is superposed in Step S50, interaction energy with the protein is calculated while optimizing the conformation by fine adjustment. Fine adjustment of conformation of the ligand may be conducted by translating, rotating or changing coordinates in such a range that the angle around a single bond will not exceed 0.3 by RSMD, about the ligand coordinate calculated in Step S50.

Here, the fine adjustment of conformation of ligand coordinate data is preferably optimized by random search, for example. In random search, infinitesimal changes between active site of protein and ligand are repeated, for example, 8000 times in accordance with the items 1) to 3) below, to make an optimum energy "U optimum" be minimum.

1) Up to five bonds are selected at random from rotatable bonds, and each bond is randomly rotated within the range of ±10.0 degrees for changing the conformation of the ligand. This process is effected, for example every three times.
2) In each direction of x, y, z axes, the ligand is randomly translated within the range of ±1.0 angstrom. This process is effected, for example every two times.
3) In each center coordinate of rotation, a center coordinate of the rotation is randomly translated within the range of ±1.0 angstrom, and the ligand is randomly rotated within the range of ±5.0 degrees with respect to each of direction of three orthogonal axes. This process is effected, for example every five times.

Here, optimum energy "U optimum" is defined by the following formula. The energy functions shown on the right-hand side will be individually explained below.

$$U \text{ optimum} = U_{SAR} + U \text{ hydrogen} + U \text{ hydrophobic} + U \text{ stacking} + U \text{ collision} + U \text{ internal}$$

As to van der Waals radius and interatomic interaction distance, references were made to AMBER99 [J. Wang, P. Cieplak & P. A. Kollam (2000) How well does a restrained electrostatic potential (RESP) model perform in calculating conformational energies of organic and biological molecules? J. Comput. Chem, 21, 1049-1074] and MM3 parameter [Ma B., Lii J.-H., Allinger N. L. (2000) Molecular polarizabilities and induced dipole moments in molecular mechanics J. Comput. Chem. 21, 813-825].

(a) Energy Function "$U_{SAR}$" Concerning SAR Information

As an index according to SAR information, energy $U_{SAR}$ is defined as follows.

$$U_{SAR} = \sum_{i=1}^{N} \varphi(i)$$

$$\varphi(i) = K_{SAR}(i) * (R_{SAR}(i) - R)^2 - \delta$$

N is the number of SAR information, R is distance from "A atom" to an interacting atom on the ligand side, $K_{SAR}(i)$ is i-th "C intensity", $R_{SAR}(i)$ is i-th "D distance". $\delta$ is, for example, 20.0.

(b) Energy Function "U hydrogen" Concerning Hydrogen Bond

Figure 9:
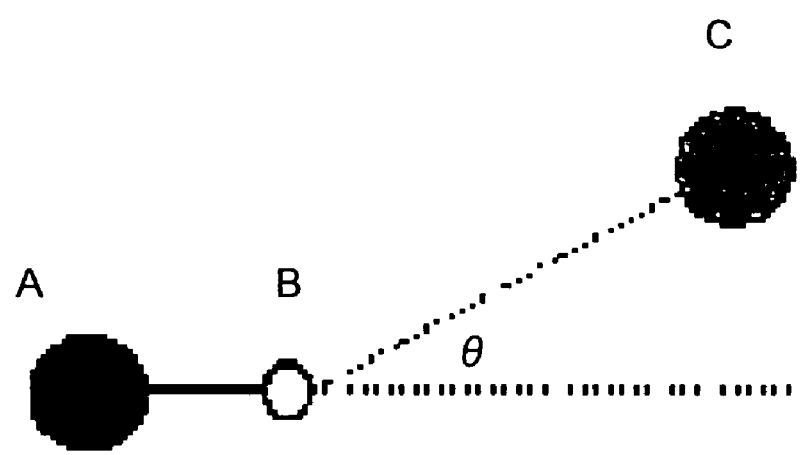
FIG. 9 is an illustrative view of definition of angle of hydrogen bond.

Assuming only one hydrogen bond is formed with respect to one donor (acceptor) of a ligand, an acceptor (donor) on the active site side located at shortest distance is chosen, a binding angle θ via a hydrogen (see FIG. 9, the acutest hydrogen bond angle is defined as θ when plural hydrogen atoms are attached to a donor atom) is calculated, and in either of the two conditions described below, φ(i) is calculated. In FIG. 9, A is a donor, B is hydrogen, C is acceptor and θ is angle of hydrogen bond.

$$U_{hydrogen} = \sum_{i=1}^{N} \varphi(i)$$

(1) When the donor atom is a $sp^3$ orbital type, or angle of hydrogen bond 0 is within ±30.0 degrees, $$\text{If } R > R_{hydrogen}, \quad \varphi(i) = -\frac{K_{hydrogen}(i)}{(R - R_{hydrogen}(i) + 1.0)}$$

$$\text{Else,} \quad \varphi(i) = -\frac{K_{hydrogen}(i)}{(R_{hydrogen}(i) - R + 1.0)}$$

(2) When angle of hydrogen bond 0 is equal to or more than ±30.0 degrees, $$\text{If } R > R_{hydrogen}, \quad \varphi(i) = -\frac{K_{hydrogen}(i)}{(R - R_{hydrogen}(i) + 1.0) * \theta}$$

$$\text{Else,} \quad \varphi(i) = -\frac{K_{hydrogen}(i)}{(R_{hydrogen}(i) - R + 1.0) * \theta}$$

N is the number of sum of donors and acceptors of the ligand, R is distance between two atoms forming a hydrogen bond, "K hydrogen (i)" and "R hydrogen (i)" are intensity and distance of interaction of hydrogen bond determined for each atom type.

(c) Hydrophobic Interaction Energy Function "U Hydrophobic"

Atoms that are capable of hydrophobic interaction in active site (side chains of ALA, CYS, PHE, ILE, LEU, MET, PRO, VAL, TRP and TYR, except of hydroxyl group of TYR) and in the ligand (carbon atom) are serially numbered, and when interatomic distance R between i-th atom in the active site and j-th atom in the ligand is within a cutoff, φ(i,j) is calculated.

$$U_{hydrophobic} = \sum_{m=1}^{M} \sum_{n=1}^{N} \varphi(i, j)$$

$$\text{If } R > R_{hydrophobic}(i, j), \quad \varphi(i, j) = -\frac{K_{hydrophobic}(i, j)}{(R - R_{hydrogen}(i, j) + 1.0)}$$

$$\text{Else,} \quad \varphi(i, j) = -K_{hydrophobic}(i, j)$$

M is number of atoms in active site that are capable of hydrophobic interaction, N is number of atoms in ligand site that are capable of hydrophobic interaction. "K hydrophobic (i,j)" and "R hydrophobic (i,j)" are intensity and distance of hydrophobic interaction determined for each atom type. The cutoff is, for example, 8.0 angstroms.

(d) Stacking Energy Function "U Stacking"

Figure 10:
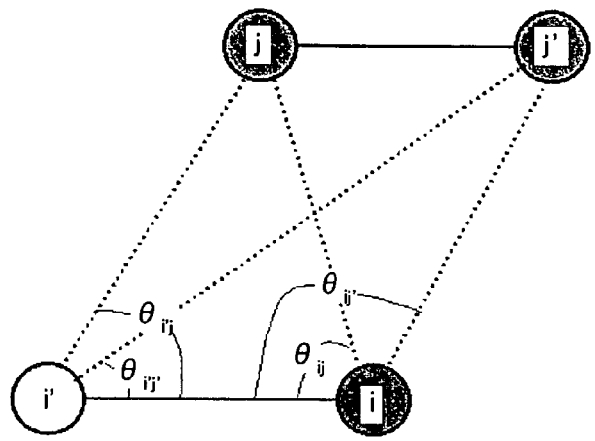
FIG. 10 is an illustrative view of definition of angle in stacking.

Atoms forming an aromatic ring in the active site and the ligand are serially numbered, and a center coordinate of aromatic ring is calculated for the active site. When interatomic distance R between the i-th atom in the active site and the j-th atom in the ligand is within a cutoff, taking a center coordinate of aromatic ring formed by the i-th atom as i', and taking an atom in ligand which is closest from j-th atom and belonging to the same aromatic ring as j', $\angle ii'j=\theta_{i'j}$, $\angle i'ij=\theta_{ij}$, $\angle ii'j'=\theta_{i'j'}$, $\angle i'ij'=\theta_{ij'}$ are calculated (FIG. 10), and when $\theta_{i'j}$ and $\theta_{ij}$ are 90.0 degrees ±10.0 degrees, "R boundary" and "θ boundary" are determined, and in either of the two conditions described below, φ'(i,j) is calculated. In FIG. 10, i' represents center of aromatic ring in active site, i represents aromatic ring atom in active site, j and j' represent aromatic ring atoms in the ligand.

$$U_{stacking} = \sum_{i=1}^{M} \sum_{j=1}^{N} \varphi(i, j)$$

If $R$ boundary $< 0.0$, $\varphi(i, j) = -K$ stacking $(i, j) * R$ boundary

Else, $\varphi(i, j) = -K$ stacking $(i, j) * \theta$ boundary $R$ boundary $= 1.0 - (R$ stacking $(i, j) - R)^2$ $\theta$ boundary $= |1.0 - \Theta|$ $\Theta = \dfrac{\pi}{180.0} * (\theta - 90.0)^2$ M is a number of atoms forming an aromatic ring in the active site, N is the number of atoms forming aromatic ring in the ligand, and "K stacking (i,j)" and "R stacking (i,j)" are distance and intensity of stacking determined for each atom type. π is the ratio of the circumference of a circle to its diameter, and θ is an angle at which Θ is minimum in $\theta_{i'j'}$ and $\theta_{ij'}$. The cutoff is, for example, 5.0 angstroms.

(e) Intermolecular Collision Energy Function (Elastic Collision Energy Function) "U Collision"

As "elastic energy", the following function "U collision" may be applied while taking local flexibility of protein into account. When interatomic distance R between an i-th atom of a main chain or a (conserved) side chain atom with a little dynamic behavior in an active site, and j-th atom in the ligand is not more than collision distance "Rcollision(i,j)", calculation of φ(i,j) is defined as follows.

$$U_{collision} = \sum_{i=1}^{M} \sum_{j=1}^{N} \varphi(i, j)$$

$\varphi(i, j) = K$ collision$*(R$ collision$(i, j) - R)^2$

M is a number of atoms in an active site that prohibit collision, N is a number of atoms of the ligand. "K collision" is preferably 1000.0. "Rcollision(i,j)" is a sum of van der Waals radii of i-th atom in the active site and j-th atom in the ligand.

Here, with respect to each atom in the active site, when weighting w(i) that allows collision is defined, the function "U collision" shown by the following Formula is used. w(i) is a real number ranging from 0 to 1.

$$U_{collision} = \sum_{i=1}^{M} \sum_{j=1}^{N} \varphi(i, j)$$

$\varphi(i, j) = w(i) * K$ collision$*(R$ collision$(i, j) - R)^2$

M is a number of atoms in an active site. N is a number of atoms in a ligand. "K collision" is preferably 1000.0. "Rcollision(i,j)" is a sum of van der Waals radii of i-th atom in active site and j-th atom in ligand.

(f) Ligand Internal Energy "U Internal"

Since there is a case that a bond is broken due to errors that occur when a rotatable bond is changed little by little, calculations for "φ bond length (i)" and "φ collision (i,j)" are defined so as to prevent occurrence of atomic collision within a ligand.

$$U_{internal} = \sum_{i=1}^{L} \varphi_{bond\ length}(i, j) + \sum_{i=1}^{M} \sum_{j=1}^{N} \varphi_{collision}(i, j)$$

$\varphi$ bond length$(i) = K$ bond length$*$ $\{1000.0*(R$ bond length$(i) - R_1)\}^2$ $\varphi$ collision$(i, j) = K$ collision$*(R$ collision$- R_2)^2$ L is the number of rotatable bonds, M is the number of atoms of the ligand, and N is number of non-binding atoms of the i-th atom. Preferably, "K bond length" is 100.0. "R bond length (i)" is bond length of initial structure. Preferably, "K collision" is 150.0 and "R collision" is 2.2 angstroms. $R_1$ and $R_2$ are distances between two atoms.

Returning again to the description of the main process of FIG. 115, by a process of the interaction function calculating unit 102c, the ligand screening apparatus 100 largely changes conformation of ligand coordinate data with respect to the ligand determined in Step S50, restarts the flow from Step S50, and repeats the process from Step S60 to Step S70 (optimization). Change of conformation may be conducted by translating, rotating or changing coordinates in such a range that the angle around a single bond will be equal to or more than 0.3 by RSMD, about the ligand coordinate calculated in Step S50.

Here, optimization by largely changing conformation of the ligand is achieved by selecting five rotatable bonds at random, for example, with respect to the conformation in the "U optimized" which is energy optimized in Step 50, and rotating them randomly in accordance with a rotation angle interval determined for each atom type. Then the process subsequent to Step S50 and Step S60 is repeated, for example, 5000 times.

After changing conformation of the ligand, internal energy of the ligand "U internal" is calculated, and if the value is 500.0 or more, a subsequent calculation may be skipped, and the next ligand conformation may be caused to generate.

Next, the ligand screening apparatus 100 determines interaction energy between target protein and ligand that is obtained up to Step S70 by a process of interaction function calculating unit 102c (Step S80). Concretely, a complex coordinate between the protein and the ligand which provide optimum value in "U optimum" from Step S40 to Step S70, as well as optimum energy "U optimum" are calculated.

Next, the ligand screening apparatus 100 returns to Step S40 by a process of the control unit 102, selects another ligand in Step S0, and conducts the calculations up to Step S80 by processes of the respective processing units (Step S90). Here, the processes from Steps S40 to Step S90 are conducted for all ligands in the compound database in Step S0.

Next, the ligand screening apparatus 100 compares the interaction energies determined in Step S90 for the ligands in Step S0 by a process of a ligand evaluating unit 102d, and selects a ligand that is expected to bind the target protein (Step S100). Concretely, based on a complex coordinate between the protein and the ligand and optimum energy "U optimum" evaluated up to Step S90, a compound (ligand) which has a possibility to bind to the protein is selected from the database in Step S0.

Now we end the description of the main process of the system.

As described above, according to the ligand screening apparatus 100, it is possible to evaluate and select a substance (ligand) that binds to a target protein by means of interaction function. Concretely, 3D structure of the target protein is subjected to normal mode calculation, intensity of fluctuation of each amino acid is determined, and molecular dynamic calculation is conducted using the intensity of fluctuation as a constraint condition. Accordingly, it is possible to conduct molecular dynamic calculation while preventing the 3D structure of the protein from largely deviating from the structure at which energy is minimized. It is also possible to clearly describe the physicochemical property concerning dynamic behavior of a protein. Further, it is possible to use a result of normal mode analysis or a result of secondary structure determination of a protein as a function expressing dynamic property of protein. Also, when there exist plural 3D structural coordinates as is the case for analytical result of NMR spectrum, it is possible to evaluate all of the plural coordinates equally, in short time and full-automatically for screening for a ligand that binds to the target protein.

Further, according to the ligand screening apparatus 100, when arbitrary 3D structure of a protein comprising not only single but also plural chain(s) is given, a parameter reflecting induced-fit from the 3D structure of the protein and post-structural-change 3D structure coordinate are calculated in advance by a normal mode calculation method or by a molecular dynamic calculation method; an interaction function when the protein binds to other substance is defined using the above parameter and the post-structural-change 3D structure coordinate; and a substance that binds to the protein is evaluated and selected based on the interaction function by means of a computer program.

Further, according to the ligand screening apparatus 100, when a ligand that binds to the protein is selected, the series of processes shown in (0) to (8) are executed fully automatically or manually.

(0) Select one ligand from compound database. As 3D structure of a target protein, a plurality of structural-change coordinates considering dynamic behavior using a parameter reflecting induced-fit are prepared, and one of them is selected at random.
(1) Designate a spatial point in the protein at which superposition is to be conducted.
(2) Select a pair of an atom in the ligand selected in (0) and a spatial point designated at random in (1) so that no overlapping occurs.
(3) Calculate the following Sscore(i,j).

$$Sscore(i,j) = \sum_{ij} \begin{bmatrix} \text{when } i \text{ is not equal to } j \\ \alpha \times [\exp\{-(d_{ij}^s - d_{ij}^c)^2\} - \beta] / \frac{(d_{ij}^s + d_{ij}^c)^2}{2} \\ \text{when } i \text{ is equal to } j \\ \alpha \times (1 - \beta) \end{bmatrix}$$

$d_{ij}^S$ is distance between ith spatial point and j-th spatial point in the protein. $d_{ij}^C$ is interatomic distance between i-th atom and j-th atom in the compound. $\alpha$ is a coefficient for making Sscore(i,j) the maximum value when the group of spatial points in the target protein and the compound completely overlap with each other. $\beta$ is a coefficient for giving a threshold value by which it can be defined as "overlapping".
(4) Make adjustment so that the score in (3) is maximum.
(5) Optimize interaction energy with the protein for the ligand superposed in (4) by fine adjustment of conformation.
(6) Largely change the conformation of the ligand, and restart from (2) and repeat the process up to (5) to achieve optimization.
(7) Conduct the course of (1) to (6) on the plurality of structural-change coordinates prepared in (0), and calculate an optimum protein-ligand complex coordinate and optimum energy "U optimum".
(8) Conduct the course of (1) to (7) on every ligand in the compound database prepared in (0), and select a ligand that has a possibility to bind to the protein from the compound database.

Also according to the ligand screening apparatus 100, when a parameter reflecting induced-fit of protein and a post-structural-change 3D structure coordinate are calculated by using a molecular dynamic calculation method, 3D structure of the target protein is subjected to normal mode calculation, intensity of fluctuation of each amino acid is determined, and molecular dynamic calculation is conducted using the intensity of fluctuation as a constraint condition. This realizes molecular dynamic calculation without causing large difference in 3D structure of the protein from the structure minimized by energy optimization "U hydrogen".

Also according to the ligand screening apparatus 100, as a target function for evaluation of interaction between ligand and protein, a function that expresses dynamic characteristics of a protein is added as elastic energy to a conventional interaction energy function, and interaction energy is rapidly calculated from the 3D structure coordinate of the protein, and physicochemical property concerning dynamic behavior of the protein is clearly described.

Also according to the ligand screening apparatus 100, as a function expressing dynamic characteristics of the protein, a result of normal mode analysis or a result of secondary structure determination of the protein is used.

Also according to the ligand screening apparatus 100, when the calculated protein has typical plural 3D structure coordinates, or plural 3D structural coordinates as is the case for analytical result of NMR spectrum, it is possible to evaluate all of the plural coordinates equally, in short time and full-automatically for screening for a ligand that binds to the target protein.

First Example

Determination of Parameter Coefficient in MD with Dihedral Angle Constrained and Clustering Using the ligand screening apparatus 100 according to the above embodiment, a fluctuation value of a dihedral angle was calculated by a normal mode analysis. As shown in this first example, a fluctuation value of the dihedral angle was adapted as a constraint condition in molecular dynamic calculation as "K dihedral angle" in the following formula.

$U$ dihedral angle=$K$ dihedral angle*$(\theta-\theta\text{equivalent})^2$ $\theta$ is the dihedral angle (unit: rad). In practice, an uneven constraint was applied to each dihedral angle such that it corresponds to fluctuation of the dihedral angle of a main chain within a range between a maximum value and a minimum value of "K dihedral angle" by designating such values. Accordingly, first example aims at determining appropriate maximum value and minimum value for "K dihedral angle". Further, after molecular dynamic calculation, post-structural-change coordinates were subjected to cluster analysis, and a representative structure was selected. At this time, for an active site that is designated in advance, active sites of structures obtainable by superposing receptors of every 100 femtoseconds during MD, and an active site of initial structure were considered as a population. Concretely, since dynamic information of side chain is easily lost by clustering, at first, side chain dihedral angles wherein dihedral angle χ of side chain is conserved within an average angle ±20.0 degrees in α % of the population are collected. However, when it is determined that χ closer to the main chain is not conserved, the subsequent χ is considered as not being conserved. Next, structures that satisfy the condition into every side chain dihedral angle (conserved side chain dihedral angle) in collected structure were extracted from the population. Then, to compare similarity of the extracted structures, when the rms (root mean square) of all atoms was β angstroms or less, it was regarded as the same structure, and one was deleted, and based on the finally selected structures, a receptor dynamic structure cluster was created. As to an atom forming unconserved dihedral angle χ, it was allowed to collide in the active site and ligand binding calculation because it was easy to change. α and β are constants, and the first example also aims at determining appropriate α and β.

The first example also aims at obtaining the best dynamic structure of a main chain in an active site being in contact with a ligand. For this purpose, in calculation of rms (root mean square), only four main chain atoms (N, Cα, C, O) in the active site were considered as objectives.

Supposing that as a maximum and a minimum values of K dihedral angle and clustering coefficients α and β, those capable of reproducing the structure analyzed by NMR are appropriate, first, we conducted normal mode analysis using MODEL 1 of dihydrofolate reductase (DHFR, PDB code: 1LUD) whose structure was analyzed to determine a fluctuation value by NMR, and then conducted molecular dynamic calculation. After the molecular dynamic calculation, we conducted clustering of receptor dynamic structure. Receptor residues located within 6 angstroms from each atom in the ligand contained in 1LUD (MODEL 1) were defined to form an active site. Further, for MD, results of 0 to 0.1 nanosecond were used. Here, MD was conducted exhaustively for constraint ranging from a minimum to a maximum value of 0 to 1000 (intervals of 100), clustering coefficient α ranging from 0% to 90% (intervals of 10%), coefficient 13 ranging from 0.1 angstrom to 0.6 angstrom (intervals of 0.1 angstrom) with reference to the NMR structure average rms, and coefficients were determined by comparing every result with the NMR structure in 1LUD.

As a reference for determining coefficient β in receptor dynamic structure clustering, NMR structure average value was determined. In NMR structures in PDB (the Protein Data Bank), receptor is a simple protein and in one PDB file more than ten patterns of NMR structures were found. We tried to determine a NMR structure average rms of active site for 117 kinds of substrates including a ligand.

First, in MODEL 1, receptor residues contained within 6 angstroms radius from each atom in the ligand were defined as forming an active site. Then for each structure other than MODEL 1, rms with respect to the active site of MODEL 1 was obtained, and then average rms thereof was determined. When the average rms is equal to or more than 1.0 angstrom, since it can be considered as an apparent dynamic structure, such a PDB file was excluded from the objective. As a result, objective PDB files were reduced to 71 kinds. Average rms of 71 kinds were further averaged to give NMR structure average rms. The NMR structure average rms obtained in this manner was 0.62.

As to determination of appropriate maximum and minimum values for "K dihedral angle" and determination of coefficients α and β in clustering, each parameter value was compared with NMR structure.

Since 1LUD includes 24 kinds of MODEL, and first example uses MODEL 1 as an objective, active sites of 23 kinds other than MODEL 1 were considered as true structures (observed experimentally). In each receptor dynamic structure cluster outputted as a result of calculation, rms between MODEL 1 and each true structure was calculated. The minimum rms among the calculated rms was set as "RMS minimum", and an average value of "RMS minimum" obtained from each receptor dynamic structure cluster was set as a score. Then a parameter at which the score is minimum was adopted.

Figure 11:
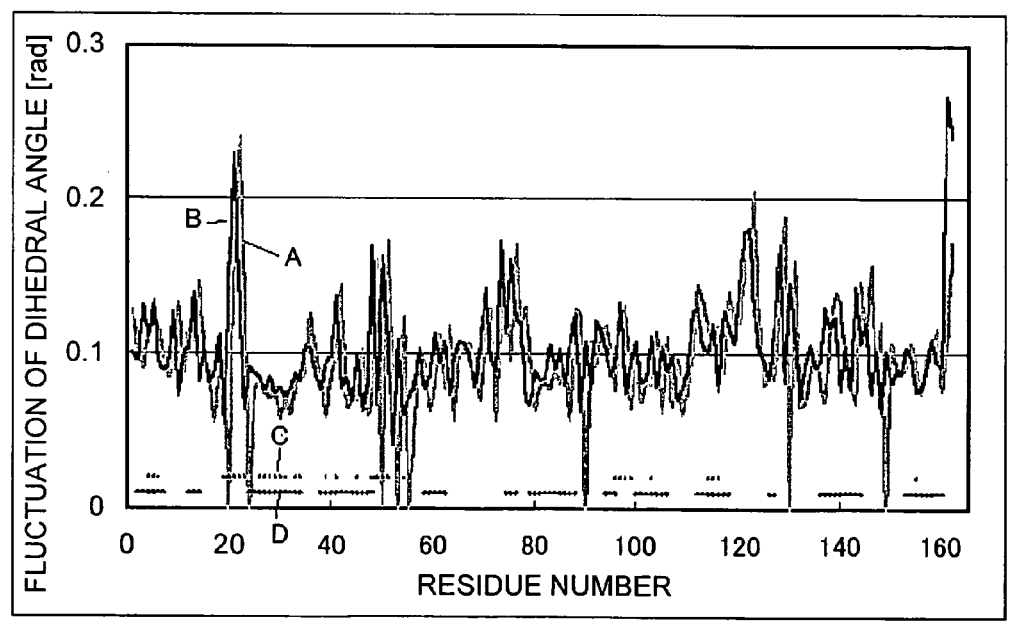
FIG. 11 is a view showing a result of normal mode analysis in MODEL 1 of 1LUD.

In FIG. 11, a result of normal mode analysis in MODEL 1 of 1LUD is shown, and comparison results of score and parameter are shown in FIGS. 12, 13, 15-18. In FIG. 11, intensity of fluctuation in dihedral angle φ (orange A), ψ (green B) is shown. The closer to 0.0 is intensity of the fluctuation, the stronger the constraint of dihedral angle becomes in the molecular dynamic (MD) calculation. Secondary structures determined by STRIDE are also shown: α-helix (red D) and β-sheet (blue D). The purple C shows an active site. In FIG. 12, the normal mode analysis demonstrated that coefficient α is preferably 70%. However, since there are cases that clustering accuracy was deteriorated at 70% when generalization was applied, in the first example, 80% was selected for a value of coefficient α. As shown in FIG. 13 and FIGS. 15-18, clustering coefficients α and β were fixed respectively at 80.0% and 0.4 angstroms. The score decreases as it becomes blacker.

Figures 13, 14:
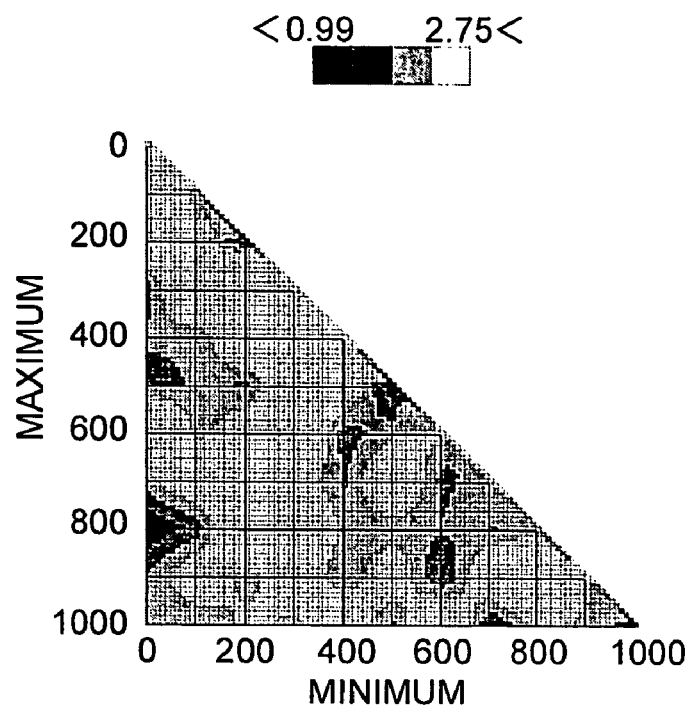
FIG. 13 is a view showing distribution of maximum value and minimum value of dihedral angle constraint in MD at a fixed clustering coefficient.
FIG. 14 is a view showing a constraint parameter.
Figure 15:
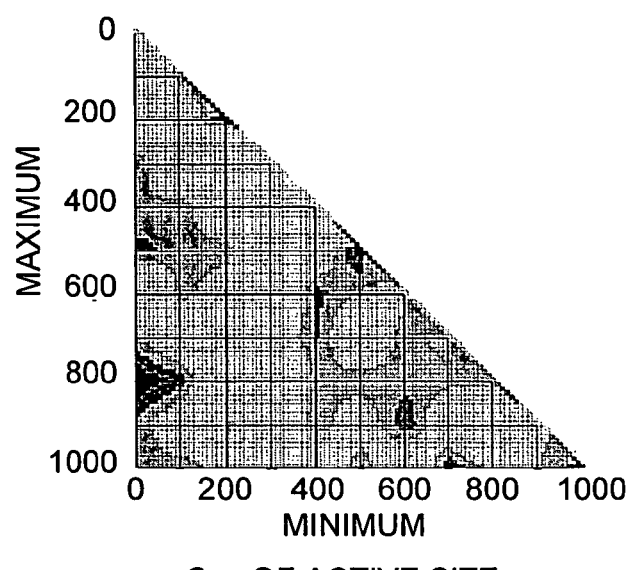
FIG. 15 is a view showing distribution of dihedral angle constraint parameters at a fixed clustering parameter.
Figure 16:
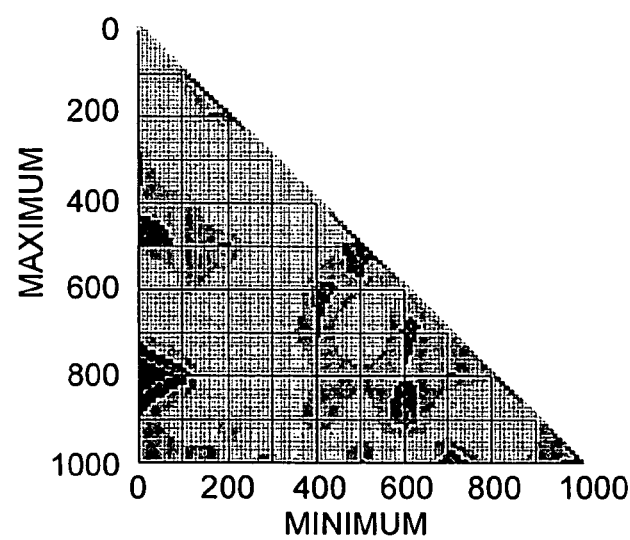
FIG. 16 is a view showing distribution of dihedral angle constraint parameters at a fixed clustering parameter.

These results demonstrated that the values of FIG. 14 are optimum as a constraint condition for reducing the score. As to validation of these values, Cα atom, side chain and all atoms besides the main chain atom were examined and the parameter values in FIG. 14 are proved to be optimum.

Second Example

Difference in Molecular Dynamic Calculation in the Presence/Absence of Constraint Parameters Molecular dynamic calculation adopting the constraint parameters calculated by the aforementioned ligand screening apparatus 100 was conducted until 2.0 nanoseconds. Then, how the structure changed in comparison with the case where the constraint parameters were not adopted in dynamic behavior of main chain atom in the active site was examined. Case 1)

Figure 19:
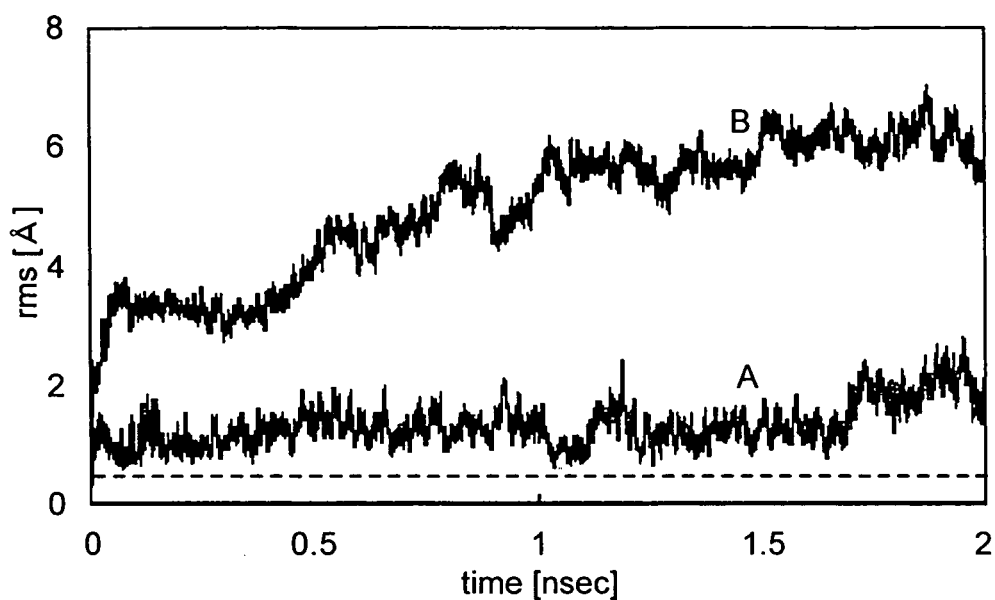
FIG. 19 is a view showing a result of MD of 1LUD (MODEL 1)
Figure 20:
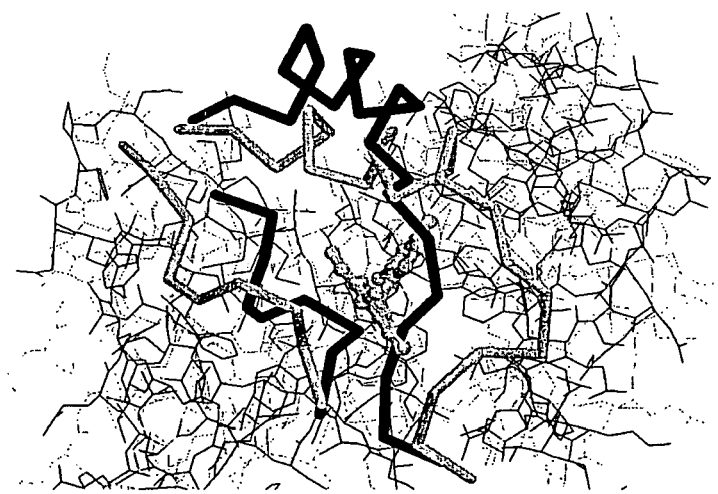
FIG. 20 is a view showing a result of comparison with a NMR structure when the MD is calculated without constraint of dihedral angle.
Figure 21:
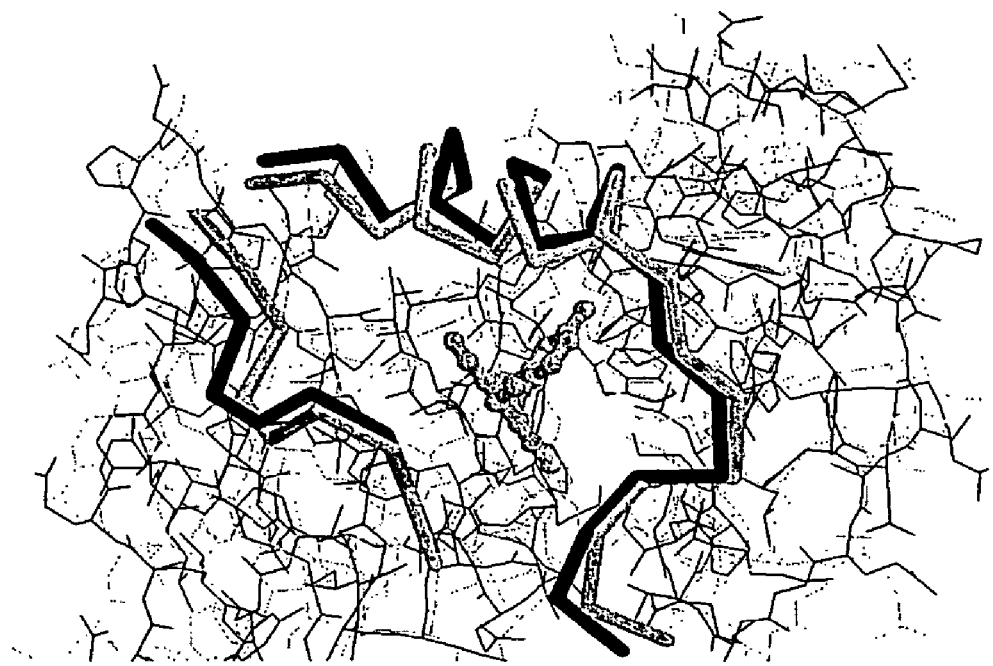
FIG. 21 is a view showing a result of comparison with a NMR structure when the MD is calculated with constraint of dihedral angle.

Examination was made on dihydrofolate reductase (MODEL 1 of 1LUD). Examination results are shown in FIGS. 19 to 21. As the result of normal mode calculation, values that were determined in the above first example were adapted.

In FIG. 19, with respect to MODEL 1 of each of 24 kinds of model structures described in PDB file of 1LUD, rms of a main chain atom in active site was calculated, and the average rms was displayed by dotted lines. In the case where dihedral angle is constrained (A), and in the case where dihedral angle is not constrained (B), a difference of the main chain atom in the active site from its initial structure was represented by rms.

FIG. 20 shows a comparison result with NMR structure when MD is calculated without constraint of dihedral angle. In FIG. 20, NMR structure (1lud) is displayed in white, MD structure (1lud) id displayed in black.

In Table 1, a comparison result with NMR structure when MD is calculated without constraint of dihedral angle is shown.

TABLE 1

|  | ACTIVE SITE | ENTIRETY |
| --- | --- | --- |
| Cα ONLY | 3.8903 | 0.2919 |
| MAIN CHAIN | 3.8642 | 0.3335 |
| ENTIRETY | 4.447 | 0.1398 RMS |

In FIG. 21, a comparison result with a NMR structure when MD is calculated with constraint of dihedral angle is shown.

In Table 2, a comparison result with a NMR structure when MD is calculated with constraint of dihedral angle is shown.

TABLE 2

|  | ACTIVE SITE | ENTIRETY |
| --- | --- | --- |
| Cα ONLY | 0.6398 | 0.1194 |
| MAIN CHAIN | 0.6933 | 0.1053 |
| ENTIRETY | 1.2379 | 0.2157 RMS |

Case 2)

Here, we verified dependency on initial structure and presence/absence of constraint while selecting a structure (model structure) obtained by modeling according to FAMS [Ogata K., Umeyama H. (2000) An automatic homology modeling method consisting of database searches and simulated annealing J. Mol. Graphics Mod. 18, 258-272], and X-ray structure as initial structures. Receptor residues contained within 10 angstroms radius from each atom in the ligand were defined as forming an active site.

Figure 23:
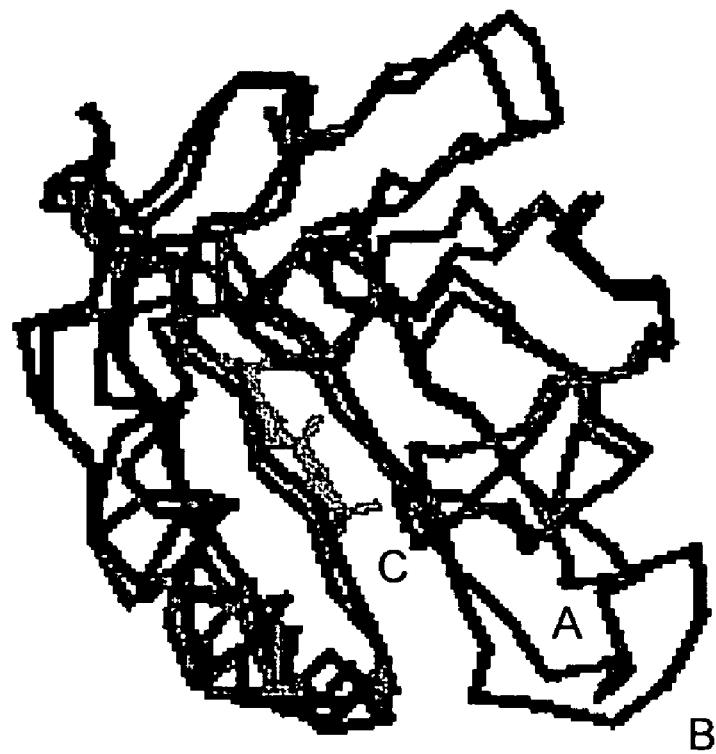
FIG. 23 is a view showing 3D structure of 1CBQ.
Figure 24:
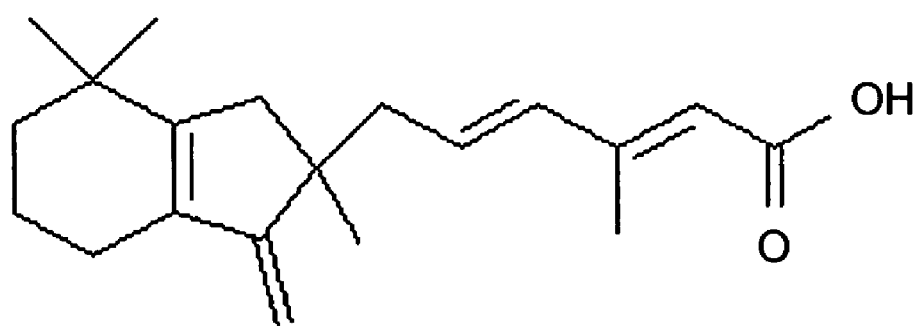
FIG. 24 is a view showing 3D structure of 1CBQ.

X-ray structure (3D structure) of cellular retinoic acid binding protein type II (CRABP-II) (PDB code: 1CBQ) was used. As a reference protein, intestinal fatty acid binding protein (PDB code: 1ICM) exhibiting 32.1% homology was selected, and a model structure was constructed by alignment of FIG. 22. In FIGS. 23, 24, and 25, results of X-ray structure comparison with model structure are shown.

In FIG. 23, 3D structure (X-ray structure (red A) and model structure (blue B)) of 1CBQ are shown. In FIG. 24, structure of 6-(2,3,4,5,6,7-hexahydro-2,4,4-trimethyl-1-methyleneinden-2-yl)-3-methylhexa-2,4-dienoic acid which is a substance shown in green in FIG. 23 is shown. In FIG. 25, difference between X-ray structure and model structure of 1CBQ is shown by rms.

Figure 26:
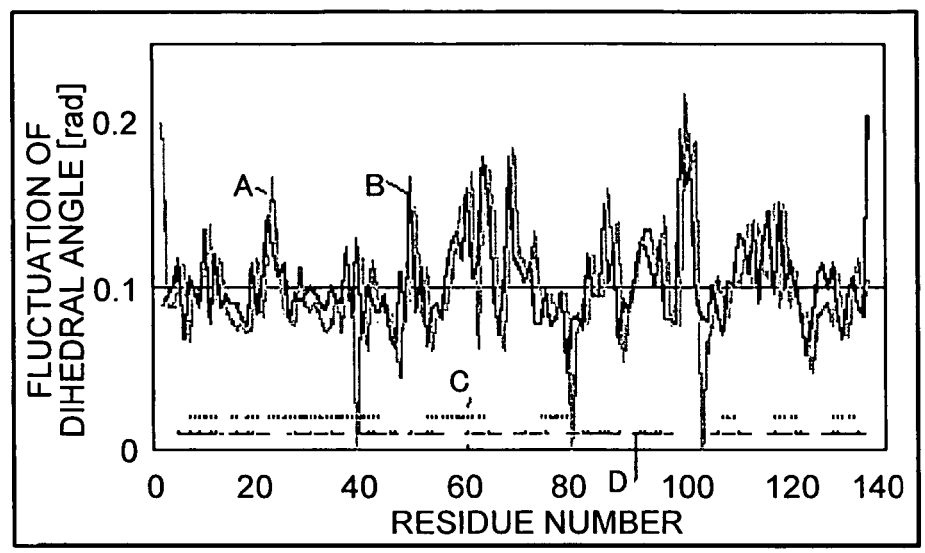
FIG. 26 is a view showing results of normal mode analysis for an X-ray structure and a model structure of 1CBQ.
Figure 27:
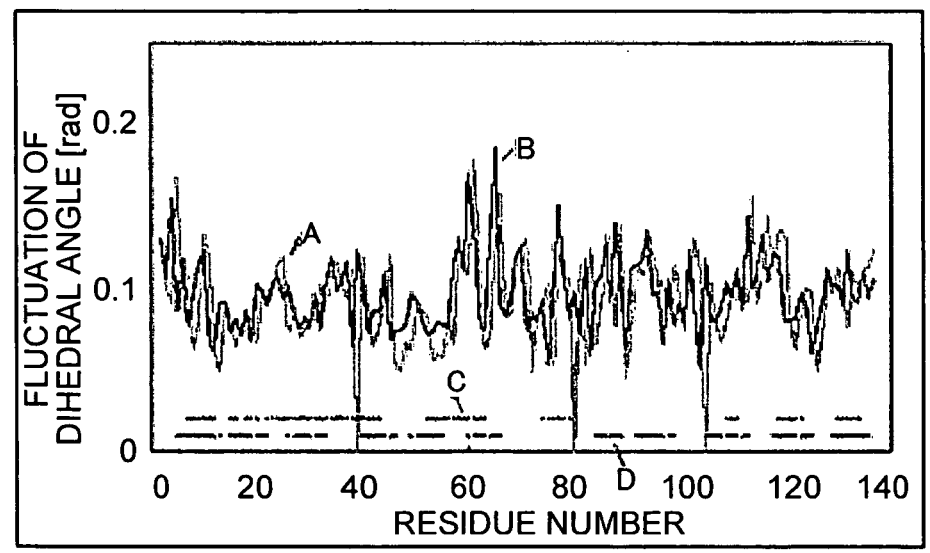
FIG. 27 is a view showing results of normal mode analysis for an X-ray structure and a model structure of 1CBQ.

FIG. 26 is a view showing a result of a normal mode analysis of X-ray structure of 1CBQ, and FIG. 27 is a view showing a result of normal mode analysis of model structure of 1CBQ. In FIG. 26 and FIG. 27, intensity of fluctuation in dihedral angle φ (orange A), ψ (green B) is shown. The closer to 0.0 is intensity of the fluctuation, the stronger the constraint of dihedral angle becomes in the molecular dynamic (MD) calculation. Secondary structures determined by STRIDE are also shown: α-helix (red D) and β-sheet (blue D).

Figure 28:
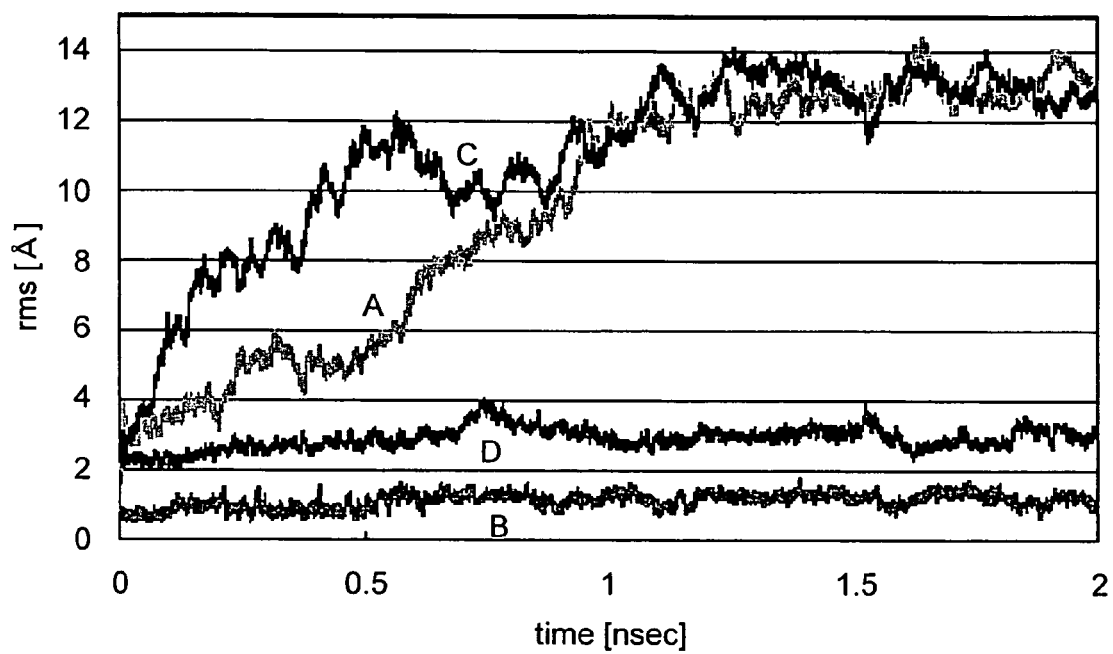
FIG. 28 is a view showing results of MD calculation for an X-ray structure and a model structure of 1CBQ.

In FIG. 28, results of molecular dynamic (MD) calculation of X-ray structure and model structure of 1CBQ are shown. Rms of a main chain atom in active site between X-ray structure and model structure was determined. As shown in FIG. 28, A: initial structure is X-ray structure, without constraint of dihedral angle; B: initial structure is X-ray structure, with constraint of dihedral angle; C: initial structure is model structure, without constraint of dihedral angle; and D: initial structure is model structure, with constraint of dihedral angle.

Case 3)

Figure 30:
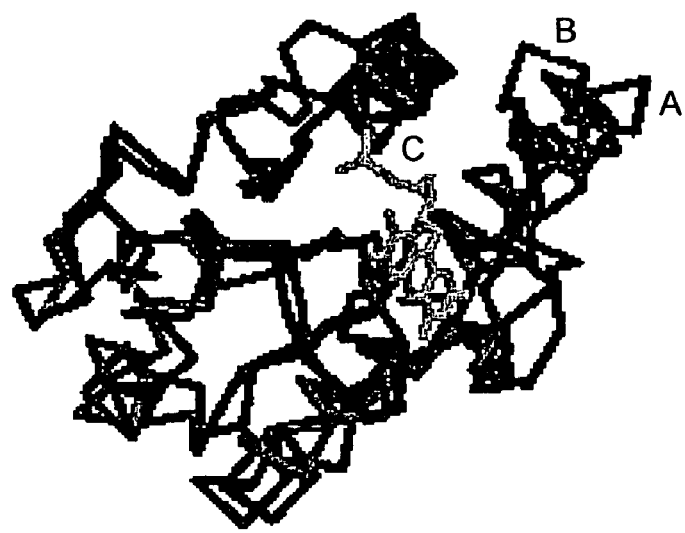
FIG. 30 is a view showing 3D structure of 1J9G.
Figure 31:
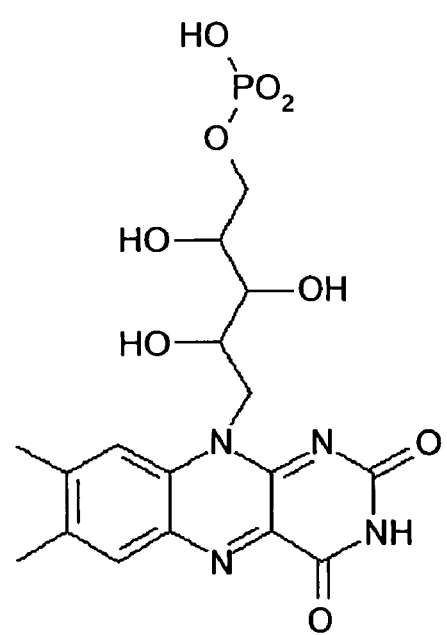
FIG. 31 is a view showing 3D structure of 1J9G.

X-ray structure of Flavodoxin (PDB code: 1J9G) was used. As a reference protein, flavodoxin (PDB code: 1AHN) exhibiting 29.2% homology was selected, and model structure was constructed by alignment of FIG. 29. In FIG. 29, alignments of 1J9G and 1AHN are shown. In FIG. 30, 3D structures (X-ray structure (red A) and model structure (blue B)) of 1J9G are shown. In FIG. 31, the structure of flavin mononucleotide which is a substance viewed in green C is shown in FIG. 30. In FIG. 32, the difference between X-ray structure and model structure of 1J9G is shown by rms.

Figure 33:
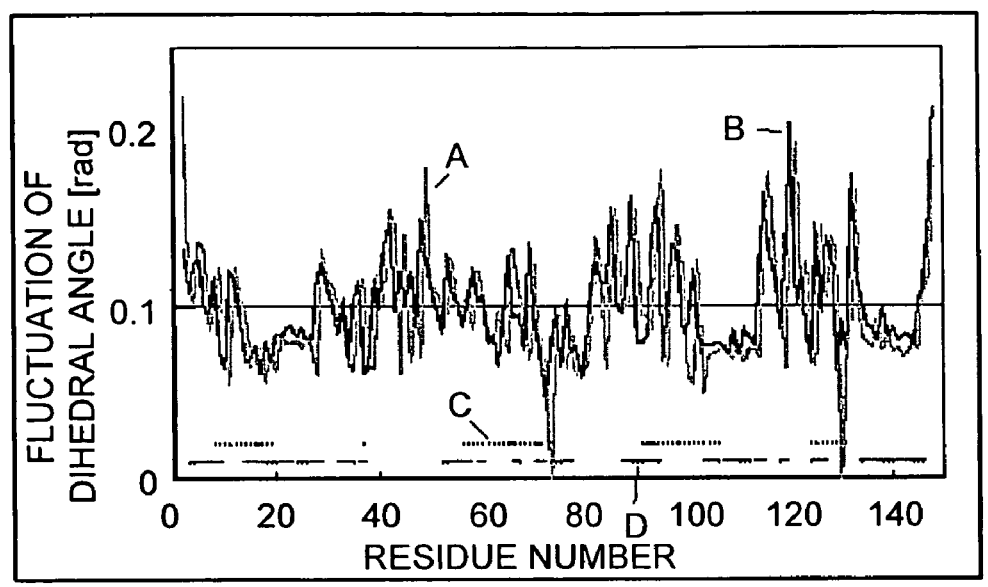
FIG. 33 is a view showing results of normal mode analysis for an X-ray structure and a model structure of 1J9G.
Figure 34:
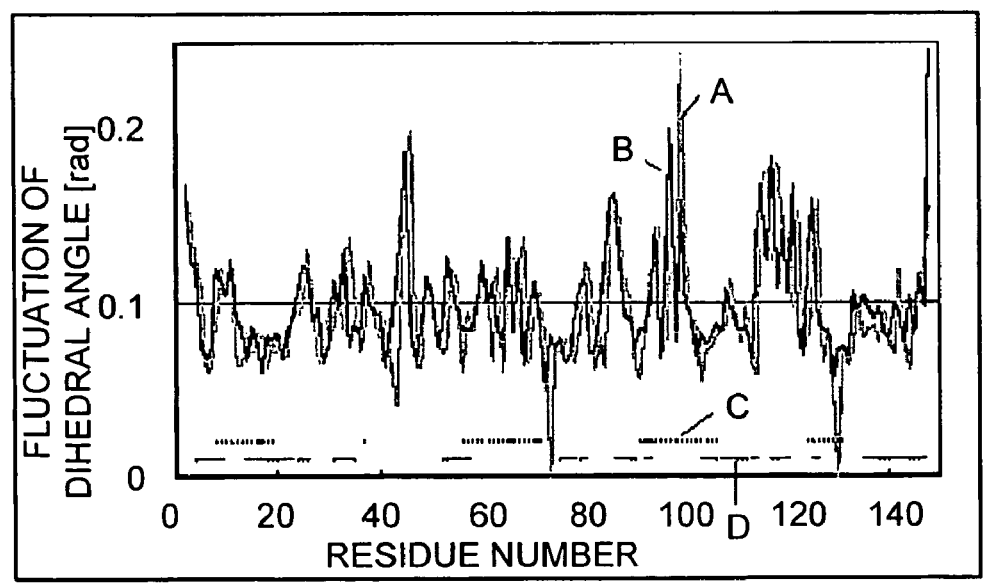
FIG. 34 is a view showing results of normal mode analysis for an X-ray structure and a model structure of 1J9G.

In FIG. 33, a result of normal mode analysis of X-ray structure of 1J9G, and in FIG. 34, a result of normal mode analysis of model structure of 1J9G are shown. In FIG. 33 and FIG. 34, intensity of fluctuation in dihedral angle φ (orange A), ψ (green B) is shown. The closer to 0.0 is intensity the fluctuation, the stronger the constraint of dihedral angle becomes in the molecular dynamic (MD) calculation. Secondary structures determined by STRIDE[8] are also shown: α-helix (red D) and β-sheet (blue D). The purple C shows an active site.

Figure 35:
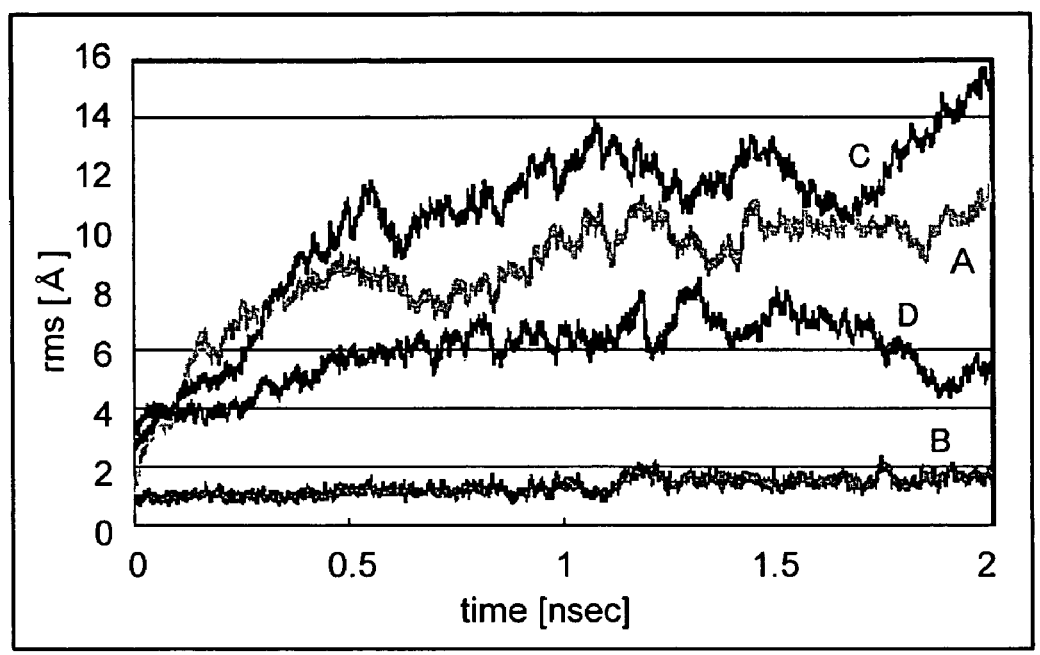
FIG. 35 is a view showing results of MD calculation for an X-ray structure and a model structure of 1J9G.

In FIG. 35, results of molecular dynamic (MD) calculation of X-ray structure and model structure of 1J9G are shown. Rms of a main chain atom in active site between X-ray structure and model structure was determined. In FIG. 35, A: initial structure is X-ray structure, without constraint of dihedral angle; B: initial structure is X-ray structure, with constraint of dihedral angle; C: initial structure is model structure, without constraint of dihedral angle; and D: initial structure is model structure, with constraint of dihedral angle.

Case 4)

X-ray structure of Matrix metalloproteinase-8 (MMP-8) (PDB code: 1MMB) was used. As a reference protein, MMP-3 (PDB code: 1B3D) exhibiting 55.0% homology was selected, and a model structure was constructed by alignment of FIG. 36. In FIG. 36, alignments of 1MMB and 1B3D_A are shown.

Figure 37:
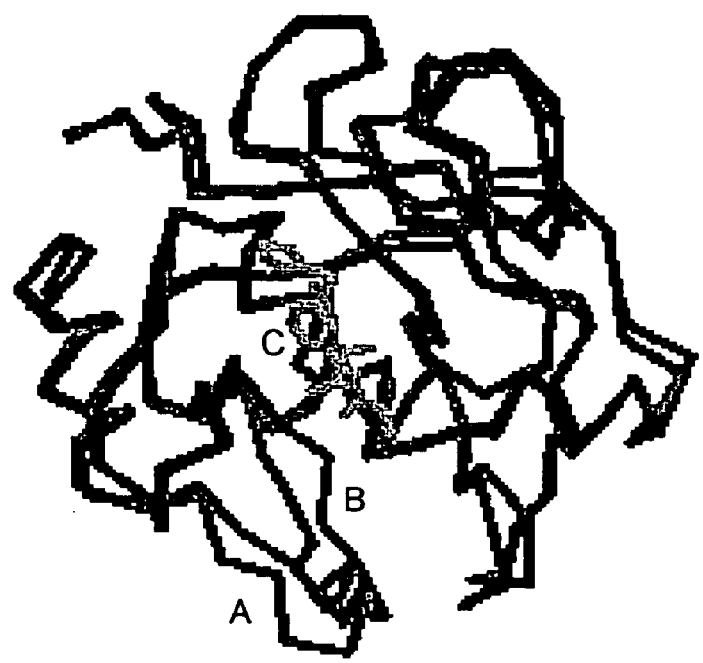
FIG. 37 is a view showing 3D structure of 1MMB.
Figure 38:
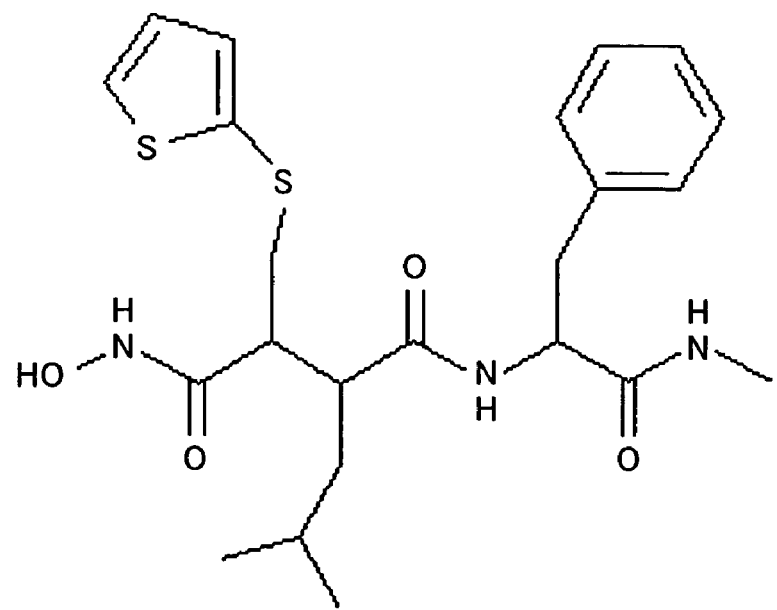
FIG. 38 is a view showing 3D structure of 1MMB.

In FIG. 37, 3D structures (X-ray structure (red A) and model structure (blue B)) of 1MMB are shown. In FIG. 38, structure of batimastat which is a substance viewed in green C is shown. In FIG. 39, the difference between X-ray structure and model structure of 1MMB is shown by rms.

Figure 40:
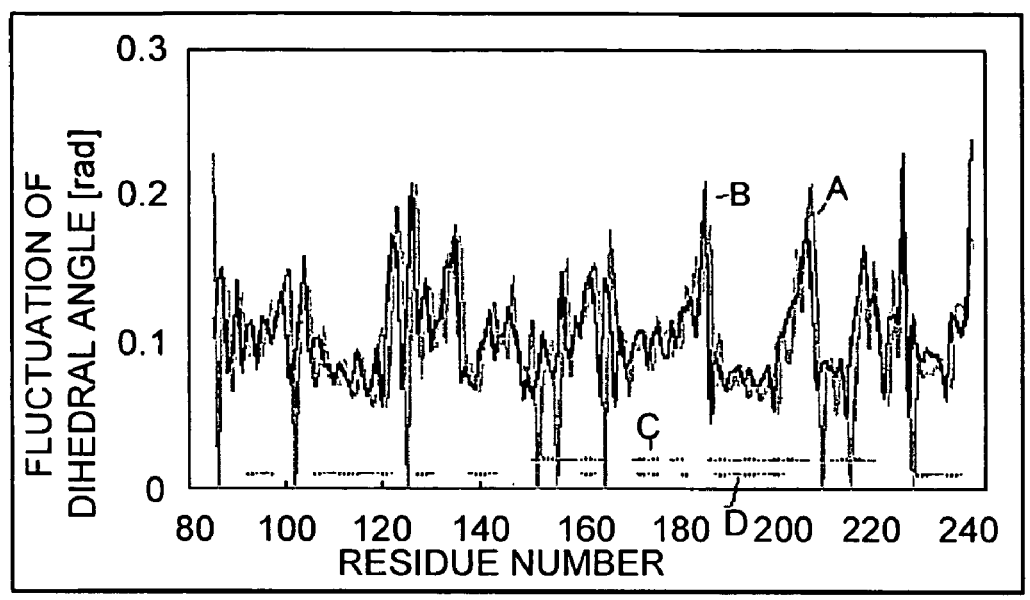
FIG. 40 is a view showing results of normal mode analysis for an X-ray structure and a model structure of 1J9G.
Figure 41:
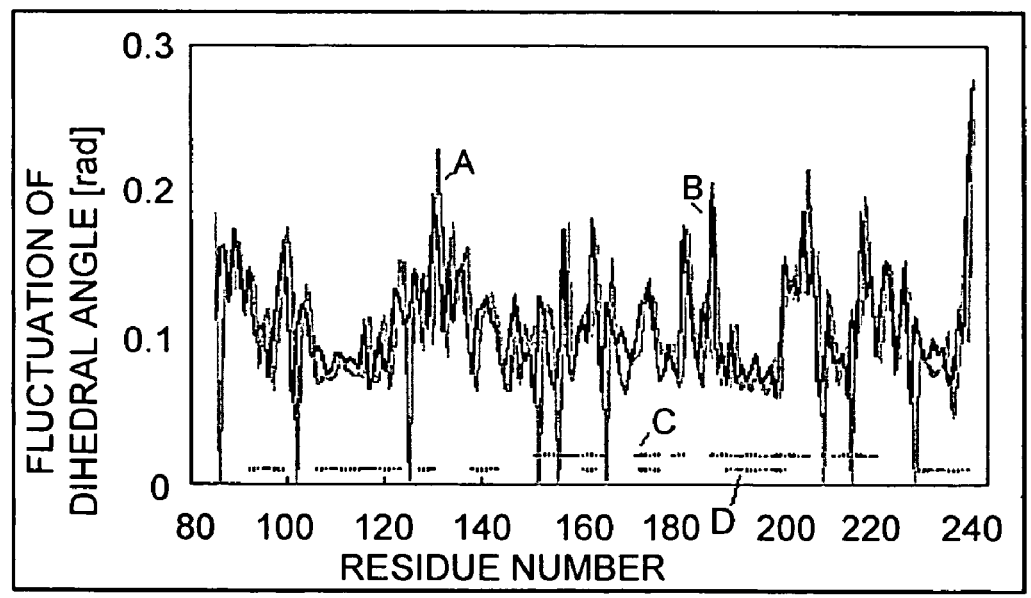
FIG. 41 is a view showing results of normal mode analysis for an X-ray structure and a model structure of 1J9G.

In FIG. 40, a result of a normal mode analysis of X-ray structure of 1MMB, and in FIG. 41, a result of normal mode analysis of model structure of 1MMB are shown. As shown in FIG. 40 and FIG. 41, intensity of fluctuation in dihedral angle φ (orange A), ψ (green B) is shown. The closer to 0.0 is intensity of the fluctuation, the stronger the constraint of dihedral angle becomes in the molecular dynamic (MD) calculation. Secondary structures determined by STRIDE[8] are also shown: α-helix (red D) and β-sheet (blue D). The purple C shows an active site.

Figure 42:
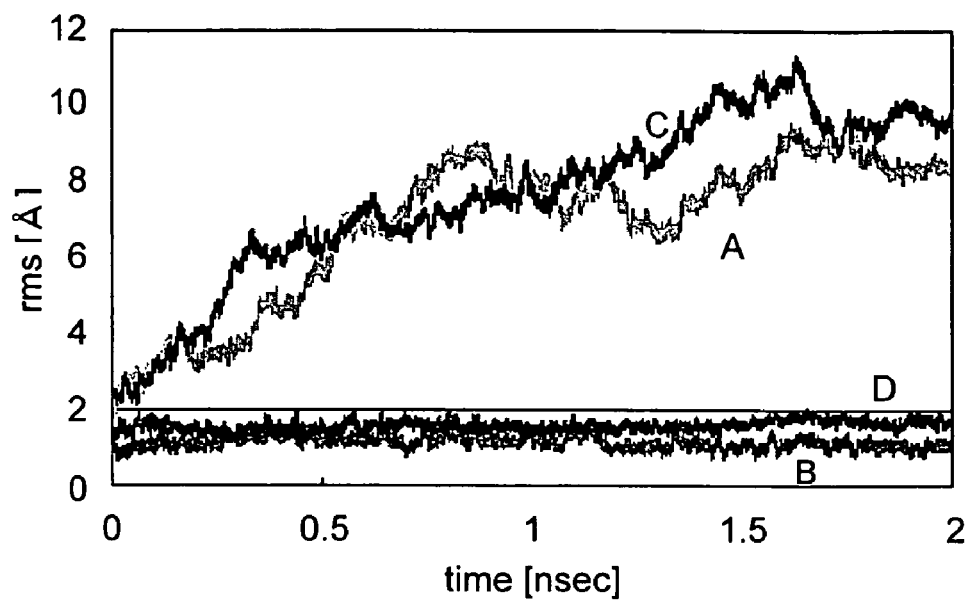
FIG. 42 is a view showing results of an MD calculation for an X-ray structure and a model structure of 1MMB.

In FIG. 42, results of molecular dynamic (MD) calculation of X-ray structure and model structure of 1MMB are shown. Rms of a main chain atom in active site X-ray structure and model structure was determined. As shown in FIG. 42, A: initial structure is X-ray structure, without constraint of dihedral angle; B: initial structure is X-ray structure, with constraint of dihedral angle; C: initial structure is model structure, without constraint of dihedral angle; and D: initial structure is model structure, with constraint of dihedral angle.

As shown in Cases 1) to 4), the result of molecular dynamic calculation adapting constraint parameters exhibit less significant structural change compared to the case where constraint parameters are not adapted. This reveals that significant structural change can be reasonably constrained and ideal structure coordinates can be obtained by adopting constraint parameters in a molecular dynamic method which results in large structural change due to theory of classical mechanics. When homology is high, the accuracy of modeled structure by FMAS is also improved. That is, since structure similar to X-ray structure is obtained, the present invention may be applied for mutation proteins substituted by several amino acids.

Third Example

Verification of Protein/Ligand Complex Model

By means of the ligand screening apparatus 100 in the above described embodiment, a 3D structure of a ligand complex that binds to the target protein was predicted. In the third example, prediction accuracy of the 3D structure coordinate of a complex was examined. For this verification, an induced-fit type protein was used, which a is known 3D structure of a complex and has variable conformation of the active site which varies depending on presence/absence of a ligand or a type of ligand. Residues located within a 10 angstrom radius from each atom in the ligand were defined to form an active site of the protein. Since it turned out that the structure is kept substantially equivalent in MD which uses X-ray structure or NMR structure as initial structure, we decided to conduct MD until 1.0 nanosecond. In the calculation, however, hydrogen atoms were excluded. Construction of a complex model was conducted in accordance with the above embodiment.

Case 1)

Figure 43:
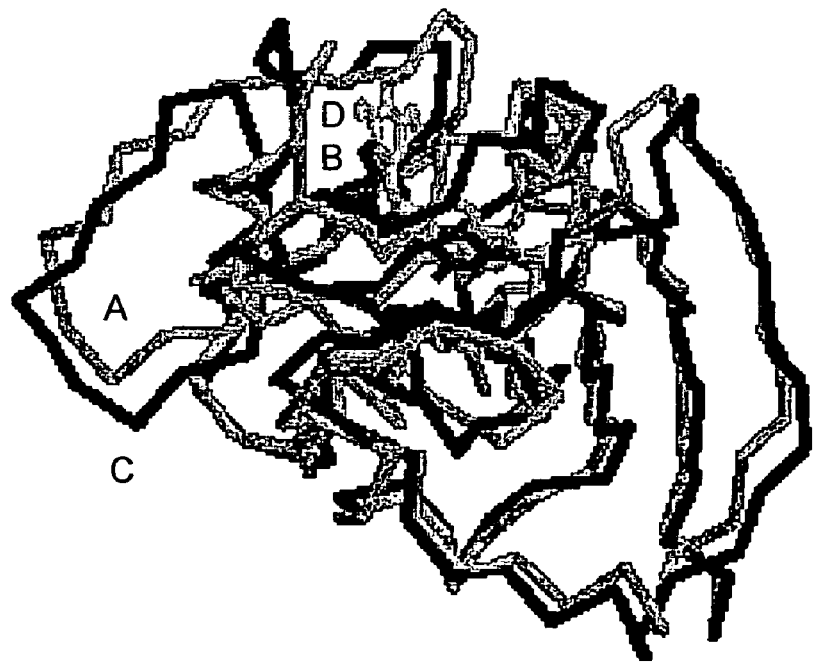
FIG. 43 is a view showing a 3D structure of dihydrofolate reductase.

1BZF and 1LUD, dihydrofolate reductase (DHFR) have 100% homologous but are different conformations of active site because separate ligands bind to protein. 1BZF (MODEL 18) was selected as an initial structure, and using 2,4-diamino-5-(3,4,5-trimethoxy-benzyl)-pyrimidin-1-ium (FIG. 49), a protein/ligand complex model was created by the ligand screening apparatus 100 in the embodiment as described above, and examination was made by comparison with 1LUD (MODEL 4) which is the true structure (FIG. 43). In FIG. 43, 3D structure of dihydrofolate reductase was shown. In FIG. 43, receptor (green A) and ligand (red B) of 1LUD (MODEL 4), as well as receptor (blue C) and ligand (light blue D) of 1BZF (MODEL 18) were shown.

Figure 44:
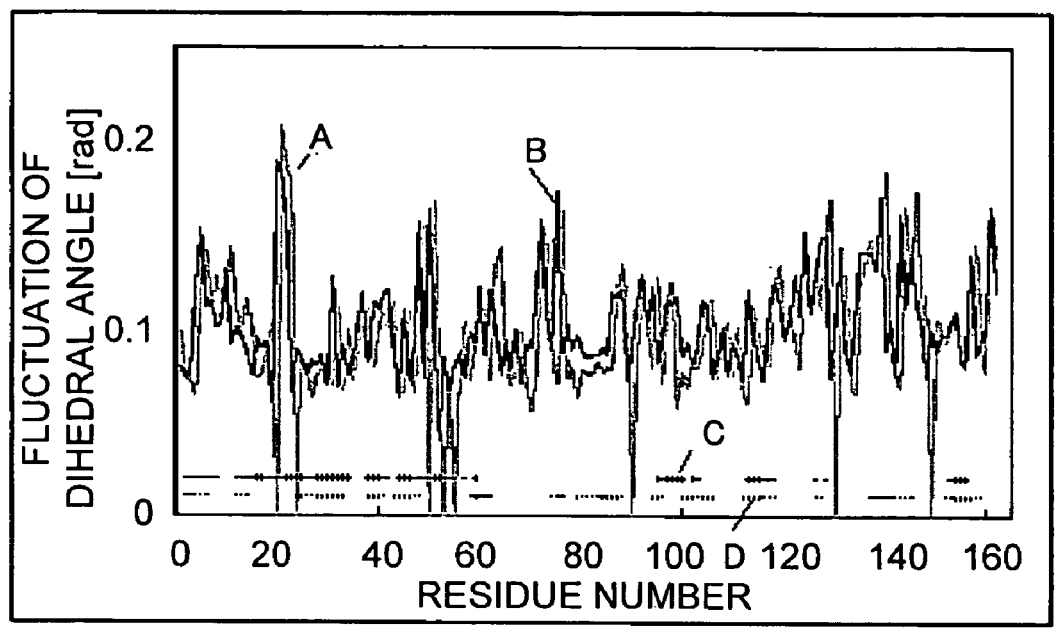
FIG. 44 is a view showing a result of normal mode analysis of 1BZF (MODEL 18)

In FIG. 44, analysis results of normal mode calculation of 1BZF was shown. In FIG. 44, intensity of fluctuation in dihedral angle φ (orange A), ψ (green B) is shown. The closer to 0.0 is intensity of the fluctuation, the stronger the constraint of the dihedral angle becomes in the molecular dynamic (MD) calculation. Secondary structures determined by STRIDE are also shown: α-helix (red D) and β-sheet (blue D). The purple C shows an active site.

Figure 45:
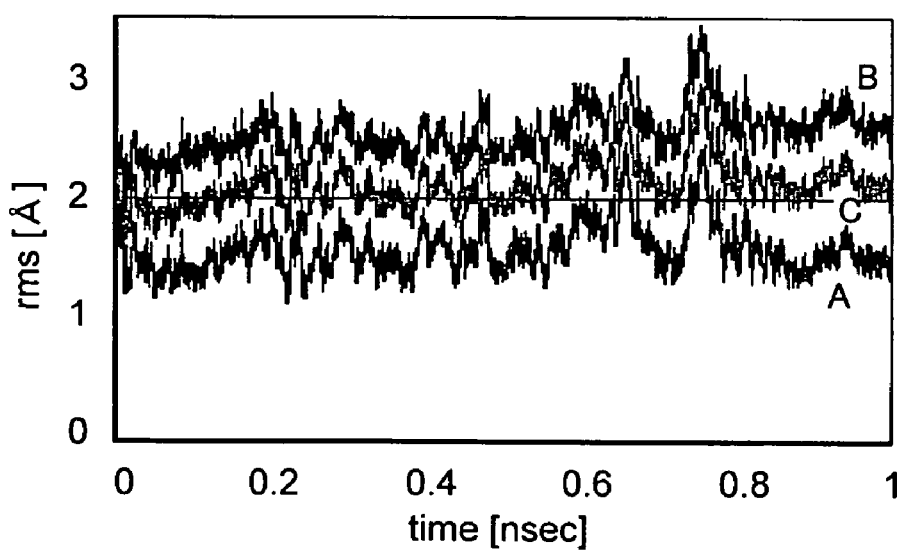
FIG. 45 is a view showing a result of an MD calculation of 1BZF (MODEL 18)

In FIG. 45 and FIG. 47, results of molecular dynamics with dihedral angle constrained of 1BZF were shown. In FIG. 45, rms with true structure, 1LUD (MODEL 4) in the active site is shown. In FIG. 45, A is of the main chain atom, B is of the side chain atom, and C is of the whole atom. FIG. 47 is a result of analysis of ligand binding to active site in 1BZF (MODEL 18). These are results of binding analyses when MD calculation was effected until 0.1 or 1.0 nanosecond, and dynamic structures of receptor are extracted at interval of 100 femtoseconds in the former and 100 and 1000 femtoseconds in the latter, three separate populations are created by clustering those. Evaluation was made based on rms with true structure of ligand in active site. In FIG. 46, parameter values for designating spatial points in ligand docking are shown. FIG. 46 shows information of structure-activity relationship obtained from 1LUD (MODEL 4).

Figure 48:
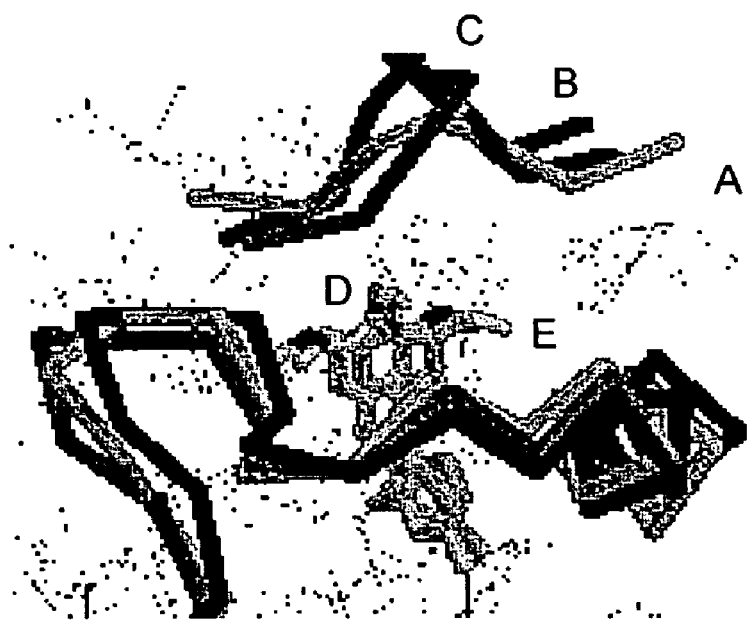
FIG. 48 is a view showing 1BZF (MODEL 4)-ligand binding.
Figure 49:
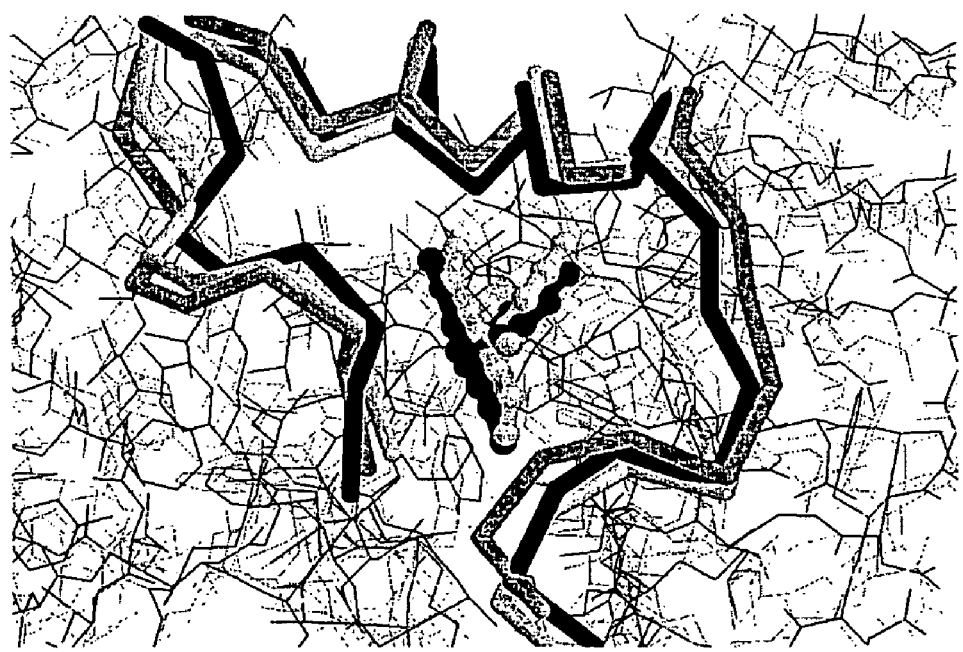
FIG. 49 is a view showing 1BZF (MODEL 4)-ligand binding.
Figure 50:
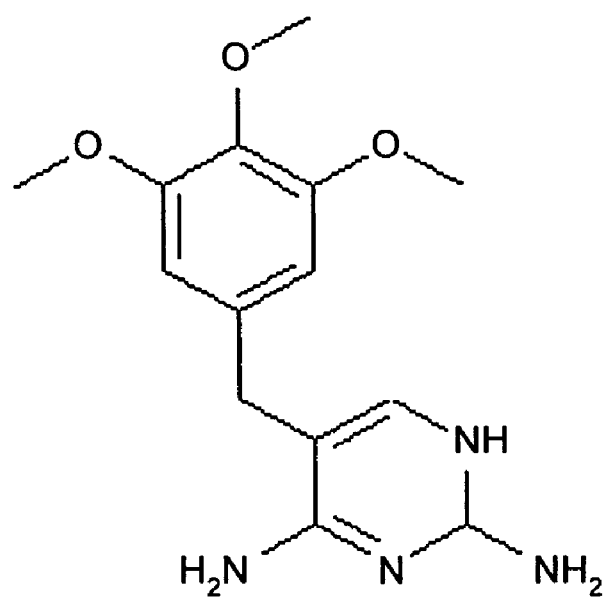
FIG. 50 is a view showing 1BZF (MODEL 4)-ligand binding.

In FIGS. 48 to 50, comparisons between protein/ligand complex and true structure are shown. FIG. 48 shows binding between an active site and a ligand using a population created by clustering dynamic structure of receptors after those were extracted at interval of 100 femtoseconds within 0-1.0 nanosecond in the MD. Green A shows 1LUD (MODEL 4) in true structure, blue B shows 1BZF (MODEL 18) in initial structure, and red C shows optimum structure in ligand binding, "by element" color D shows ligand in true structure; and light blue E shows ligand by calculation result. Rms of ligand was 0.9614. By causing the ligand shown in FIG. 50 to bind, induction of 0.2791 by rms occurred in the main chain atom in the active site. In FIG. 49, true structure (model 4 of 1LUD) is shown in black, initial structure (model 18 of 1BZF) is shown in gray, and optimum structure is shown in white. FIG. 50 shows 2,4-diamino-5-(3,4,5-trimethoxy-benzyl)-pyrimidin-1-ium, which is a ligand of 1LUD.

Case 2)

Figure 51:
FIG. 51 is a view showing 3D structure of heat shock protein 90.

1YER and 1YET, heat shock protein 90 (HSP90) have 100% homologous but are different conformations of the active site because separate ligands bind to the protein. Selecting 1YER which does not bind to a ligand as initial structure, and using geldanamycin as a ligand, examination was made by comparison with 1YET which is true structure (FIG. 51). In FIG. 51, 3D structure of heat shock protein 90 is shown. Receptor (green A) and ligand (red B) of 1YET and receptor (blue C) of 1YER are shown.

Figure 52:
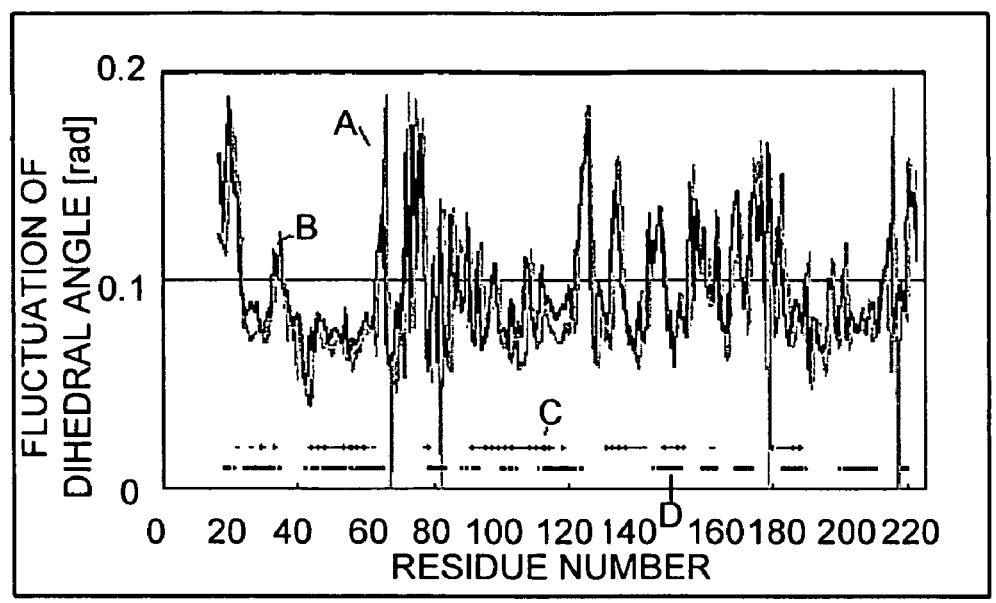
FIG. 52 is a view showing a result of normal mode analysis of 1YER.

In FIG. 52, result of normal mode analysis of 1YER is shown. In FIG. 52, intensity of fluctuation in a dihedral angle φ (orange A), ψ (green B) is shown. The closer to 0.0 is the intensity of the fluctuation, the stronger the constraint of the dihedral angle becomes in the molecular dynamic (MD) calculation. Secondary structures determined by STRIDE are also shown: α-helix (red D) and β-sheet (blue D). The purple C shows an active site.

Figure 53:
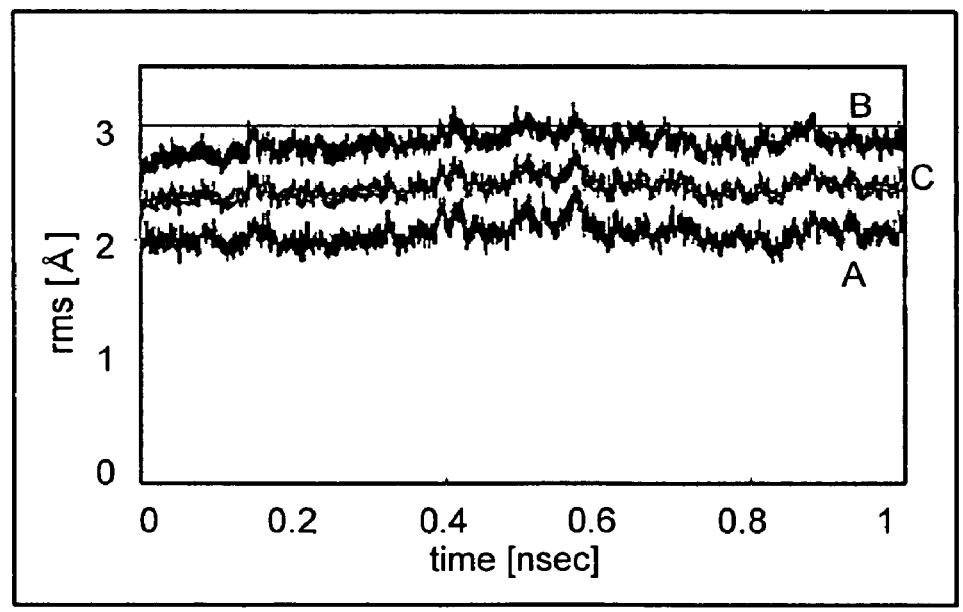
FIG. 53 is a view showing a result of MD calculation of 1YER.

In FIG. 53 and FIG. 55, results of molecular dynamics with the dihedral angle constrained using 1YER are shown. Rms with true structure, 1YET in the active site is shown. A is of the main chain atom, B is of the side chain atom, and C is of the whole atom. FIG. 55 is a result of analysis of a ligand binding to an active site in 1YER. These are results of binding analyses when MD calculation was effected until 0.1 or 1.0 nanosecond, and dynamic structure of receptor are extracted at interval of 100 femtoseconds in the former and 100 and 1000 femtoseconds in the latter, and the sepalate populations are created by clustering those. Evaluation was made based on rms with the true structure of the ligand in the active site. In FIG. 54, parameter values for designating spatial points in ligand docking are shown. FIG. 54 shows information of structure-activity relationship obtained from 1YET.

Figure 56:
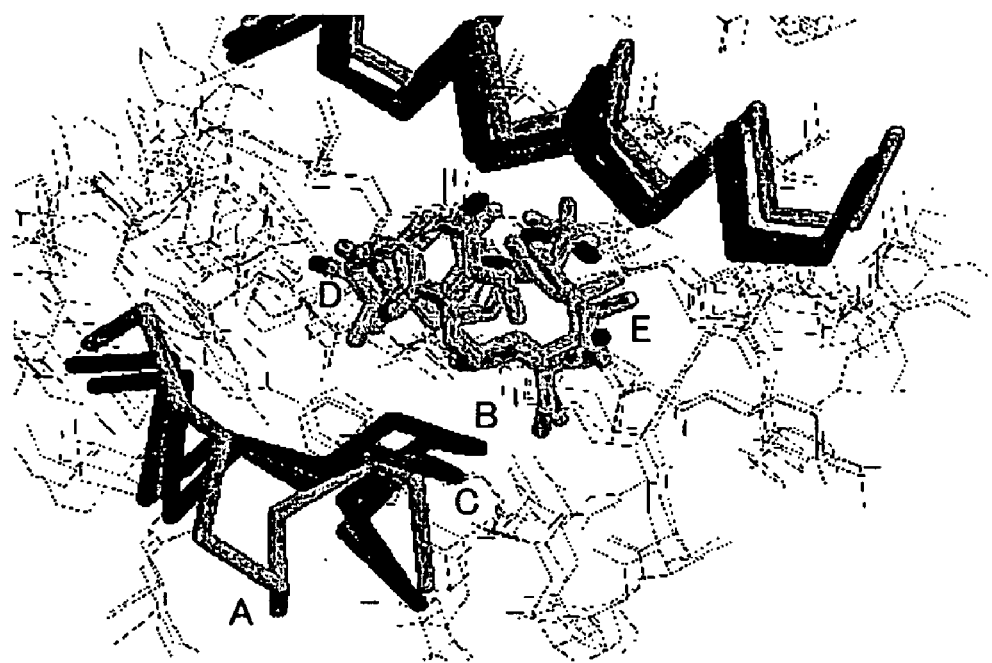
FIG. 56 is a view showing 1YER-ligand binding.
Figure 57:
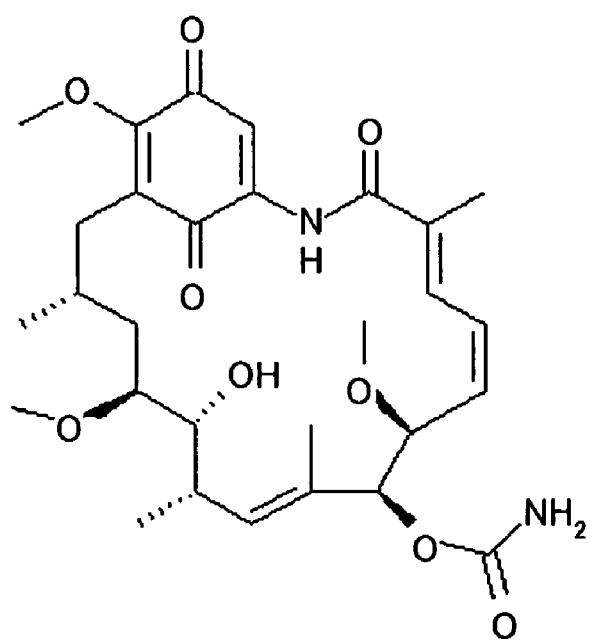
FIG. 57 is a view showing 1YER-ligand binding.

In FIGS. 56 and 57, a comparison between a protein/ligand complex and true structure is shown. FIGS. 56 and 57 show binding of the ligand in 1YER. FIG. 56 shows binding analysis between an active site and the ligand using a population created by clustering dynamic structure of receptors after those were extracted at interval of 100 femtoseconds within 0-1.0 nanosecond in the MD. Green A shows 1YET in true structure, blue B shows 1YER in initial structure, and red C shows optimum structure in ligand binding, "by element" color D shows ligand in true structure; and light blue E shows ligand by calculation result. Rms of ligand was 1.2081. By causing the ligand shown in FIG. 57 to bind; induction of 0.1619 by rms occurred in the main chain atom in the active site. FIG. 57 shows geldanamycin which is a ligand of 1YET.

Case 3)

Figure 58:
FIG. 58 is a view showing 3D structure of mitogen-activated protein kinase.

1A9U and 1OUK, mitogen-activated protein kinase (MAP kinase), have 100% homologous but are different conformations of active site because separate ligands bind to a protein. Selecting 1A9U as initial structure, and using a ligand contained in 1OUK as a ligand, examination to compare with true structure of ligand in 1OUK was made (FIG. 58). In FIG. 58, 3D structure of mitogen-activated protein kinase is shown. Receptor (green A) and ligand (red B) of 1OUK and receptor (blue C) and ligand (light blue D) of 1A9U are shown.

Figure 59:
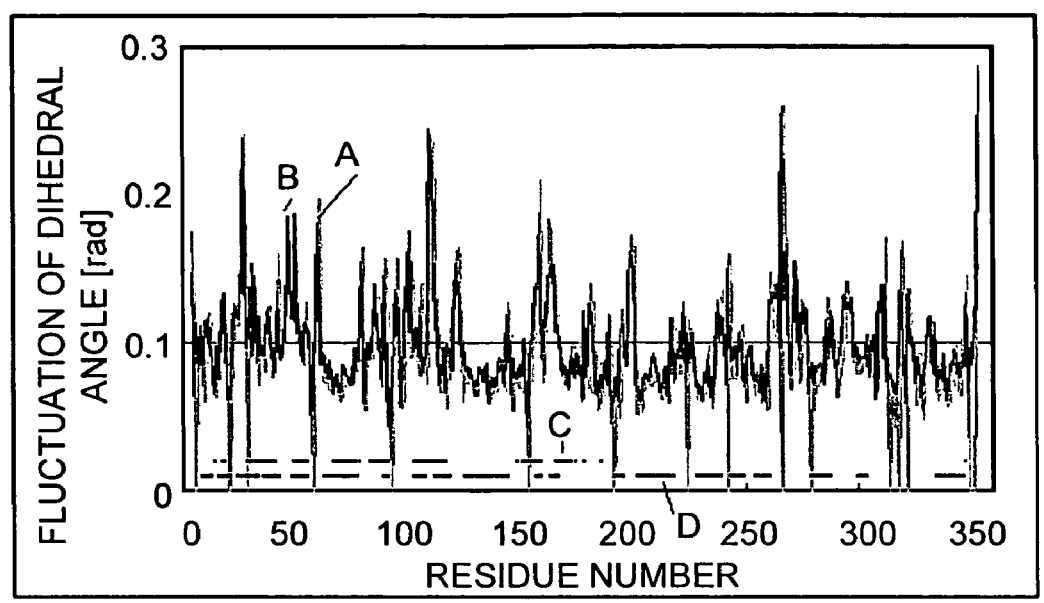
FIG. 59 is a view showing a result of normal mode analysis of 1A9U.

In FIG. 59, normal mode calculation analysis of 1A9U is shown. In FIG. 59, intensity of fluctuation in dihedral angle φ (orange A), ψ (green B) is shown. The closer to 0.0 is the intensity of the fluctuation, the stronger the constraint of the dihedral angle becomes in the molecular dynamic (MD) calculation. Secondary structures determined by STRIDE are also shown: α-helix (red D) and β-sheet (blue D). The purple C shows an active site.

Figure 60:
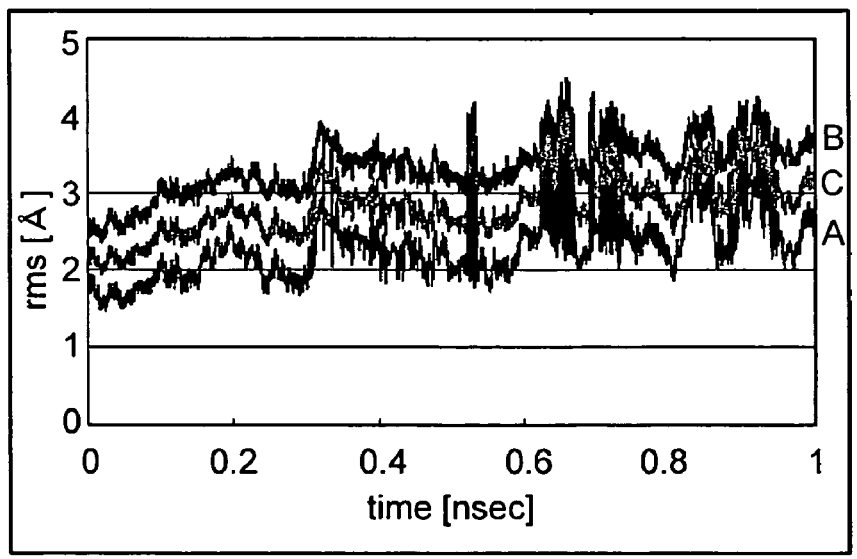
FIG. 60 is a view showing a result of MD calculation of 1A9U.

In FIG. 60 and FIG. 62, results of molecular dynamics with the dihedral angle constrained using 1YER are shown. FIG. 60 shows a result of MD calculation of 1A9U. Rms with true structure, 1OUK in the active site is shown in FIG. 60. A is of main chain atom, B is of side chain atom, and C is of whole atom. FIG. 62 shows a result of analysis of ligand binding to active site in 1A9U. These are results of binding analyses when MD calculation was effected until 0.1 or 1.0 nanosecond, and dynamic structures of receptor were extracted at interval of 100 picoseconds in the former and 100 and 1000 picoseconds in the latter, and three separate populations were created by clustering those. Evaluation was made based on rms with the true structure of the ligand in the active site.

In FIG. 61, parameter values for designating spatial points in ligand docking are shown. FIG. 61 shows information of structure-activity relationship obtained from 1OUK.

Figure 63:
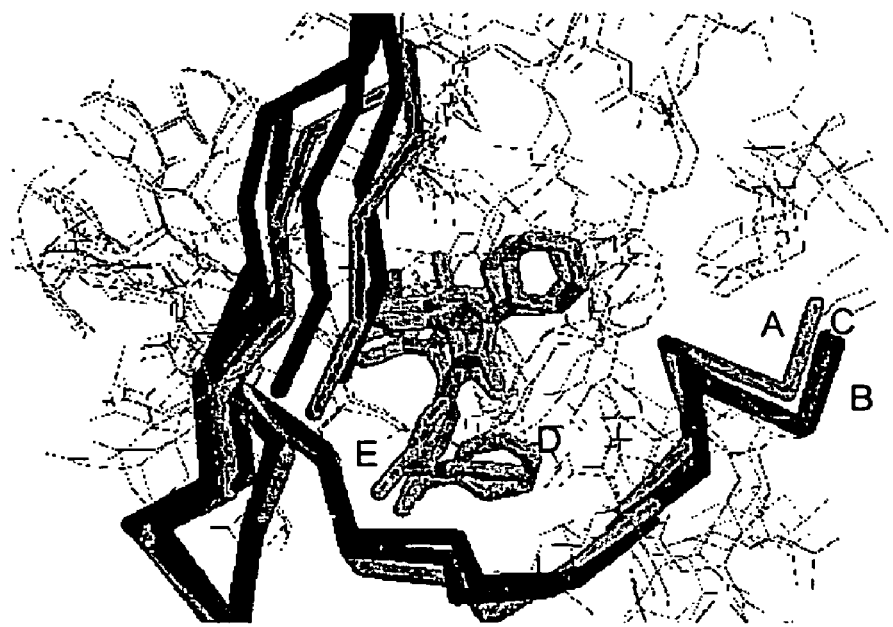
FIG. 63 is a view showing 1A9U-ligand binding.
Figure 64:
FIG. 64 is a view showing 1A9U-ligand binding.
Figure 65:
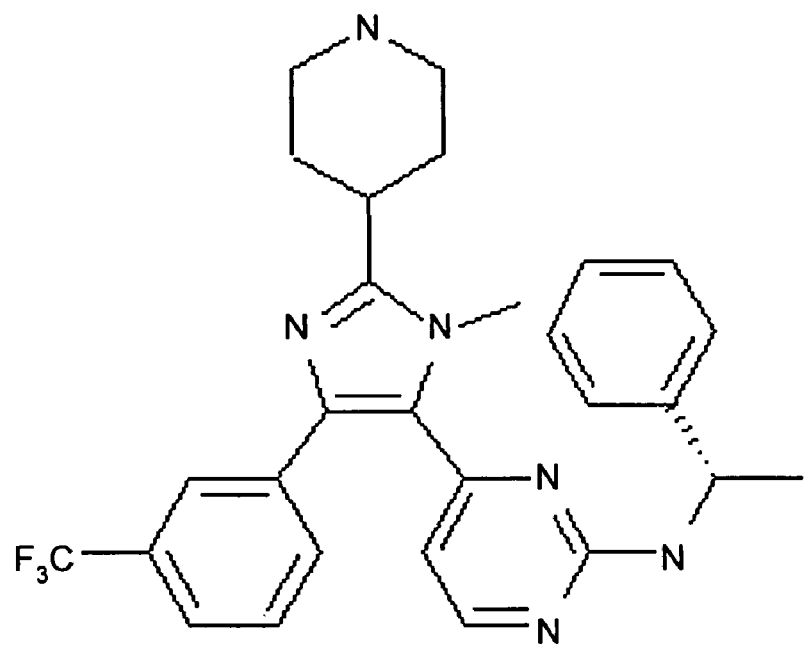
FIG. 65 is a view showing 1A9U-ligand binding.

FIGS. 63 to 65 show a comparison between a protein/ligand complex and a true structure. FIGS. 63 to 65 show binding of a ligand in 1AU9. FIG. 63 shows binding analysis between the active site and the ligand using a population created by clustering dynamic structures of receptors after those were extracted at an interval of 100 femtoseconds within 0-1.0 nanosecond in the MD. Green A shows 1OUK in true structure, blue B shows 1A9U in initial structure, and red C shows optimum structure in ligand binding, "by element" color D shows ligand in true structure; and light blue E shows ligand by calculation result. Rms of ligand was 1.6112. By causing the ligand shown in FIG. 65 to bind, induction of 0.1871 by rms occurred in the main chain atom in the active site. In FIG. 64, true structure (1OUK) is shown in black, initial structure (1A9U) is shown in gray, and optimum structure is shown in white. FIG. 65 shows 4-[5-[2-(1-phenylethylamino)-pyrimidin-4-yl]-1-methyl-4-(3-trifluoromethylphenyl)-1H-imidazol-2-yl]-piperidine which is a ligand of 1OUK.

As shown in Cases 1) to 3), it was proved that a model of a protein/ligand complex created by the ligand screening apparatus 100 can predict 3D structure of induced-fit type protein/ligand complex with high accuracy.

Fourth Example

Application Example to in Silico Screening Using Fxa

Figure 66:
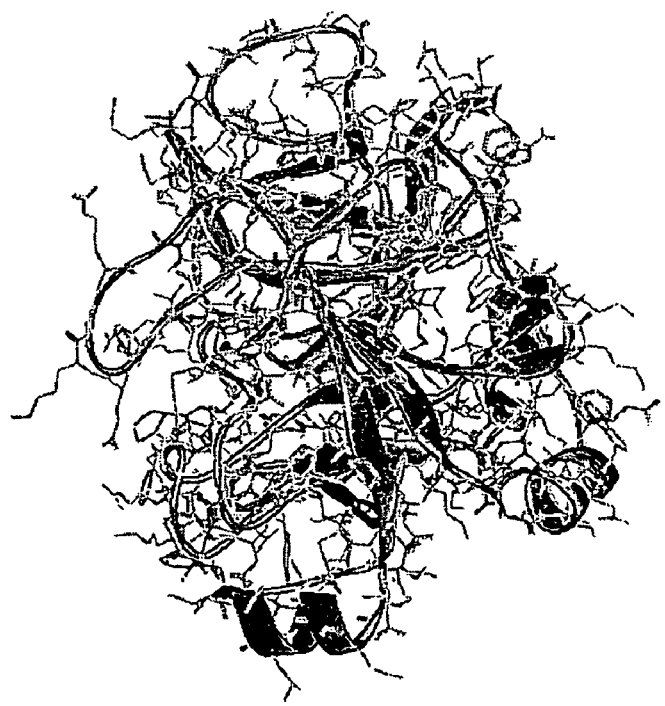
FIG. 66 is a view showing 3D structure of 1AIX.

By the ligand screening apparatus 100 in the above embodiment, a ligand having a possibility to bind to Fxa was screened from the compound database using a 3D structure of Fxa (FIG. 66) which is one kind of serine protease. As 3D structure, 1AIX was used, and as a ligand database, 3633 kinds of ligands extracted from the PDB database was used. In accordance with the above embodiment, in silico screening was conducted. The results are shown in FIG. 67.

In FIG. 67, ligands to 100th from the top of interaction energy to 1AIX among the ligands in the compound database are shown. In FIG. 67, the bold character is a ligand contained in 1AIX, the italic character is serine protease. "PDB code" means code of PDB in which the ligand is originally contained. In FIG. 67, a ligand originally contained in 1AIX ranks 19th.

Figure 68:
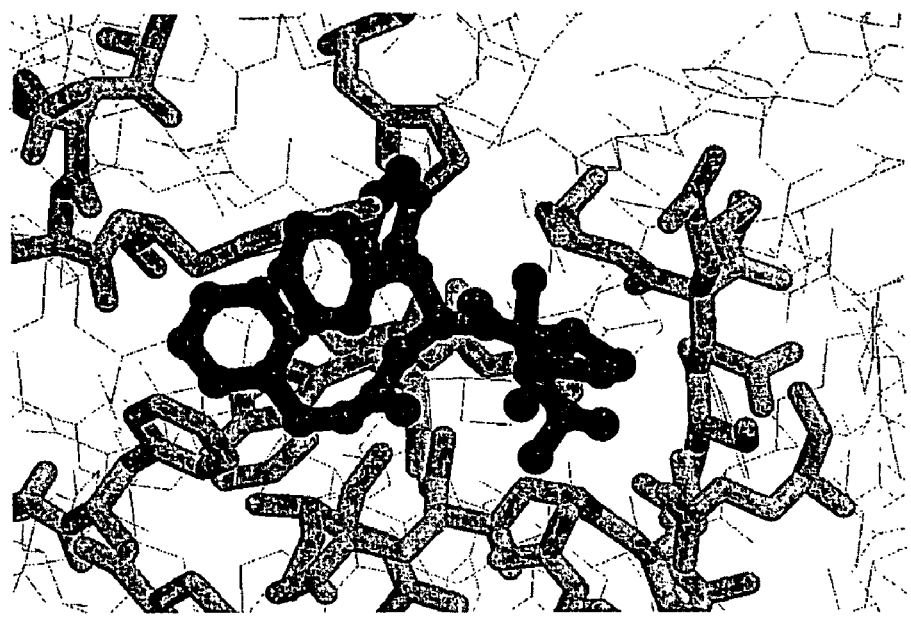
FIG. 68 is a view showing a protein/ligand complex structure.
Figure 69:
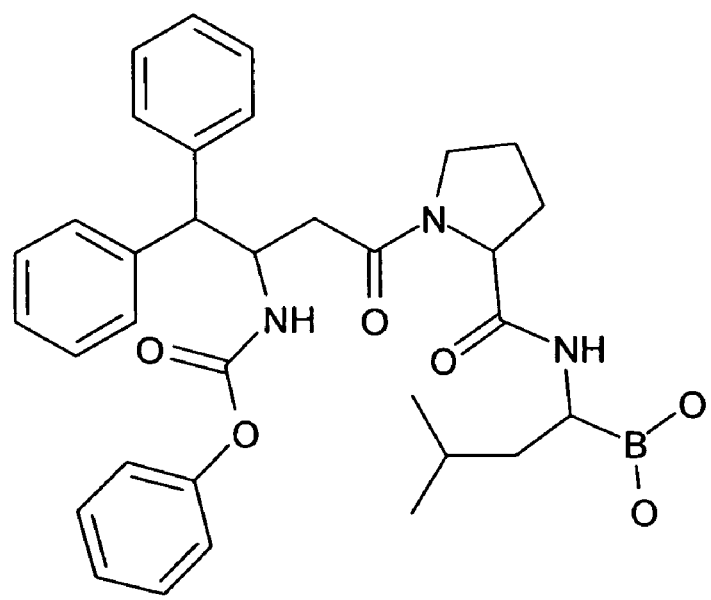
FIG. 69 is a view showing a protein/ligand complex structure.

A protein/ligand complex structure in 19th ranking is shown in FIG. 68 and FIG. 69. In FIG. 68, receptor is shown in white, and ligand of 1AIX is shown in black. FIG. 69 shows a ligand in 1AIX.

Every ligand in 35th, 38th and 80th rankings in FIG. 67 bind to serine protease.

Figure 70:
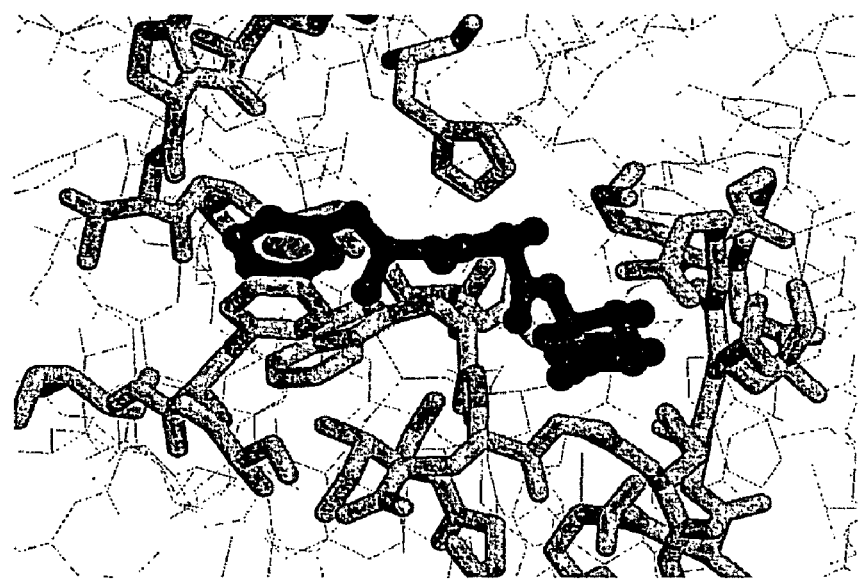
FIG. 70 is a view showing a protein/ligand complex structure.
Figure 71:
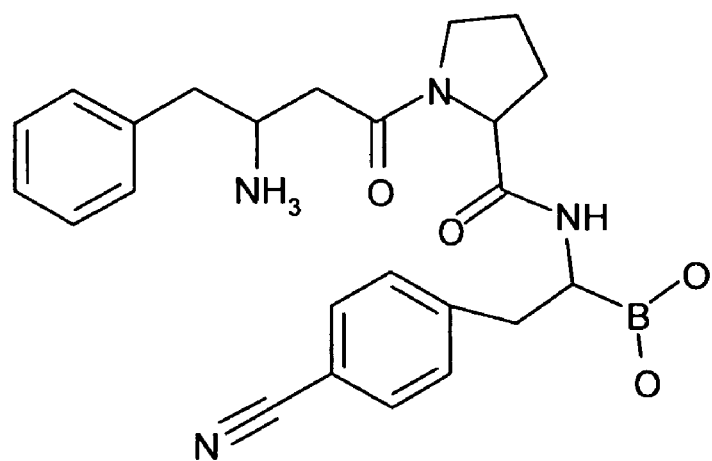
FIG. 71 is a view showing a protein/ligand complex structure.
Figure 72:
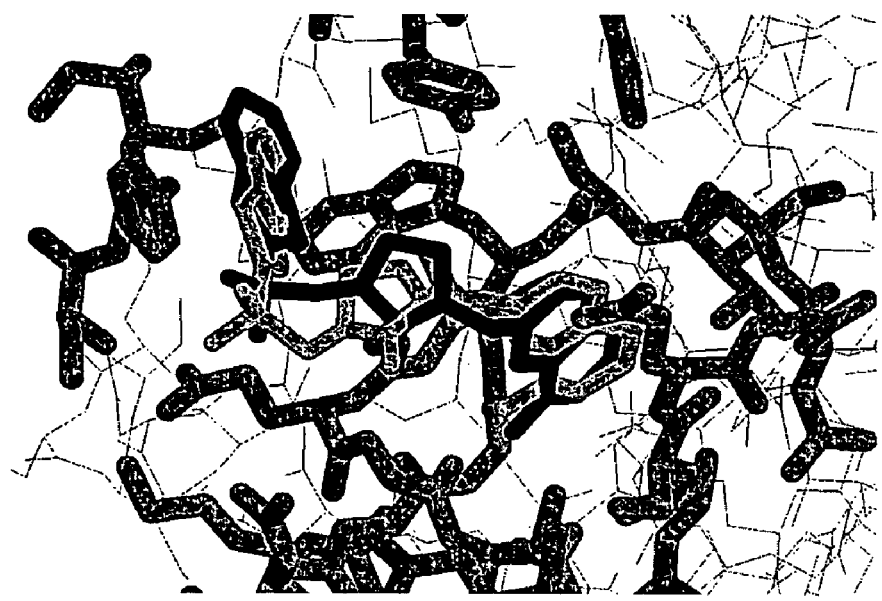
FIG. 72 is a view showing a protein/ligand complex structure.
Figure 73:
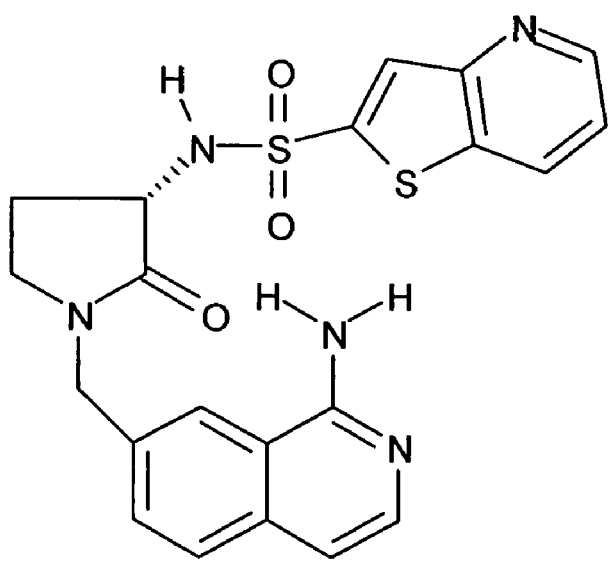
FIG. 73 is a view showing a protein/ligand complex structure.
Figure 74:
FIG. 74 is a view showing a protein/ligand complex structure.
Figure 75:
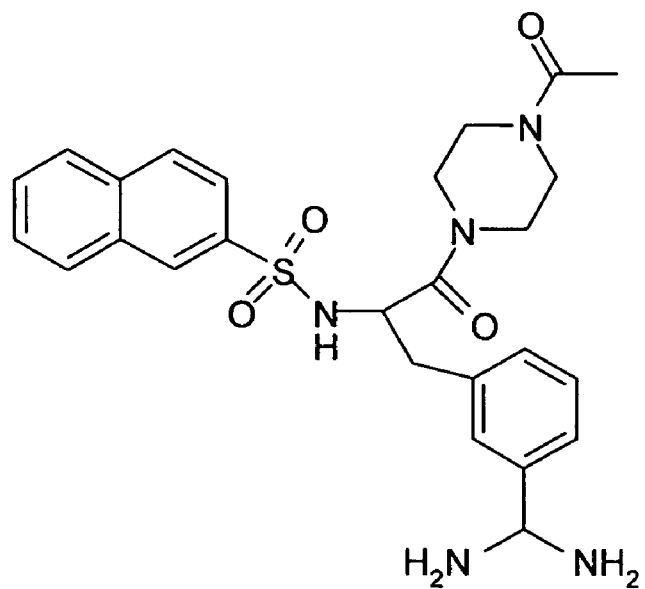
FIG. 75 is a view showing a protein/ligand complex structure.

These structures and protein/ligand complex structures are shown in FIG. 70 and FIG. 71, FIG. 72, FIG. 73, FIG. 74, and FIG. 75. In FIG. 70 and FIG. 71, a structure of a protein/ligand complex in 35th ranking is shown. In FIG. 70, a receptor is shown in white, and a ligand of 1AUJ is shown in black. FIG. 71 shows a ligand in 1AUJ. FIG. 72 and FIG. 73, structures of a protein/ligand complex in 38th ranking is shown. In FIG. 72, receptor is shown in white, and true ligand (1FOR) is shown in black. The rms was 1.500. FIG. 73 shows a ligand in 1FOR. In FIG. 74 and FIG. 75, structures of a protein/ligand complex in 80th ranking are shown. As shown in FIG. 74, receptor is shown in white, and ligand of 1K1M is shown in black. FIG. 75 shows a ligand in 1K1M.

These results revealed that feasible compounds can be selected from the compound database according to the present invention.

Fifth Example

In Silico Screening Under Different Conditions

We verified that the ranking varies depending on the information of the structure-activity relationship (SAR) by the ligand screening apparatus 100 in the above embodiment. We verified variation in ranking when the receptor is fixed.

Here, we executed in silico screening using protease of severe acute respiratory syndrome (SARS). As an initial structure, 1UK3 (B chain) not containing a ligand, and a binding mode of 1UK4 (B chain) including a ligand was used as information of a structure-activity relationship. The active site is a receptor residue region contained within 10 angstrom radius from each atom in the ligand of 1UK4 (B chain). As a ligand database, 3633 kinds of ligands collected from PDB were used. As a receptor dynamic structure cluster for use in binding analysis, the population assembling the structure extracted at an interval of 100 femtoseconds within the range of 0-0.1 nanosecond was used. The calculation was conducted with the exclusion of hydrogen atoms.

Figure 76:
FIG. 76 is a view showing a 3D structure of SARS protease.

FIG. 76 shows 3D structure of SARS protease. Receptor (green A) and ligand (red B) of IUK4 (B chain), as well as receptor (blue C) of 1UK3 (B chain) are shown.

Figure 77:
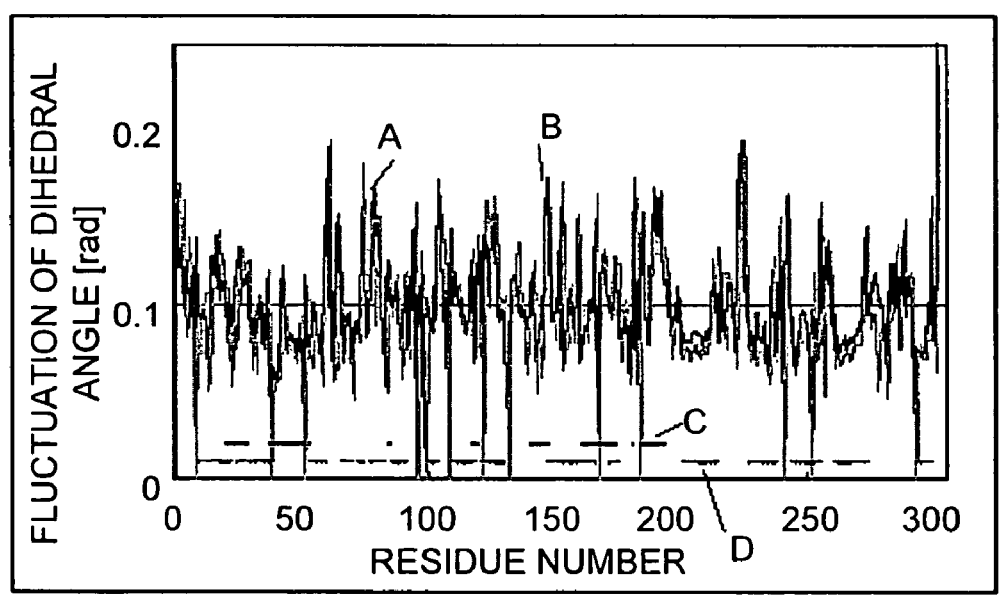
FIG. 77 is a view showing a result of normal mode analysis of 1UK3 (B chain)

In FIG. 77, a result of normal mode analysis of 1UK3 (B chain) is shown. Also intensity of fluctuation in a dihedral angle φ (orange A), ψ (green B) is shown. The closer to 0.0 is intensity of the fluctuation, the stronger the constraint of the dihedral angle becomes in the molecular dynamic (MD) calculation. Secondary structures determined by STRIDE are also shown: α-helix (red D) and β-sheet (blue D). The purple C shows an active site.

Figures 78, 79:
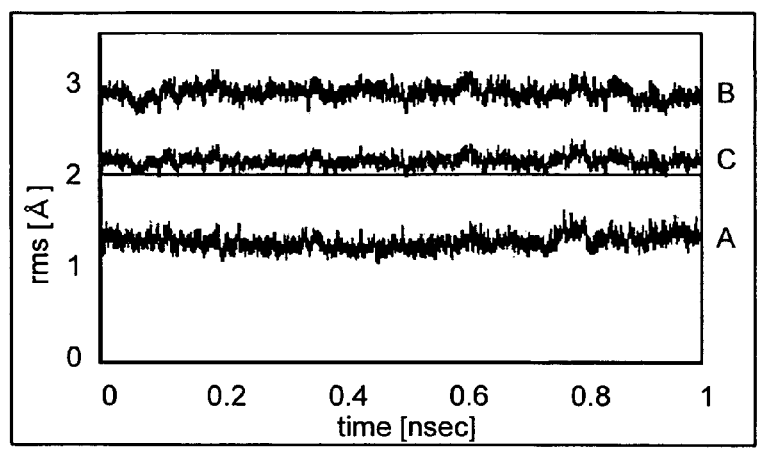
FIG. 78 is a view showing a result of MD calculation of 1UK3 (B chain)
FIG. 79 is a view showing structure-activity relationship information obtained from 1UK4 (B chain)

In FIG. 78, a result of molecular dynamic calculation of 1UK3 is shown. FIG. 78 shows rms between MD result of 1UK3 (B chain) and 1UK4 (B chain) in the active site. A is of the main chain atom, B is of the side chain atom, and C is of the whole atom.

Case 1) Designating Four Points in SAR

FIG. 79 shows spatial point designating within active sites of 1UK4. FIG. 79 shows structure-activity relationship information obtained from 1UK4 (B chain). In FIG. 80, a result of in silico screening in 1UK3 (B chain) is shown.

Figure 81:
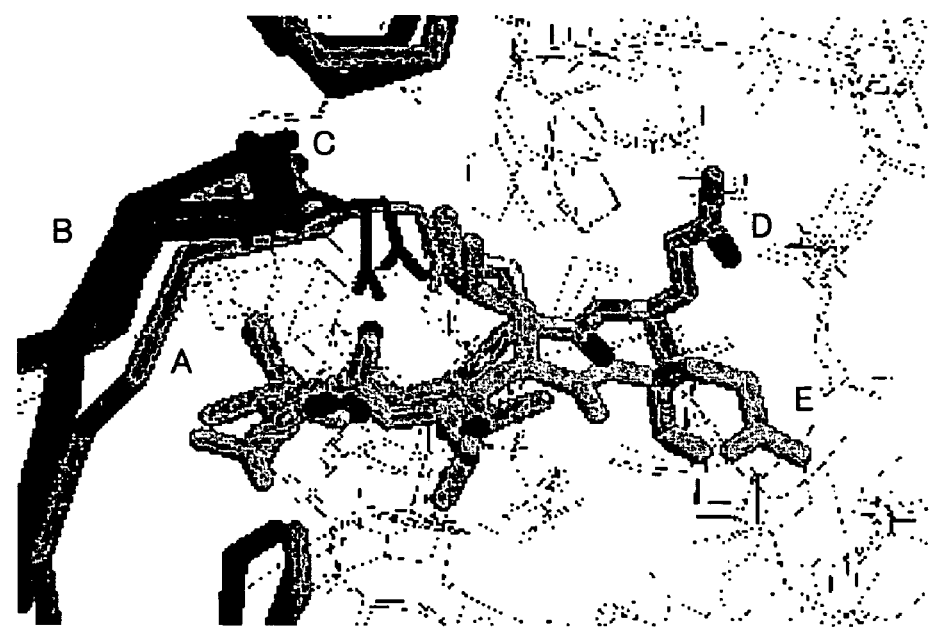
FIG. 81 is a view showing a result of comparison between 1UK3 and 1UK4.

In FIG. 81, 1UK3 are compared with 1UK4 which is a true structure. The ranking is 25th. Green A represents 1UK4 (B chain), blue B represents 1UK3 (B chain) in initial structure, red C represents optimum structure in ligand binding, "by element" cooler D represents a true structure of peptide ligand (ASN-SER-THR-LEU-GLN (SEQ ID NO: 7)) of 1UK4, and light blue E represents a calculated ligand. Rms of ligand was 2.5721. Rms with the true structure for main chain in active site was 1.0248 in initial structure, and 1.0792 in optimum structures.

Figure 82:
FIG. 82 is a view showing Ranking 1 of in silico screening.
Figures 83, 84:
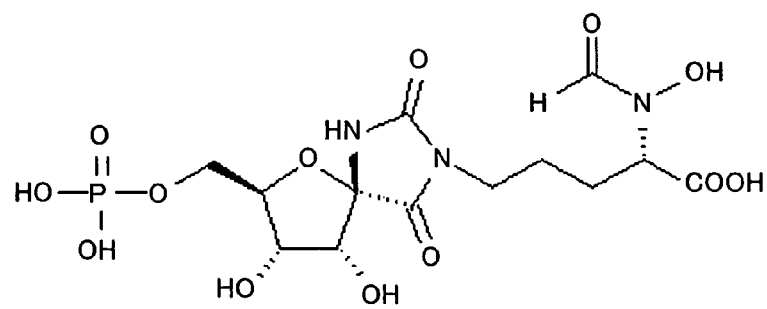
FIG. 83 is a view showing Ranking 1 of in silico screening.
FIG. 84 is a view showing structure-activity relationship information obtained from 1UK3 (B chain)

In FIG. 82 and FIG. 83, the first ranking of in silico screening is shown. In FIG. 83, (C8-R) hydantocidin 5'-phosphate which is a ligand of 1 QF4 is shown.

Case 2) Designating Three Spatial Points in SAR

FIG. 84 shows spatial points designating within active sites of 1UK3. FIG. 84 shows structure-activity relationship information obtained from 1UK3 (B chain).

Figure 85:
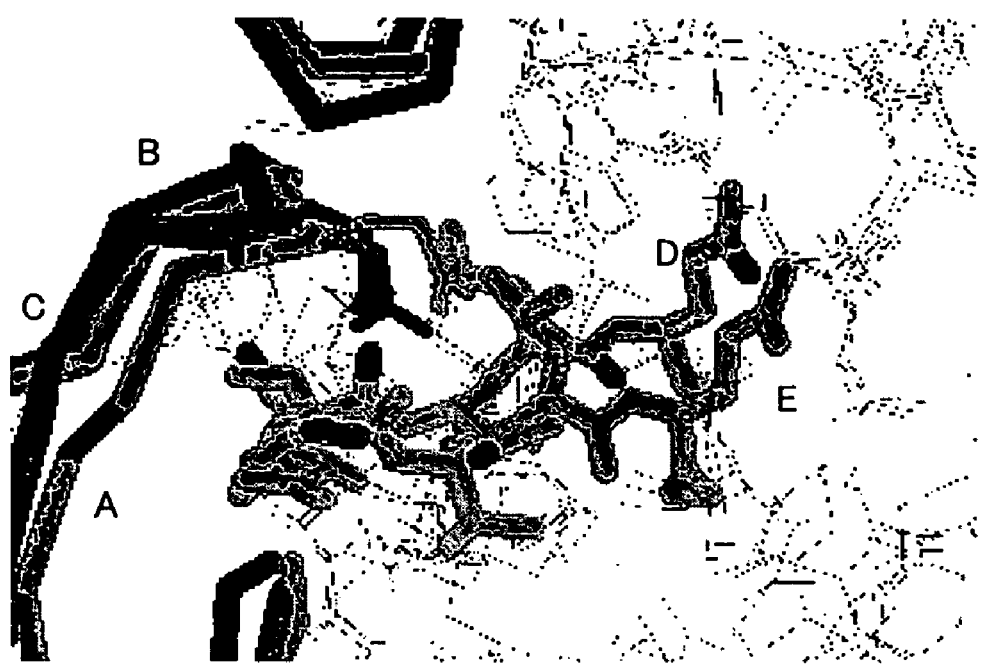
FIG. 85 is a view showing a result of a comparison between 1UK3 (B chain) and 1UK4 (B chain)

FIG. 85 shows a result of comparison between 1UK3 (B chain) and 1UK4 (B chain), and shows comparison of the optimum structure in 1UK3 with true structure. The ranking is 49th. Green A represents 1UK4 (B chain), blue B represents 1UK3 (B chain) in initial structure, red C represents optimum structure in ligand binding, "by element" cooler D represents a true structure of peptide ligand (ASN-SER-THR-LEU-GLN (SEQ ID NO: 7)) of 1UK4, and light blue E represents a calculated ligand. Rms of ligand was 2.0057. Rms with the true structure for main chain in active site was 1.0248 in initial structure, and 1.0469 in optimum structures.

In FIG. 86, a result of in silico screening executed while designating three spatial points of SAR is shown.

Case 3) Designating Five Spatial Points in SAR

FIG. 87 shows spatial points designating within active sites of 1UK3. FIG. 87 is of structure-activity relationship information obtained from 1UK3 (B chain). In FIG. 88 is shown a result of in silico screening (for example, high throughput screening) executed for five designated spatial points of SAR.

Figures 89, 90:
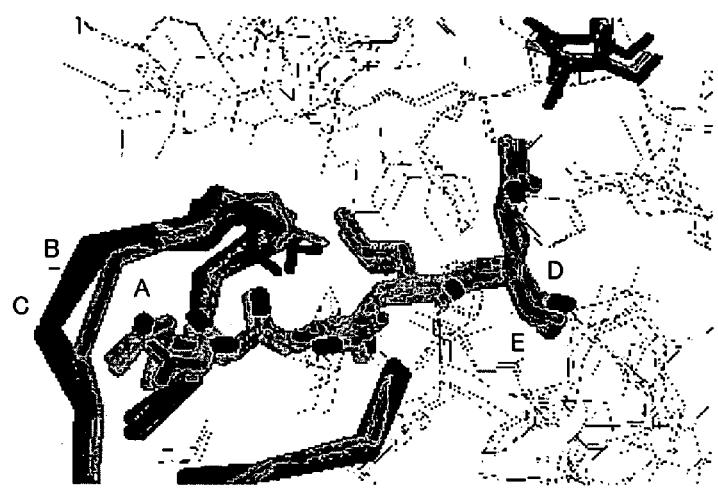
FIG. 89 is a view showing a result of a comparison between 1UK3 (B chain) and 1UK4 (B chain)
FIG. 90 is a view showing structure-activity relationship information obtained from 1UK3 (B chain)

FIG. 89 shows comparison between optimum structure and true structure in 1UK3. FIG. 89 shows a result of comparison between 1UK3 (B chain) and 1UK4 (B chain). The ranking is second. Green A represents 1UK4 (B chain), blue B represents 1UK3 (B chain) in initial structure, red C represents optimum structure in ligand binding, "by element" cooler D represents a true structure of peptide ligand (ASN-SER-THR-LEU-GLN (SEQ ID NO: 7)) of 1UK4, and light blue E represents a calculated ligand. Rms of ligand was 1.2578. Rms with the true structure for main chain in active site was 1.0248 in initial structure, and 1.1620 in optimum structures.

Case 4) Changing Designated Atom Type of Ligand Atom

FIG. 90 shows spatial points designating within active sites of 1UK3. FIG. 90 is of structure-activity relationship information obtained from 1UK3 (B chain). In FIG. 91 is shown a result of in silico screening (for example, high throughput screening) executed while changing the designated atom type of ligand atom.

Figures 92, 93:
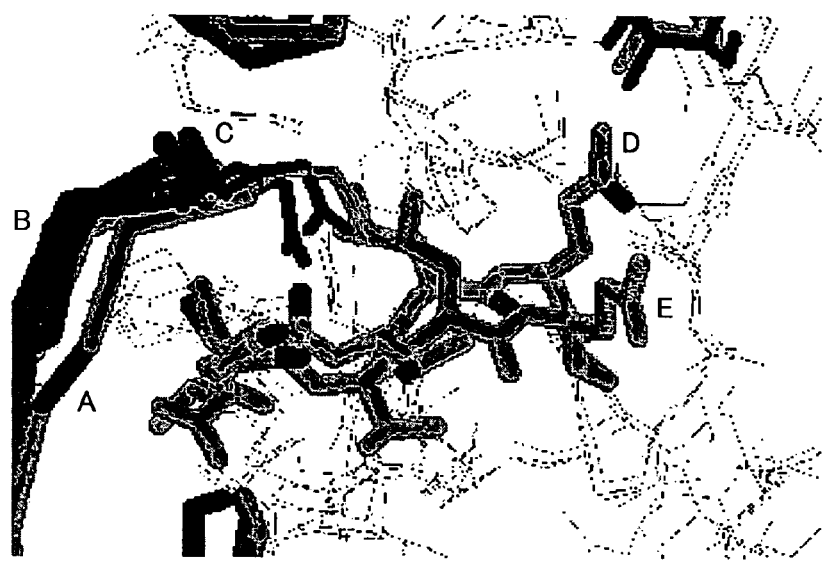
FIG. 92 is a view showing a result of a comparison between 1UK3 (B chain) and 1UK4 (B chain)
FIG. 93 is a view showing structure-activity relationship information obtained from 1UK4 (B chain)

FIG. 92 shows comparison between optimum structure and true structure in 1UK3. FIG. 92 shows a result of comparison between 1UK3 (B chain) and 1UK4 (B chain). The ranking is 774th. Green A represents 1UK4 (B chain), blue B represents 1UK3 (B chain) in initial structure, red C represents optimum structure in ligand binding, "by element" cooler D represents a true structure of peptide ligand (ASN-SER-THR-LEU-GLN (SEQ ID NO: 7)) of 1UK4, and light blue E represents a calculated ligand. Rms of ligand was 2.5216. Rms with the true structure for main chain in active site was 1.0248 in initial structure, and 1.0792 in optimum structures.

Case 5) Fixed Receptor

FIG. 93 shows spatial points designated within active sites. FIG. 93 is of structure-activity relationship information obtained from 1UK4 (B chain). In FIG. 94 shows shown a result of in silico screening (for example, high throughput screening) executed while fixing the receptor.

FIG. 95 shows comparison between experimentally observed and calculated structures of ligand, when 1UK3 is superimposed on 1UK4. The ranking is 39th. Structure of active site of 1UK3 is shown in gray, the former ligand is shown in black, and the latter ligand is shown in white.

As can be seen from Cases 1) to 4), the more SAR is designated, the better the ranking of the reference ligand is. That is, various ligands are caused to distribute in top ranking by conducting in silico screening with increased SAR information when binding information on reference ligand is reliable, and by reducing the number of information of SAR and designating the relaxed range of atom types in ligand when the information is unreliable. More reliable results were produced when in silico screening was executed with the use of SRA information modified based on the distribution information.

Case 1) and Case 5) demonstrate variation in ranking depending on the presence/absence of dynamic structure of receptor. Optimization of structures of ligand and receptor is superior in preventing collision of atoms to optimization of structure of only ligand. Therefore, the difference arose in optimization energy for placing ligand at the same position.

Sixth Example

Distribution of MD Parameter Concerning Parameters of Molecular Dynamic Calculation with Dihedral Angle Constrained Now an explanation will be given for distribution of parameter of MD with a dihedral angle constrained in an FMN-binding protein. Here, we verified whether similar results are obtained in molecular dynamic calculation with the dihedral angle constrained and parameters of clustering even for NMR structure along with 1LUD by means of the ligand screening apparatus 100 of the aforementioned embodiment. We selected MODEL 1 of NMR structure (PDB code: 1AXJ) of FMN-binding protein as an initial structure. As to the evaluation method, first example was followed except that parameters ($\alpha$=80.0%, $\alpha$=0.4 angstrom) for receptor dynamic structure clustering were fixed.

In FIG. 96, distribution of scores for determining parameter in molecular dynamic calculation with the dihedral angle constrained in 1AXJ is shown. FIG. 96 shows distribution of parameter of MD with the dihedral angle constrained in 1AXJ. The closer to A, the smaller the score is. As is the case with 1LUD, good results were obtained at a maximum value 800 and a minimum value 0 of dihedral angle constraint.

Seventh Example

MD with Dihedral Angle Constrained

Here, we verified the dynamic structure of each atom by a main chain in MD with a dihedral angle constrained by means of the ligand screening apparatus 100 in the aforementioned embodiment. There is sometimes the case that normal mode analysis does not converge and information of the dihedral angle fluctuation is not obtained. Since good results are obtained when MD is conducted with a constant constraint (500) with respect to the main chain dihedral angle as shown in FIG. 13, we verified the dynamic structure in this case. Following the first example, MD was conducted without constraint, with constraint using dihedral angle fluctuation or with constant constraint (500). In FIG. 97 to FIG. 108, results of dynamic behavior in each atom in molecular dynamic calculation executed for 1LUD are shown.

Figure 97:
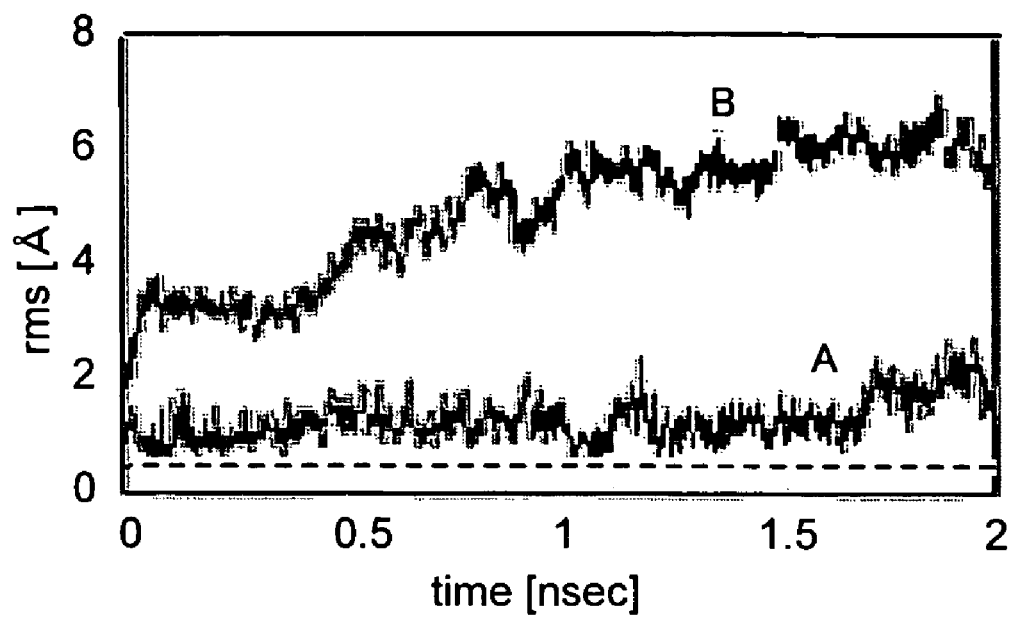
FIG. 97 is a view showing a result of an MD calculation of 1LUD (MODEL 1)
Figure 98:
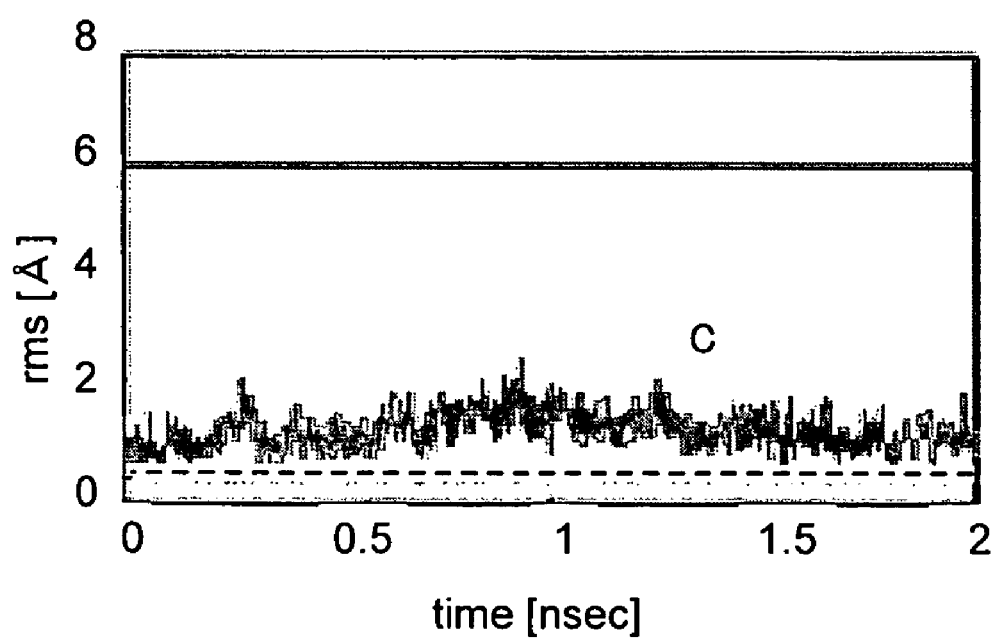
FIG. 98 is a view showing a result of an MD calculation of 1LUD (MODEL 1)
Figure 99:
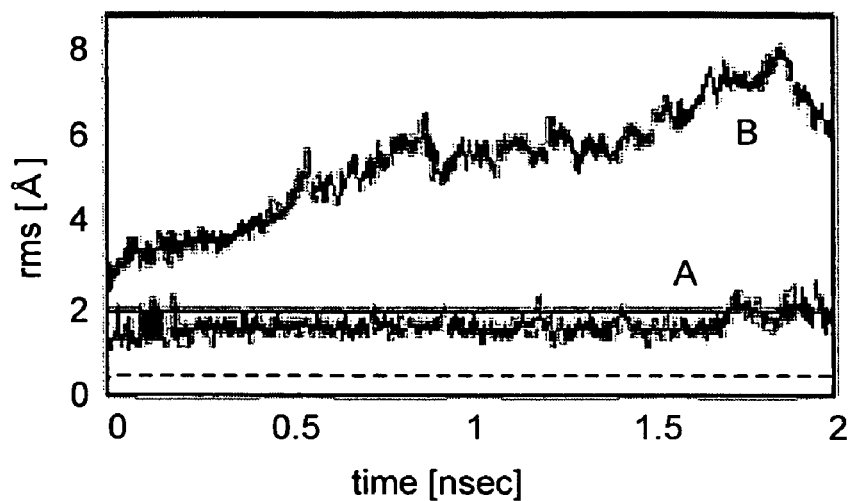
FIG. 99 is a view showing a result of an MD calculation of 1LUD (MODEL 1)
Figure 100:
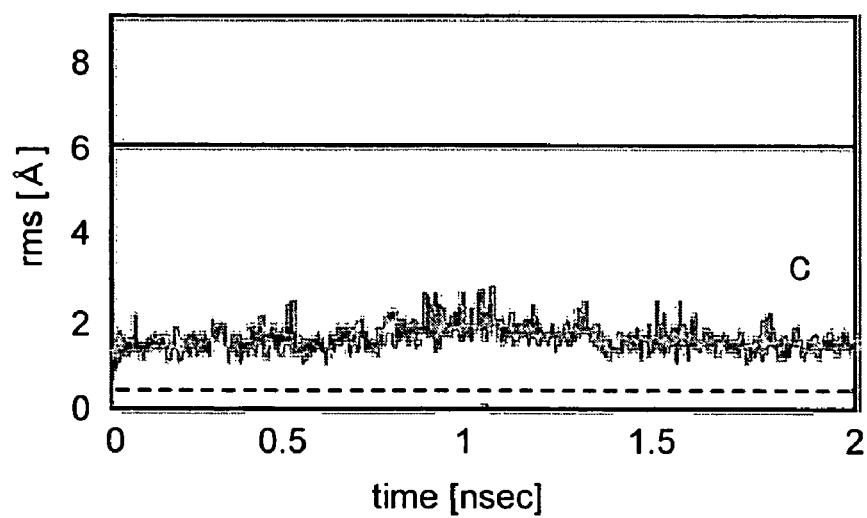
FIG. 100 is a view showing a result of an MD calculation of 1LUD (MODEL 1)
Figure 101:
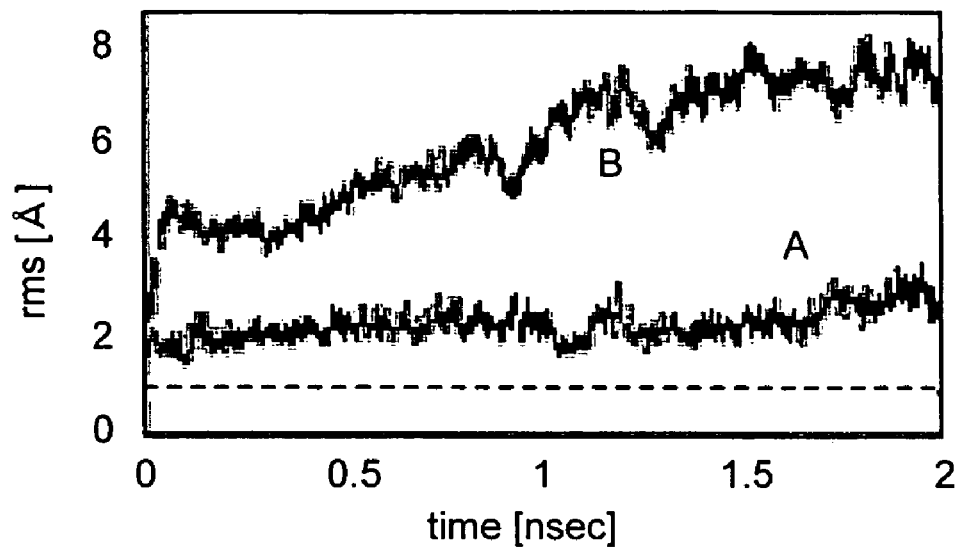
FIG. 101 is a view showing a result of an MD calculation of 1LUD (MODEL 1)
Figure 102:
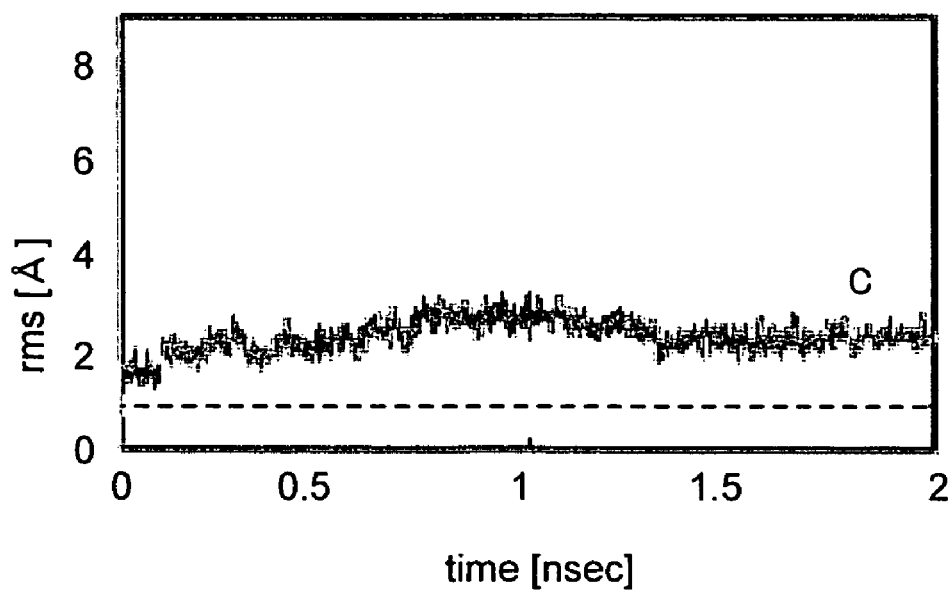
FIG. 102 is a view showing a result of an MD calculation of 1LUD (MODEL 1)
Figure 103:
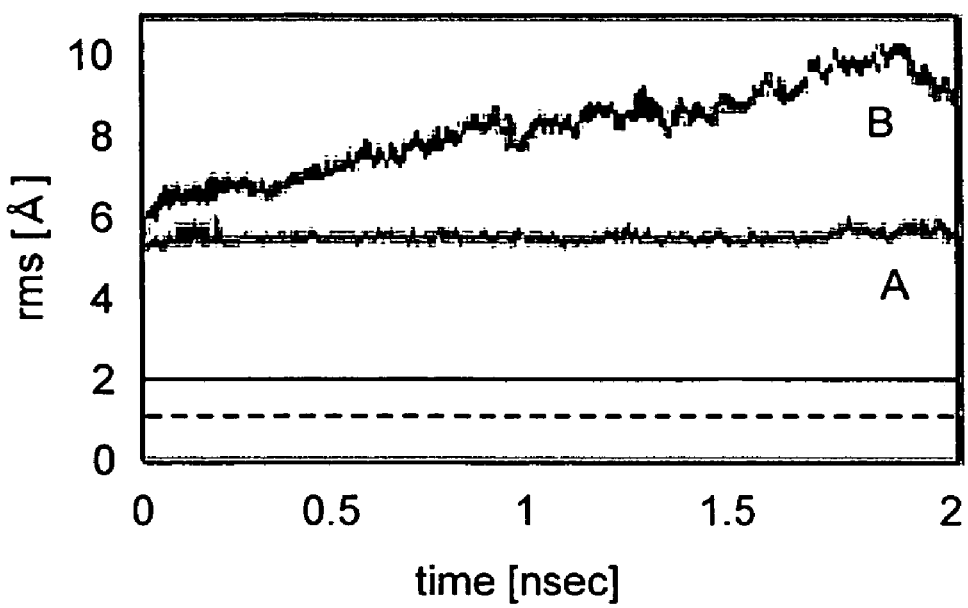
FIG. 103 is a view showing a result of an MD calculation of 1LUD (MODEL 1)
Figure 104:
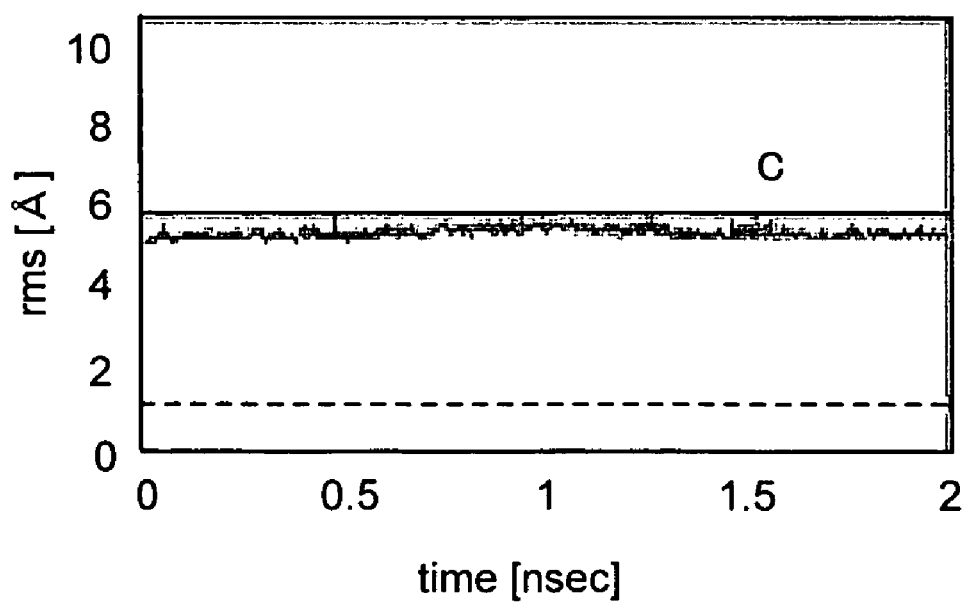
FIG. 104 is a view showing a result of an MD calculation of 1LUD (MODEL 1)
Figure 105:
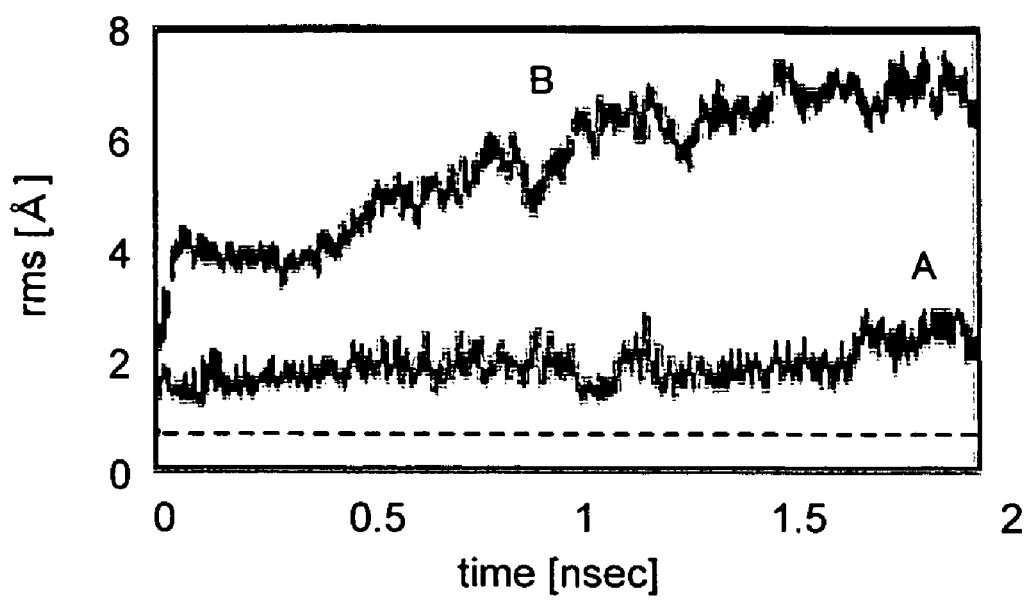
FIG. 105 is a view showing a result of an MD calculation of 1LUD (MODEL 1)
Figure 106:
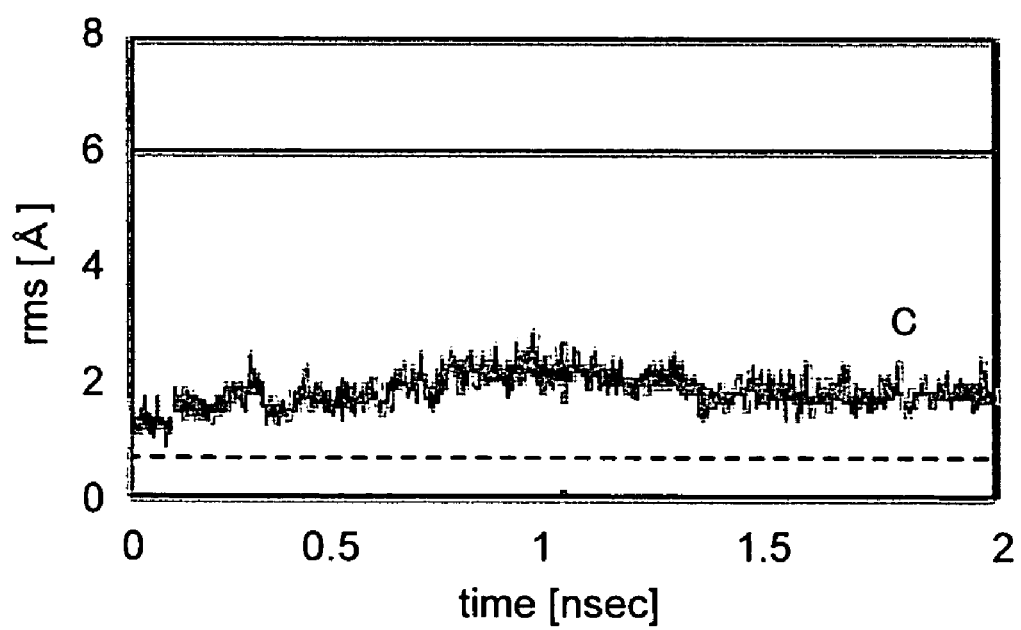
FIG. 106 is a view showing a result of an MD calculation of 1LUD (MODEL 1)
Figure 107:
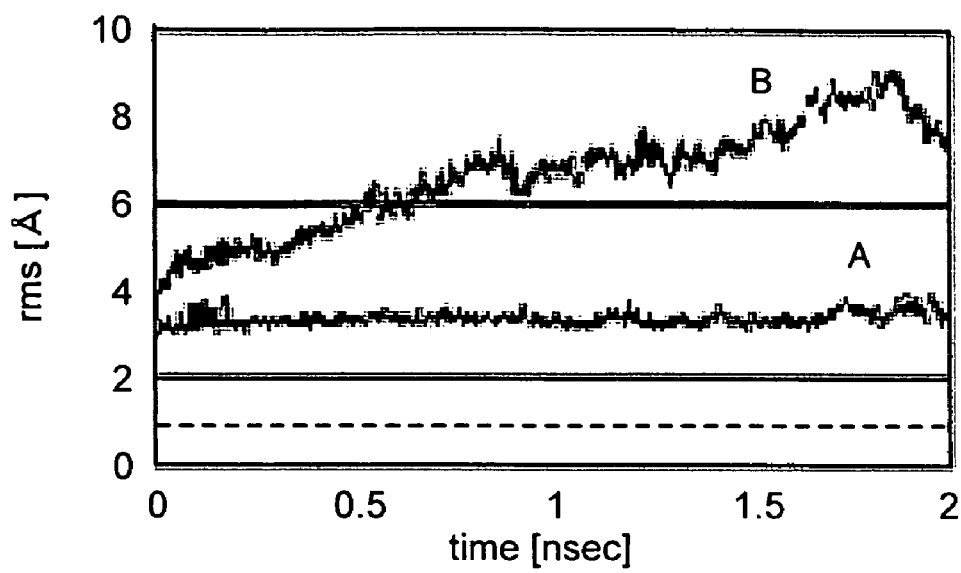
FIG. 107 is a view showing a result of an MD calculation of 1LUD (MODEL 1)
Figure 108:
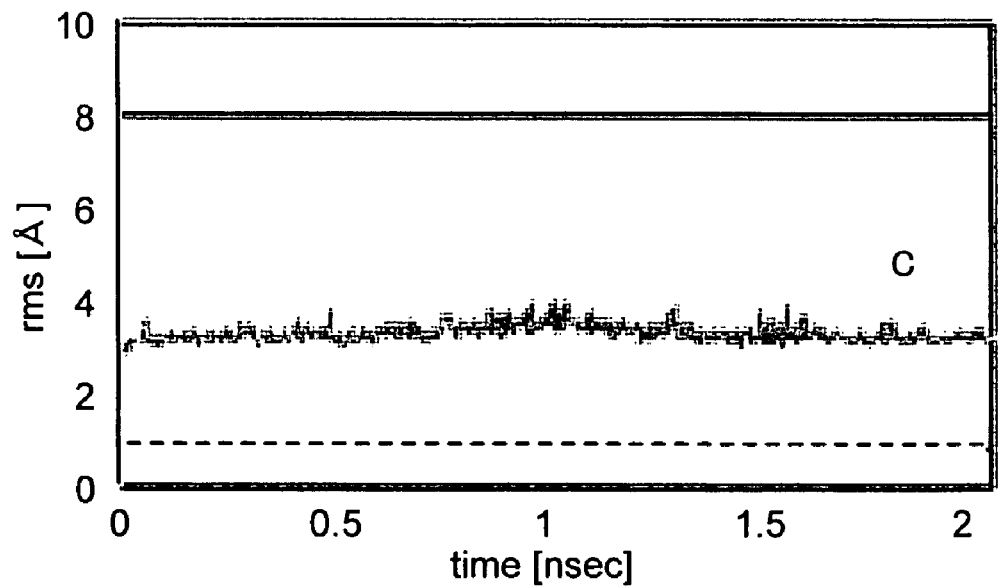
FIG. 108 is a view showing a result of an MD calculation of 1LUD (MODEL 1)

FIG. 97 to FIG. 108 are results of MD calculation for 1LUD (MODEL 1). FIG. 97 and FIG. 98 are results of dynamic behavior of a main chain atom in an active site, FIG. 99 and FIG. 100 are of the main chain atom in the receptor, FIG. 101 and FIG. 102 are of the side chain atom in the active site, FIG. 103 and FIG. 104 are of the side chain atom in the receptor, FIG. 105 and FIG. 106 are of the whole atom in the active site, and FIG. 107 and FIG. 108 are of the whole atom in the receptor. For each model structure of 24 kinds described in PDB file of 1LUD, rms with the main chain atom in active site by MD of MODEL 1 was calculated, and an average rms was displayed by dotted lines. The difference of the main atom in the active site from its initial structure was shown by rms in the presence (A) or absence (B) of dihedral angle constraint (A), or with a constant dihedral angle constraint (C).

Figure 109:
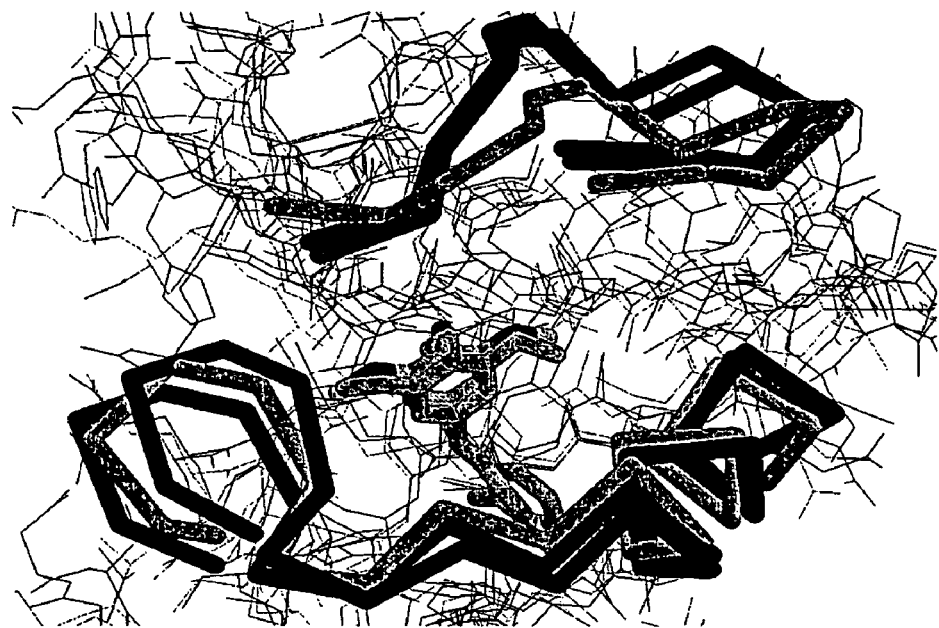
FIG. 109 is a view showing a result of receptor/ligand binding in a different condition.
Figure 110:
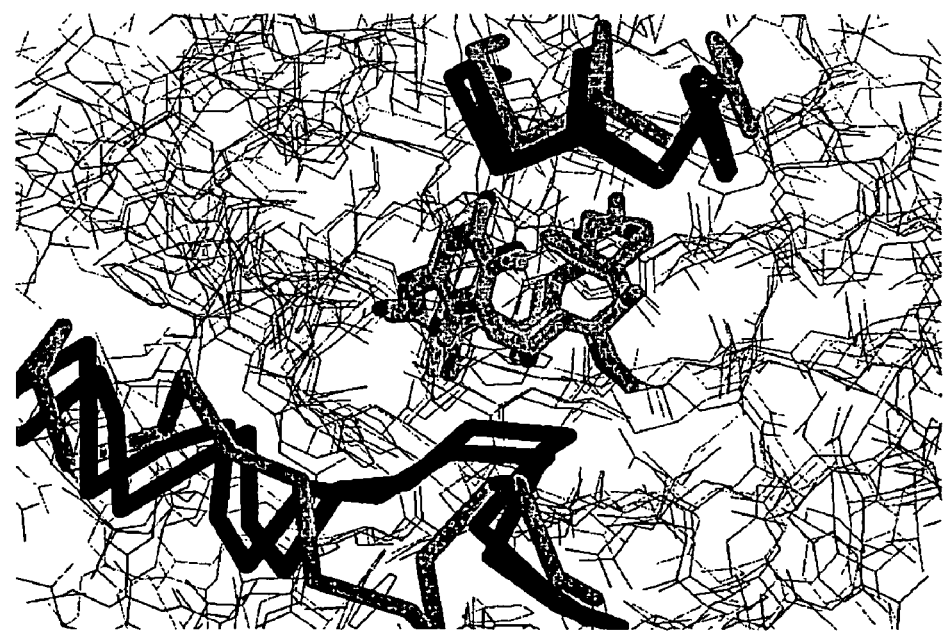
FIG. 110 is a view showing a result of receptor/ligand binding in a different condition.
Figures 111, 112:
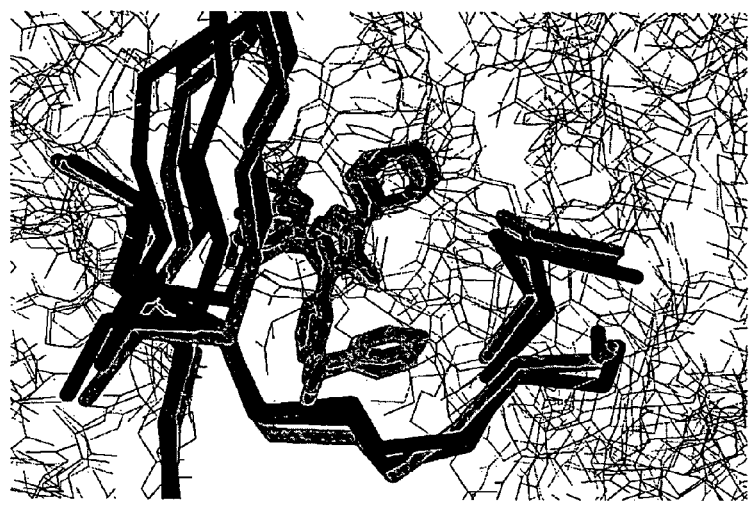
FIG. 111 is a view showing a result of receptor/ligand binding in a different condition.
FIG. 112 is a view showing structure-activity relationship information modified for 1BZF.

Although not shown herein, with regard to 1CBQ, 1J9G, 1MMB, 1BZF (MODEL 18), 1YER, 1A9U and 1UK3 (B chain), the results of the constrained MD based on fluctuation of a main chain dihedral angle demonstrated that a side chain atom not being constrained also exhibited a certain measurement of motion even if that of the main chain atom was constrained as is the case with FIGS. 109 to 111. It can be understood that motion of a main chain atom heavily influences on the motion of the receptor.

Eighth Example

Binding Analysis Under Different Conditions

Here, we verified that induction was caused even when different parameters were used in MD with a dihedral angle constrained and clustering by means of the ligand screening apparatus 100 in the aforementioned embodiment. The second example was followed except that the maximum value of constraint was set at 100, the minimum value was set at 0, the clustering coefficients α and β of the receptor dynamic structure were set at 80.0% and 1.0 angstroms, respectively. For clustering of the receptor dynamic structure, the structures were extracted at an interval of 100 femtoseconds within the range of 0 to 0.1 nanosecond was used, and a population of those was created. Receptor residues within 6 angstroms radius from each atom in the ligand are defined to form an active site.

In FIG. 109 to FIG. 111, results of receptor/ligand binding under different conditions are shown.

(i) In 1BZF (MODEL 18), binding of the ligand caused induction of 0.2686 in rms of main chain atom in the active site (FIG. 109). In overall rms of active site, induction of 0.1224 was caused. Rms of the ligand was 0.8526.
(ii) In 1YER, binding of the ligand caused induction of 0.22376 in rms of main chain atom in the active site (FIG. 110). In overall rms of the active site, induction of 0.0816 was caused. Rms of ligand was 0.7246.
(iii) In 1A9U, binding of the ligand caused induction of 0.2150 in rms of main chain atom in the active site (FIG. 111). In overall rms of the active site, induction of 0.0464 was caused. Rms of ligand was 0.9464.

Green lines show true structure, blue lines show initial structure, red lines show optimum structure, "by element" color lines show true ligand, and blue lines show optimum ligand.

As shown in FIG. 109 to FIG. 111, optimum results were obtained within a given condition even if each condition differs.

Ninth Example

Binding Analysis when True Structure is Selected as Initial Structure

Figure 113:
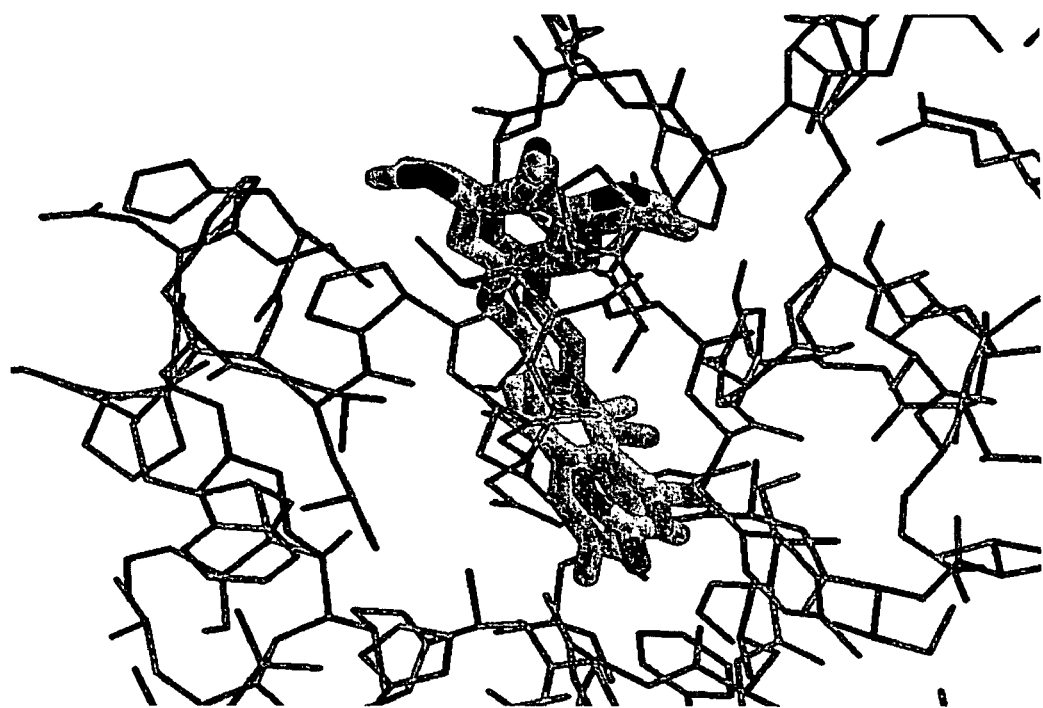
FIG. 113 is a view showing a result of ligand binding analysis of 1BZF (MODEL 18)
Figure 114:
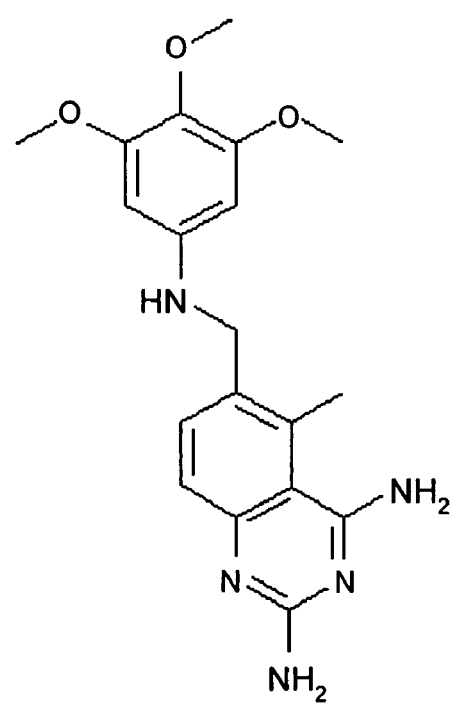
FIG. 114 is a view showing a result of ligand binding analysis of 1BZF (MODEL 18)

Here, since binding modes of 1BZF and 1LUD of DHFR resemble, binding analysis of ligand of 1BZF was conducted with partial modification of structure-activity relationship information by means of the ligand screening apparatus 100 in the aforementioned embodiment. The condition was such that 1BZF (MODEL 18) was used as initial structure, a cluster created from a population of 0 to 0.1 nanosecond was used. In FIG. 112, a spatial point designated in the active site of 1BZF is shown. FIG. 112 is a view of structure-activity relationship information modified for 1BZF. In FIG. 113 and FIG. 114, results of the receptor/ligand binding in 1BZF are shown. In FIG. 113 and FIG. 114, the results of ligand binding analysis of 1BZF (MODEL 18) are shown.

(i) As optimum structure of a receptor, initial structure was selected. Rms of ligand was 0.8884 (FIG. 113).
(ii) Trimetrexate, which is a ligand for 1BZF (MODEL 18) (FIG. 114).

Since the initial structure was a structure that was originally registered in PDB, namely optimum structure, the calculation results could be reproduced as shown in FIG. 113 and FIG. 114.

INDUSTRIAL APPLICABILITY

As described above, a ligand screening apparatus, a ligand screening method, and a program and recording medium according to the present invention seem to be very useful in the fields conducting analysis of receptor/ligand binding (drug design), especially for molecular design of pharmaceutical and agricultural chemicals. The present invention can be widely practiced in many industrial fields, especially in pharmaceutical, food, cosmetics, medical, structural analysis, functional analysis and the like fields, and hence are very useful.

The invention claimed is:

1. A ligand screening apparatus which screens for a ligand that binds to a protein when coordinate data of the protein of single chain or plural chains is given, the apparatus comprising:
- a post-structural-change protein coordinate data selecting unit that conducts structural change in the coordinate data of the protein while considering dynamic behavior, wherein said structural change is performed using an induced-fit parameter reflecting induced fit on the coordinate data of the protein and post-structural-change protein coordinate data is selected;
- a spatial point designating unit that designates a spatial point at which superposition with the ligand is to be conducted from the post-structural-change protein coordinate data selected by the post-structural-change protein coordinate data selecting unit;
- an interaction function calculating unit that calculates an interaction function when the protein and the ligand bind to each other using the spatial point designated by the spatial point designating unit and a ligand coordinate data of the ligand; and
- a ligand evaluating unit that evaluates the ligand that binds to the protein based on the interaction function calculated by the interaction function calculating unit.

2. The ligand screening apparatus according to claim 1, wherein the interaction function calculating unit calculates the interaction function using Sscore(i,j) shown in Formula 1:

$$Sscore(i, j) = \sum_{ij}^{\lambda} \begin{bmatrix} \text{when } i \text{ is not equal to } j \\ \alpha \times [\exp\{-(d_{ij}^s - d_{ij}^c)^2\} - \beta] / \frac{(d_{ij}^s + d_{ij}^c)^2}{2} \\ \text{when } i \text{ is equal to } j \\ \alpha \times (1 - \beta) \end{bmatrix}$$ [Formula 1]

wherein $d_{ij}^s$ is a distance between i-th spatial point and j-th spatial point in the target protein, $d_{ij}^c$ is an interatomic distance between i-th atom and j-th atom in a compound, $\alpha$ is a coefficient for making Sscore(i,j) the maximum value when the group of spatial points in the target protein and the compound completely overlap with each other, $\beta$ is a coefficient for giving a threshold value by which it can be defined as "overlapping".

3. The ligand screening apparatus according to claim 1, wherein the interaction function calculating unit further comprises an interaction function optimizing unit that carries out optimization so as to make the score of interaction function maximum.

4. The ligand screening apparatus according to claim 3, wherein the interaction function calculating unit further comprises:

- an interaction energy optimizing unit that calculates interaction energy with the protein for the superposed ligand after optimization of the interaction function by the interaction function optimizing unit, and optimizes the interaction energy while finely adjusting conformation of ligand 3D structure data.

5. The ligand screening apparatus according to claim 4, wherein the ligand evaluating unit further comprises:
- a reevaluating unit that causes execution of the interaction function calculating unit after largely changing conformation of ligand 3D structure data following optimization by the interaction energy optimizing unit, and reevaluates the ligand that binds to the protein based on the interaction function calculated by the interaction function calculating unit.

6. The ligand screening apparatus according to claim 1, wherein in calculation of any one of the induced-fit parameter and the post-structural-change protein coordinate data or both, the post-structural-change protein coordinate data selecting unit calculates a normal mode for the protein coordinate data, determines intensity of fluctuation of each amino acid, and conducts a molecular dynamic calculation using the intensity of fluctuation as a constraint condition.

7. The ligand screening apparatus according to claim 6, wherein the post-structural-change protein coordinate data selecting unit calculates a fluctuation value of a dihedral angle of a main chain according to normal mode calculation, and conducts a molecular dynamic calculation while setting the fluctuation value as a coefficient of force K in the molecular dynamic calculation shown by Formula 2 or Formula 3:

$$Erot = Krot(\phi - \phi 0)^2$$ [Formula 2]

wherein Erot represents energy of a dihedral angle of a main chain atom in a 3D structure of a protein, $\phi$ represents a dihedral angle of the main chain atom, $\phi 0$ represents a standard value of the dihedral angle of the main chain atom, when a value of Krot (a coefficient of force) is large, $\phi$ is constrained by $\phi 0$, $$Epos = Kpos(r - r0)^2$$ [Formula 3]

wherein Epos represents position energy of the main chain atom in a 3D structure of a protein, r represents a coordinate of the main chain atom, r0 represents a standard value of the coordinate of the main chain atom, when a value of Kpos (a coefficient of force) is large, r is constrained by r0.

8. The ligand screening apparatus according to claim 1, wherein the interaction function calculating unit uses the interaction function to which a dynamic property function representing dynamic property of protein is added as "elastic energy".

9. The ligand screening apparatus according to claim 8, wherein the interaction function calculating unit adapts "U collision" as "elastic energy" which is a function shown by Formula 4 in consideration of local flexibility of the protein $$U_{collision} = \sum_{i=1}^{M}\sum_{j=1}^{N} \varphi(i,j) \qquad \text{[Formula 4]}$$

$$\varphi(i,j) = Kcollision * (Rcollision(i,j) - R)^2$$

wherein M is a number of atoms in an active site that prohibit collision, N is a number of atoms of the ligand, interatomic distance R between an i-th atom of a main chain or a side chain with a little dynamic behavior in an active site, and a j-th atom in the ligand is not more than collision distance "Rcollision(i,j)", φ(i,j) is calculated.

10. The ligand screening apparatus according to claim 1, wherein the interaction function calculating unit uses the interaction function to which a normal mode analysis result or secondary structure determination result of the protein is added as a dynamic property function that represents a dynamic property of the protein.

11. A ligand screening method which screens for a ligand that binds to a protein when coordinate data of the protein of single chain or plural chains is given, the method comprising:
a post-structural-change protein coordinate data selecting step that conducts, with a computer, structural change in the coordinate data of the protein while considering dynamic behavior, wherein said structural change is performed using an induced-fit parameter reflecting induced fit on the coordinate data of the protein and post-structural-change protein coordinate data is selected;
a spatial point designating step that designates a spatial point at which superposition with the ligand is to be conducted from the post-structural-change protein coordinate data selected by the post-structural-change protein coordinate data selecting step;
an interaction function calculating step that calculates an interaction function when the protein and the ligand bind to each other using the spatial point designated by the spatial point designating step and a ligand coordinate data of the ligand; and
a ligand evaluating step that evaluates the ligand that binds to the protein based on the interaction function calculated by the interaction function calculating step;
wherein the interaction function calculating step calculates the interaction function using Sscore(i,j) shown in Formula 1:

$$Sscore(i,j) = \sum_{ij}^{\lambda} \begin{bmatrix} \text{when } i \text{ is not equal to } j \\ \alpha \times [\exp\{-(d_{ij}^s - d_{ij}^c)^2\} - \beta] \Big/ \frac{(d_{ij}^s + d_{ij}^c)^2}{2} \\ \text{when } i \text{ is equal to } j \\ \alpha \times (1-\beta) \end{bmatrix} \qquad \text{[Formula 1]}$$

wherein $d_{ij}^s$ is a distance between i-th spatial point and j-th spatial point in the target protein, $d_{ij}^c$ is an interatomic distance between i-th atom and j-th atom in a compound, α is a coefficient for making Sscore(i,j) the maximum value when the group of spatial points in the target protein and the compound completely overlap with each other, β is a coefficient for giving a threshold value by which it can be defined as "overlapping".

12. The ligand screening method according to claim 11, wherein the interaction function calculating step further comprises an interaction function optimizing step that carries out optimization so as to make the score of interaction function maximum.

13. The ligand screening method according to claim 12, wherein the interaction function calculating step further comprises:
an interaction energy optimizing step that calculates interaction energy with the protein for the superposed ligand after optimization of the interaction function by the interaction function optimizing step, and optimizes the interaction energy while finely adjusting conformation of ligand 3D structure data.

14. The ligand screening method according to claim 13, wherein the ligand evaluating step further comprises:
a reevaluating step that causes execution of the interaction function calculating step after largely changing conformation of ligand 3D structure data following optimization by the interaction energy optimizing step, and reevaluates the ligand that binds to the protein based on the interaction function calculated by the interaction function calculating step.

15. The ligand screening method according to claim 11, wherein in calculation of any one of the induced-fit parameter and the post-structural-change protein coordinate data or both, the post-structural-change protein coordinate data selecting step calculates a normal mode for the protein coordinate data, determines intensity of fluctuation of each amino acid, and conducts a molecular dynamic calculation using the intensity of fluctuation as a constraint condition.

16. The ligand screening method according to claim 15, wherein the post-structural-change protein coordinate data selecting step calculates a fluctuation value of a dihedral angle of a main chain according to normal mode calculation, and conducts a molecular dynamic calculation while setting the fluctuation value as a coefficient of force K in the molecular dynamic calculation shown by Formula 2 or Formula 3:

$$Erot = Krot(\phi - \phi 0)^2 \qquad \text{[Formula 2]}$$

wherein Erot represents energy of a dihedral angle of a main chain atom in a 3D structure of a protein, φ represents a dihedral angle of the main chain atom, φ0 represents a standard value of the dihedral angle of the main chain atom, when a value of Krot (a coefficient of force) is large, φ is constrained by φ0, $$Epos = Kpos(r - r0)^2 \qquad \text{[Formula 3]}$$

wherein Epos represents position energy of the main chain atom in a 3D structure of a protein r represents a coordinate of the main chain atom, r0 represents a standard value of the coordinate of the main chain atom, when a value of Kpos (a coefficient of force) is large, r is constrained by r0.

17. The ligand screening method according to claim 11, wherein the interaction function calculating step uses the interaction function to which a dynamic property function representing dynamic property of protein is added as "elastic energy".

18. The ligand screening method according to claim 17, wherein the interaction function calculating step adapts "U collision" as "elastic energy" which is a function shown by Formula 4 in consideration of local flexibility of protein:

$$U_{collision} = \sum_{i=1}^{M} \sum_{j=1}^{N} \varphi(i, j)$$ [Formula 4]

$$\varphi(i, j) = Kcollision * (Rcollision(i, j) - R)^2$$

wherein M is a number of atoms in an active site that prohibit collision, N is a number of atoms of ligand, interatomic distance R between an i-th atom of a main chain or a side chain with a little dynamic behavior in an active site, and a j-th atom in the ligand is not more than collision distance "Rcollision(i,j)", φ(i,j) is calculated.

19. The ligand screening method according to claim 11, wherein the interaction function calculating step uses the interaction function to which a normal mode analysis result or secondary structure determination result of the protein is added as a dynamic property function that represents a dynamic property of the protein.

20. A non-transitory computer-readable medium having a program which makes a computer execute a ligand screening method which screens for a ligand that binds to a protein when coordinate data of the protein of single chain or plural chains is given, the method comprising:
 a post-structural-change protein coordinate data selecting step that conducts structural change in the coordinate data of the protein while considering dynamic behavior, wherein said structural change is performed using an induced-fit parameter reflecting induced fit on the coordinate data of the protein and post-structural-change protein coordinate data is selected;
 a spatial point designating step that designates a spatial point at which superposition with the ligand is to be conducted, from the post-structural-change protein coordinate data selected by the post-structural-change protein coordinate data selecting step;
 an interaction function calculating step that calculates an interaction function when the protein and the ligand bind to each other using the spatial point designated by the spatial point designating step and a ligand coordinate data of the ligand; and
 a ligand evaluating step that evaluates the ligand that binds to the protein based on the interaction function calculated by the interaction function calculating step;
 wherein the interaction function calculating step calculates the interaction function using Sscore(i,j) shown in Formula 1

$$Sscore(i, j) = \sum_{ij}^{\lambda} \begin{bmatrix} \text{when } i \text{ is not equal to } j \\ \alpha \times [\exp\{-(d_{ij}^s - d_{ij}^c)^2\} - \beta] \Big/ \frac{(d_{ij}^s + d_{ij}^c)^2}{2} \\ \text{when } i \text{ is equal to } j \\ \alpha \times (1 - \beta) \end{bmatrix}$$ [Formula 1]

wherein $d_{ij}^s$ is a distance between i-th spatial point and j-th spatial point in the target protein, $d_{ij}^c$ is an interatomic distance between i-th atom and j-th atom in a compound, α is a coefficient for making Sscore(i,j) the maximum value when the group of spatial points in the target protein and the compound completely overlap with each other, β is a coefficient for giving a threshold value by which it can be defined as "overlapping".

21. The non-transitory computer-readable medium having a program according to claim 20, wherein the interaction function calculating step further comprises an interaction function optimizing step that carries out optimization so as to make the score of interaction function maximum.

22. The non-transitory computer-readable medium having a program according to claim 21, wherein the interaction function calculating step further comprises:
 an interaction energy optimizing step that calculates interaction energy with the protein for the superposed ligand after optimization of the interaction function by the interaction function optimizing step, and optimizes the interaction energy while finely adjusting conformation of ligand 3D structure data.

23. The non-transitory computer-readable medium having a program according to claim 22, wherein the ligand evaluating step further comprises:
 a reevaluating step that causes execution of the interaction function calculating step after largely changing conformation of ligand 3D structure data following optimization by the interaction energy optimizing step, and reevaluates the ligand that binds to the protein based on the interaction function calculated by the interaction function calculating step.

24. The non-transitory computer-readable medium having a program according to claim 20, wherein in calculation of any one of the induced-fit parameter and the post-structural-change protein coordinate data or both, the post-structural-change protein coordinate data selecting step calculates a normal mode for the protein coordinate data, determines intensity of fluctuation of each amino acid, and conducts a molecular dynamic calculation using the intensity of fluctuation as a constraint condition.

25. The non-transitory computer-readable medium having a program according to claim 24, wherein the post-structural-change protein coordinate data selecting step calculates a fluctuation value of a dihedral angle of a main chain according to the normal mode calculation, and conducts the molecular dynamic calculation while setting the fluctuation value as a coefficient of force K in the molecular dynamic calculation shown by Formula 2 or Formula 3:

$$Erot = Krot(\phi - \phi 0)^2$$ [Formula 2]

wherein Erot represents energy of a dihedral angle of a main chain atom in a 3D structure of a protein, φ represents the dihedral angle of the main chain atom, φ0 represents a standard value of the dihedral angle of the main chain atom, when a value of Krot (a coefficient of force) is large, φ is constrained by φ0, $$Epos = Kpos(r - r0)^2$$ [Formula 3]

wherein Epos represents a position energy of the main chain atom in 3D structure of a protein, r represents a coordinate of the main chain atom, r0 represents a standard value of the coordinate of the main chain atom, when a value of Kpos (a coefficient of force) is large, r is constrained by r0.

26. The program according to claim 20, wherein the interaction function calculating step uses the interaction function to which a dynamic property function representing dynamic property of protein is added as "elastic energy".

27. The non-transitory computer-readable medium having a program according to claim 26, wherein the interaction function calculating step adapts "U collision" as "elastic energy" which is a function shown by Formula 4 in consideration of local flexibility of protein:

$$U_{collision} = \sum_{i=1}^{M} \sum_{j=1}^{N} \varphi(i, j)$$

$$\varphi(i, j) = Kcollision * (Rcollision(i, j) - R)^2$$

[Formula 4]

wherein M is a number of atoms in an active site that prohibit collision, N is a number of atoms of ligand, interatomic distance R between an i-th atom of a main chain or a side chain with a little dynamic behavior in active site, and a j-th atom in the ligand is not more than collision distance "Rcollision(i,j)", φ(i,j) is calculated.

28. The non-transitory computer-readable medium having a program according to claim 20, wherein the interaction function calculating step uses the interaction function to which a normal mode analysis result or secondary structure determination result of the protein is added as a dynamic property function that represents a dynamic property of the protein.

* * * * *

SEQUENCE LISTING

<160> NUMBER OF SEQ ID NOS: 7

<210> SEQ ID NO 1

```
<211> LENGTH: 137
<212> TYPE: PRT
<213> ORGANISM: Unknown
<220> FEATURE:
<223> OTHER INFORMATION: Description of Unknown: Cellular retinoic acid
      binding protein type II (CRABP-II) (PDB code: 1CBQ)

<400> SEQUENCE: 1

Pro Asn Phe Ser Gly Asn Trp Lys Ile Ile Arg Ser Glu Asn Phe Glu
1               5                   10                  15

Glu Leu Leu Lys Val Leu Gly Val Asn Val Met Leu Arg Lys Ile Ala
            20                  25                  30

Val Ala Ala Ala Ser Lys Pro Ala Val Glu Ile Lys Gln Glu Gly Asp
        35                  40                  45

Thr Phe Tyr Ile Lys Thr Ser Thr Thr Val Arg Thr Thr Glu Ile Asn
50                  55                  60

Phe Lys Val Gly Glu Glu Phe Glu Glu Gln Thr Val Asp Gly Arg Pro
65                  70                  75                  80

Cys Lys Ser Leu Val Lys Trp Glu Ser Glu Asn Lys Met Val Cys Glu
                85                  90                  95

Gln Lys Leu Leu Lys Gly Glu Gly Pro Lys Thr Ser Trp Thr Arg Glu
            100                 105                 110

Leu Thr Asn Asp Gly Glu Leu Ile Leu Thr Met Thr Ala Asp Asp Val
        115                 120                 125

Val Cys Thr Arg Val Tyr Val Arg Glu
130                 135

<210> SEQ ID NO 2
<211> LENGTH: 131
<212> TYPE: PRT
<213> ORGANISM: Unknown
<220> FEATURE:
<223> OTHER INFORMATION: Description of Unknown: Intestinal fatty acid
      binding protein (PDB code: 1ICM)

<400> SEQUENCE: 2

Ala Phe Asp Gly Thr Trp Lys Val Asp Arg Asn Glu Asn Tyr Glu Lys
1               5                   10                  15

Phe Met Glu Lys Met Gly Ile Asn Val Val Lys Arg Lys Leu Gly Ala
            20                  25                  30

His Asp Asn Leu Lys Leu Thr Ile Thr Gln Gly Gly Asn Lys Phe Thr
        35                  40                  45

Val Lys Glu Ser Ser Asn Phe Arg Asn Ile Asp Val Val Phe Glu Leu
50                  55                  60

Gly Val Asp Phe Ala Tyr Ser Leu Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Glu
130

<210> SEQ ID NO 3
<211> LENGTH: 147
<212> TYPE: PRT
<213> ORGANISM: Unknown
<220> FEATURE:
```

```
<223> OTHER INFORMATION: Description of Unknown: Fravodoxin (PDB code:
      1J9G)

<400> SEQUENCE: 3

Ala Lys Ala Leu Ile Val Tyr Gly Ser Thr Thr Gly Asn Thr Glu Tyr
1               5                   10                  15

Thr Ala Glu Thr Ile Ala Arg Glu Leu Ala Asp Ala Gly Tyr Glu Val
                20                  25                  30

Asp Ser Arg Asp Ala Ala Ser Val Glu Ala Gly Gly Leu Phe Glu Gly
            35                  40                  45

Phe Asp Leu Val Leu Leu Gly Cys Ser Thr Trp Gly Asp Asp Cys Ile
    50                  55                  60

Glu Leu Gln Asp Asp Phe Ile Pro Leu Phe Asp Ser Leu Glu Glu Thr
65                  70                  75                  80

Gly Ala Gln Gly Arg Lys Val Ala Cys Phe Gly Cys Gly Asp Ser Ser
                85                  90                  95

Tyr Glu Tyr Phe Cys Gly Ala Val Asp Ala Ile Glu Glu Lys Leu Lys
            100                 105                 110

Asn Leu Gly Ala Glu Ile Val Gln Asp Gly Leu Arg Ile Asp Gly Asp
        115                 120                 125

Pro Arg Ala Ala Arg Asp Asp Ile Val Gly Trp Ala His Asp Val Arg
130                 135                 140

Gly Ala Ile
145

<210> SEQ ID NO 4
<211> LENGTH: 165
<212> TYPE: PRT
<213> ORGANISM: Unknown
<220> FEATURE:
<223> OTHER INFORMATION: Description of Unknown: Flavodoxin (PDB code:
      1AHN)

<400> SEQUENCE: 4

Ala Ile Thr Gly Ile Phe Phe Gly Ser Asp Thr Gly Asn Thr Glu Asn
1               5                   10                  15

Ile Ala Lys Met Ile Gln Lys Gln Leu Gly Lys Asp Val Ala Asp Val
                20                  25                  30

His Asp Ile Ala Lys Ser Ser Lys Glu Asp Leu Glu Ala Tyr Asp Ile
            35                  40                  45

Leu Leu Leu Gly Ile Pro Thr Trp Tyr Tyr Gly Glu Ala Gln Cys Asp
    50                  55                  60

Trp Asp Asp Phe Phe Pro Thr Leu Glu Glu Ile Asp Phe Asn Gly Lys
65                  70                  75                  80

Leu Val Ala Leu Phe Gly Cys Gly Asp Gln Glu Asp Tyr Ala Glu Tyr
                85                  90                  95

Phe Cys Asp Ala Leu Gly Thr Ile Arg Asp Ile Ile Glu Pro Arg Gly
            100                 105                 110

Ala Thr Ile Val Gly His Trp Pro Thr Ala Gly Tyr His Phe Glu Ala
        115                 120                 125

Ser Lys Gly Leu Ala Asp Asp Asp His Phe Val Gly Leu Ala Ile Asp
130                 135                 140

Glu Asp Arg Gln Pro Glu Leu Thr Ala Glu Arg Val Glu Lys Trp Val
145                 150                 155                 160

Lys Gln Ile Ser Glu
                165
```

```
<210> SEQ ID NO 5
<211> LENGTH: 158
<212> TYPE: PRT
<213> ORGANISM: Unknown
<220> FEATURE:
<223> OTHER INFORMATION: Description of Unknown: Matrix
      metalloproteinase-8 (MMP-8) (PDB code: 1MMB)

<400> SEQUENCE: 5

Asn Pro Lys Trp Glu Arg Thr Asn Leu Thr Tyr Arg Ile Arg Asn Tyr
1               5                   10                  15

Thr Pro Gln Leu Ser Glu Ala Glu Val Glu Arg Ala Ile Lys Asp Ala
            20                  25                  30

Phe Glu Leu Trp Ser Val Ala Ser Pro Leu Ile Phe Thr Arg Ile Ser
        35                  40                  45

Gln Gly Glu Ala Asp Ile Asn Ile Ala Phe Tyr Gln Arg Asp His Gly
    50                  55                  60

Asp Asn Ser Pro Phe Asp Gly Pro Asn Gly Ile Leu Ala His Ala Phe
65                  70                  75                  80

Gln Pro Gly Gln Gly Ile Gly Gly Asp Ala His Phe Asp Ala Glu Glu
                85                  90                  95

Thr Trp Thr Asn Thr Ser Ala Asn Tyr Asn Leu Phe Leu Val Ala Ala
            100                 105                 110

His Glu Phe Gly His Ser Leu Gly Leu Ala His Ser Ser Asp Pro Gly
        115                 120                 125

Ala Leu Met Tyr Pro Asn Tyr Ala Phe Arg Glu Thr Ser Asn Tyr Ser
    130                 135                 140

Leu Pro Gln Asp Asp Ile Asp Gly Ile Gln Ala Ile Tyr Gly
145                 150                 155

<210> SEQ ID NO 6
<211> LENGTH: 159
<212> TYPE: PRT
<213> ORGANISM: Unknown
<220> FEATURE:
<223> OTHER INFORMATION: Description of Unknown: MMP-3 (PDB code: 1B3D)

<400> SEQUENCE: 6

Ile Pro Lys Trp Arg Lys Thr His Leu Thr Tyr Arg Ile Val Asn Tyr
1               5                   10                  15

Thr Pro Asp Leu Pro Lys Asp Ala Val Asp Ser Ala Val Glu Lys Ala
            20                  25                  30

Leu Lys Val Trp Glu Glu Val Thr Pro Leu Thr Phe Ser Arg Leu Tyr
        35                  40                  45

Glu Gly Glu Ala Asp Ile Met Ile Ser Phe Ala Val Arg Glu His Gly
    50                  55                  60

Asp Phe Tyr Pro Phe Asp Gly Pro Gly Asn Val Leu Ala His Ala Tyr
65                  70                  75                  80

Ala Pro Gly Pro Gly Ile Asn Gly Asp Ala His Phe Asp Asp Asp Glu
                85                  90                  95

Gln Trp Thr Lys Asp Thr Thr Gly Thr Asn Leu Phe Leu Val Ala Ala
            100                 105                 110

His Glu Ile Gly His Ser Leu Gly Leu Phe His Ser Ala Asn Thr Glu
        115                 120                 125

Ala Leu Met Tyr Pro Leu Tyr His Ser Leu Thr Asp Leu Thr Arg Phe
    130                 135                 140

Arg Leu Ser Gln Asp Asp Ile Asn Gly Ile Gln Ser Leu Tyr Gly
145                 150                 155
```

```
<210> SEQ ID NO 7
<211> LENGTH: 5
<212> TYPE: PRT
<213> ORGANISM: Unknown
<220> FEATURE:
<223> OTHER INFORMATION: Description of Unknown: Peptide ligand
      (PDB code: 1UK4)

<400> SEQUENCE: 7

Asn Ser Thr Leu Gln
1               5
```